US012741004B2

(12) United States Patent
Goldstein

(10) Patent No.: US 12,741,004 B2
(45) Date of Patent: Sep. 22, 2026

(54) COMPOSITION AND METHODS OF TREATMENT FOR SKIN HEALTH AND SLEEP QUALITY USING SYNERGISTICALLY-ENHANCED SUPPLEMENTATION

(71) Applicant: Xygenyx, Inc., Pleasant Hill, CA (US)

(72) Inventor: Alexy Goldstein, LaFayette, CA (US)

(73) Assignee: XYGENYX INC., Pleasant Hill, CA (US)

( * ) Notice: Subject to any disclaimer, the term of this patent is extended or adjusted under 35 U.S.C. 154(b) by 280 days.

(21) Appl. No.: 18/411,771

(22) Filed: Jan. 12, 2024

(65) Prior Publication Data

US 2025/0228912 A1 Jul. 17, 2025

(51) Int. Cl.

| | |
|---|---|
| ***A61K 36/54*** | (2006.01) |
| ***A61K 31/164*** | (2006.01) |
| ***A61K 38/27*** | (2006.01) |
| ***A61K 38/30*** | (2006.01) |
| ***A61K 38/39*** | (2006.01) |

(52) U.S. Cl.
CPC ............ *A61K 36/54* (2013.01); *A61K 31/164* (2013.01); *A61K 38/27* (2013.01); *A61K 38/30* (2013.01); *A61K 38/39* (2013.01)

(58) Field of Classification Search
None
See application file for complete search history.

(56) References Cited

FOREIGN PATENT DOCUMENTS

JP 2004238310 A * 8/2004

* cited by examiner

*Primary Examiner* — Michael V Meller
(74) *Attorney, Agent, or Firm* — GALVIN PATENT LAW LLC; Brian R. Galvin

(57) ABSTRACT

A method and compositions of treatment for improving skin health and sleep quality using supplementation, comprising the step of applying a supplement formulation to a human subject via a selected administration route, the supplement formulation comprising therapeutically effective amounts of a hormone supplement, a plurality of collagen peptides, and a plurality of elastin peptides. The hormone supplement may comprise either HGH or IGF-1, or precursors or analogues thereof, and the collagen peptides may be sourced from a plurality of animal-based sources, which may include at least one of chicken bone, bovine hide, or fish tissues.

4 Claims, No Drawings

COMPOSITION AND METHODS OF TREATMENT FOR SKIN HEALTH AND SLEEP QUALITY USING SYNERGISTICALLY-ENHANCED SUPPLEMENTATION

CROSS REFERENCE TO RELATED APPLICATIONS

Priority is claimed in the application data sheet to the following patents or patent applications, each of which is expressly incorporated herein by reference in its entirety:

None

BACKGROUND OF THE INVENTION

Field of the Art

The disclosure relates to the field of supplementation therapies, and more particularly to the provision of a supplement formulation for treatment of humans with therapeutically-beneficial additional compounds.

Discussion of the State of the Art

As an individual ages, various hormone levels decrease and the ratio of certain hormones shifts over time, resulting in hormonal imbalances that create or aggravate conditions such as visible signs of aging in the skin (spots, wrinkles, etc) or alterations to mood or sleep quality. Endogenous (produced within the body) hormone levels may be supplemented with exogenous (from external sources) hormone supplementation, both by directly providing hormones that are deficient as well as by providing precursors, analogues, and other ingredients that help to stimulate more production of endogenous hormones such as Human Growth Hormone and IGF-1. Supplementation can be provided in the form of skin care products, due to the skin's ability to absorb substances that may be integrated both at the site of application as well as systemically throughout the body, and this opens the door to various combinations of ingredients that combine skin care benefits with hormone supplementation to alleviate the issues associated with hormone imbalances and age-related deficiencies.

Protecting the skin can help reduce the risk of long-term degenerative effects such as excessive dryness, skin cancer, hyperpigmentation, and age-related sign such as wrinkles or loss of skin firmness or texture. Many skincare products exist which attempt to address these concerns through topical applications of UV-blocking agents and oils, however they fail to address the underlying causes of these effects and merely treat the symptoms while attempting to prevent further damage. To adequately prevent and repair skin damage, a product needs to stop oxidative stress and glycation of the affected cells, and neutralize the products of these processes to prevent further damage.

In addition, there are multiple skin types that require different approaches as they differ in their reaction to environmental factors, absorption and permeability, and the rates and levels of these damaging processes and cellular products that must be addressed. To optimally protect and restore the skin, products must be tailored to individual with active melanogenesis or higher skin pigment production, those with little pigmentation, those with thicker or tougher skin that may be more difficult for compounds to adequately penetrate for absorption, and those with sensitive or delicate skin that is more easily damaged.

What is needed is a means of providing synergistically-enhanced supplementation, that uses combinations of active ingredients to improve the targeted benefits as well as penetration and absorption beyond those of single-ingredient supplements.

SUMMARY OF THE INVENTION

Accordingly, the inventors have conceived and reduced to practice a composition and methods of treatment using transdermal supplementation.

According to a preferred embodiment, a method of treatment for improving metabolic performance using supplementation, comprising the step of applying a supplement formulation to a human subject via a selected administration route, the supplement formulation comprising therapeutically effective amounts of a hormone supplement, a plurality of collagen peptides, and a plurality of elastin peptides. The hormone supplement may comprise either HGH or IGF-1, or precursors or analogues thereof, and the collagen peptides may be sourced from a plurality of animal-based sources, which may include at least one of chicken bone, bovine hide, or fish tissues.

According to another preferred embodiment, a composition for oral supplementation is disclosed, comprising an ingestible pill comprising, or capsule containing, therapeutically effective amounts of a hormone supplement, a plurality of collagen peptides, and a plurality of elastin peptides. The hormone supplement may comprise either HGH or IGF-1, or precursors or analogues thereof, and the collagen peptides may be sourced from a plurality of animal-based sources, which may include at least one of chicken bone, bovine hide, or fish tissues.

According to another preferred embodiment, a composition for transdermal supplementation is disclosed, comprising an aqueous gel with therapeutically effective amounts of a hormone supplement, a plurality of collagen peptides, and a plurality of elastin peptides. The hormone supplement may comprise either HGH or IGF-1, or precursors or analogues thereof, and the collagen peptides may be sourced from a plurality of animal-based sources, which may include at least one of chicken bone, bovine hide, or fish tissues.

DETAILED DESCRIPTION OF THE INVENTION

Headings of sections provided in this patent application and the title of this patent application are for convenience only and are not to be taken as limiting the disclosure in any way.

The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence. Techniques and mechanisms described or referenced herein will sometimes be described in singular form for clarity. However, it should be appreciated that particular aspects may include multiple iterations of a technique or multiple instantiations of a mechanism unless noted otherwise.

Human Growth Hormone

Human Growth Hormone (HGH), also known as somatotropin, is a hormone comprising a single-chain polypeptide of 191 amino acids that is synthesized in the pituitary gland and is present throughout the tissues of the body in varying concentrations. HGH stimulates growth and cell reproduction, as well as cell regeneration and the production of insulin-like growth factor 1 (IGF-1), which is a key hormone in regulating growth in children; it also has anabolic effects in adults and thus is commonly used in conjunction with anabolic steroids in stimulating muscle and bulk growth in athletes. HGH has a short biological half-life (of 10-20 minutes), and is therefore continuously synthesized in the human body as needed, regulated by a complex web of regulatory interactions between hormones and various metabolites. Somatropin is a recombinant analogue of HGH, which is available as a prescription drug to treat various growth hormone disorders. It is also used increasingly in vitality therapies for elderly patients, through off-label prescriptions. Similarly, somatropin has been used for decades by competitors in sports because of its anabolic properties.

Endogenous HGH production is primarily regulated by the hypothalamus, where growth hormone releasing hormone (GHRH, or somatocrinin) or growth hormone inhibiting hormone (GHIH, or somatostatin) are released by cells in response to a variety of factors including age, sex, diet, stress, and the balance of other hormones in the body. The ratio of GHRH to GHIH determines how much HGH is produced by the pituitary gland, with a predictable peak output occurring shortly after sleep begins (generally within minutes of the beginning of slow-wave stage III or IV sleep). Thus, application of supplementation formulations prior to sleep may be used to influence this peak HGH production through stimulation of additional endogenous HGH output as well as supplementation with exogenous HGH or analogues.

Insulin-Like Growth Factor 1

IGF-1, or somatomedin C, is another anabolic hormone, with a single-chain chemical structure of 70 amino acids similar to that of insulin. It is produced primarily in the liver, where the rate of synthesis is regulated by HGH levels. The rate of IGF-1 production can also be influenced by factors such as stress or diet (protein intake is known to increase IGF-1 production), and levels decrease with age. The relationship between HGH and IGF-1 production, and their respective roles in other tissues throughout the body, is known as the hypothalamic-pituitary-somatotropic axis; HGH is secreted by the pituitary gland which stimulates the secretion of IGF-1 by the liver, which in turn regulates many of the effects of HGH in other tissues such as muscle and bone growth. IGF-1 also directly affects the growth of most cell types in the body, and regulates DNA synthesis and cell division by signaling cells that sufficient nutrients are available to undergo the process. This signaling is also used to inhibit apoptosis (programmed cell death, part of the continuous recycling and regeneration processes ongoing within tissues) and increase the production of intracellular proteins. Increased IGF-1 levels are also positively correlated with a decreased risk of cardiovascular disease and ischemic stroke.

Cinnamaldehyde, the chemical structure of which is shown below, is the compound responsible for the distinctive odor in cinnamon. As an extract, it is a pale yellow viscous liquid with a strong flavor and aroma of cinnamon, and is used as a flavoring ingredient in many food products. When applied topically, cinnamaldehyde has also been shown to increase the phosphorylation levels of IGF-1 receptors in the skin, increasing IGF-1 signaling and thus stimulating endogenous collagen production in the skin. Common concentrations of cinnamaldehyde generally range from 9 to 5000 parts-per-million (ppm), both in ingested and topical uses.

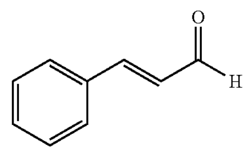

Collagen and Elastin

Collagen is the primary protein found in structures throughout the body including the extracellular matrix, and in total accounts for as much as 25-35% of the body's total protein composition. It is the key structural component of all connective tissues in the body, with a rigidity that varies according to the degree of mineralization of the collagen fibers; low-mineral-content fibers compose pliable tissues such as tendons, with increasing mineral content forming more rigid cartilage and bone tissues. It is also present in the dentin of teeth, vertebral discs of the spine, and other structures throughout the body. Unlike HGH and IGF-1, collagen has a triple-helix structure of three connected chains and is comparatively large with amino acid counts that may number in the thousands depending on the type and length of the collagen fibril. Intracellular collagen is one of the proteins that is regulated by IGF-1 levels, with increased IGF-1 stimulating more production of collagen; thus, hormone supplementation of HGH or IGF-1 directly increases collagen production throughout the body, which may be combined with exogenous collagen supplementation for even greater effect.

Collagen is directly related to skin health, with low collagen causing visible signs of aging such as wrinkles and skin spots, while high collagen gives the skin a more smooth and "plump" appearance by supporting and hydrating the tissues. In addition, collagen affects sleep quality due to its unusually-high glycine content (roughly one third of all amino acids present in the fibril), an amino acid that has been shown to directly improve sleep quality and duration. In turn, sleep quality affects skin health as the tissues are repaired throughout the night with the rate of regeneration being influenced by HGH secretion as described above.

There are 28 known types of collagen in the human body, with over 90% being type I; this form of collagen is present throughout bone, skin, organ structures, tendons, and vascular structures such as artery walls. Type XI collagen is another important variant, which forms a matrix with types I and II within tendons and cartilage to stabilize the molecular structure by regulating the distance between the type I and II fibrils. With decreased type XI collagen, tendons weaken and cartilage stiffens, inhibiting joint mobility and muscle performance. Supplementation of collagen may target specific variant types to achieve a desired effect, by collagen sourced from specific ingredients with desirable proportions of specific types; for example, chicken bones are rich in types I, II, and XI collagen as well as vitamins and minerals that aid in the bioavailability of the collagen peptides and the repair of tissues. Bovine collagen is rich in hydroxyproline, a key constituent of endogenous collagen production that enhances skin health by increasing mitochondrial activity within skin cells by as much as 13%, stimulating repair and regeneration processes to reduce signs of aging and repair damage caused by UV exposure and stress. In addition, a peptide called decorin may be found in collagen sourced from fish, which assists the transmission of IGF-1 signaling to improve the production of endogenous collagen and stimulate cellular processes as described above.

Elastin is another protein found throughout connective tissues, and is responsible for providing elastic behavior for tissues to return to their original shape when deformed; a visible example of this is the skin returning to its normal shape when pinched. It is also a key component in the circulatory system where it maintains blood vessel elasticity, and in ligaments and cartilage where it enables the tissues to deform during movement and return to their original shape without damage. Supplementation with elastin works together with collagen to synergistically improve the health and appearance of the skin by strengthening the tissues and maintaining their elasticity; elastin supports skin health and reduces the visible signs of aging by keeping the skin pliable, reducing the appearance of wrinkles associated with skin that has permanently deformed and no longer returns to its original smooth surface.

One issue with hormone and collagen supplementation is that of absorption; large molecules are poorly absorbed due to their size, resulting in low bioavailability and necessitating increased dosages in a supplement formulation. To counteract this, large peptides may be broken up into smaller chains that are more readily absorbed, whereupon they may be reassembled in the body to form the larger molecules as needed. Taking this principle further, these large molecules may be broken up into nano-scale constituents that have high bioavailability due to their much lower molecular size, and are then used by the body to produce larger peptide chains where they are needed. Combining supplementation of HGH or IGF-1 with these nano-ized collagen peptides produces a synergistic formulation that provides both the ingredients for collagen fibrils of various types, along with the signaling agents that trigger increased collagen production from the constituent peptides provided.

Additional Ingredients and Formulations

Theanine, the chemical structure of which is shown below, is an amino acid that is commonly found in tea leaves, particularly green tea. It has been studied for its potential neurological benefits, including its ability to promote relaxation and reduce anxiety without causing drowsiness. Theanine works by increasing levels of GABA, a neurotransmitter that has calming effects on the brain. One of the most well-known benefits of theanine is its ability to reduce stress and anxiety. Studies have found that theanine may help to lower heart rate and blood pressure, which are both markers of stress. It may also improve cognitive function and mood, potentially by increasing levels of other neurotransmitters such as dopamine and serotonin. Another potential benefit of theanine is its ability to improve sleep quality. Research has found that theanine may increase the amount of deep sleep and improve overall sleep efficiency. This may make it beneficial for people with sleep disorders or those who have difficulty falling asleep or staying asleep. Theanine is generally considered safe and well-tolerated at doses of up to 400 mg per day.

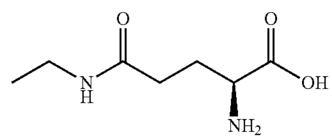

*Mucuna pruriens*, commonly called velvet bean or monkey tamarind, is a legume native to tropical regions of Africa and Asia. It has been used for centuries in Ayurvedic medicine for the treatment of various diseases, including neurological disorders. The active ingredients in *Mucuna pruriens* include L-DOPA (L-3,4-dihydroxyphenylalanine), serotonin, 5-HTP (5-hydroxytryptophan), and a variety of other minor constituents.

L-DOPA (L-3,4-dihydroxyphenylalanine), the chemical structure of which is shown below, is the most studied and widely recognized active ingredient in *Mucuna pruriens*, and it has been found to have potent neuroprotective and neurorestorative effects and is commonly used in treatment of Parkinson's Disease and other neurodegenerative illnesses. L-DOPA is a precursor to dopamine, a neurotransmitter that plays a crucial role in regulating mood, motivation, and movement. *Mucuna pruriens* supplementation has been found to increase dopamine levels in the brain, which can improve motor function and reduce symptoms of Parkinson's disease. In addition, L-DOPA has been shown to protect against neurotoxicity induced by oxidative stress, which can cause neurodegenerative diseases such as Alzheimer's disease. Typical dose concentrations of L-DOPA can range from 100-800 mg per day, depending on the formulation used. The medication is often combined with other drugs, such as carbidopa, which helps to prevent the breakdown of L-DOPA in the body and increases its effectiveness.

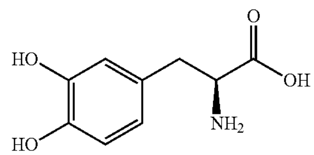 [SMILES: N[C@@H](Cc1ccc(O)c(O)c1)C(=O)O]

Serotonin and 5-HTP, the structure of each of which is shown and labeled below, are also found in *Mucuna pruriens*, and they have been found to have mood-enhancing and anti-depressive effects. Serotonin is a neurotransmitter that regulates mood, sleep, and appetite, and low levels of serotonin have been linked to depression and anxiety. 5-HTP is a precursor to serotonin, and supplementation with 5-HTP has been found to increase serotonin levels in the brain, which can improve mood and reduce symptoms of depression. The concentration of serotonin in the brain can be influenced by medications such as selective serotonin reuptake inhibitors (SSRIs) and monoamine oxidase inhibitors (MAOIs). These drugs work by increasing the availability of serotonin in the synaptic cleft, allowing it to bind to and activate postsynaptic receptors. The appropriate dosage of SSRIs or MAOIs will depend on the specific medication, the patient's age, weight, and overall health, and the severity of their symptoms. Generally, a starting dose of an SSRI may range from 10-20 mg per day, with the dose gradually increased over several weeks as tolerated. The appropriate dosage of 5-HTP will depend on the reason for its use, but typical doses range from 50-400 mg per day.

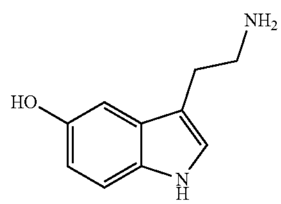

Seratonin

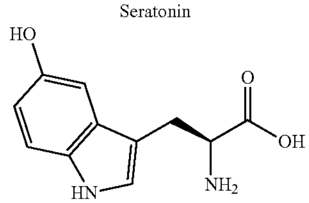

5-HTP

Other minor constituents in *Mucuna pruriens* include alkaloids, saponins, and flavonoids, which have been found to have antioxidant and anti-inflammatory effects. These compounds may help to protect the brain from oxidative stress and inflammation, which are believed to play a role in the development of neurodegenerative diseases.

Beta-hydroxybutyric acid (BHBA), the chemical structure of which is shown below, is an organic acid whose deprotonated form (beta-hydroxybutyrate, or BHB) is a ketone body produced by the liver from fatty acids during periods of fasting, low-carbohydrate diets, or prolonged exercise. BHB (among other ketones) is used by the body as an alternative fuel source to glucose, particularly by the brain and heart, and has been associated with a number of health benefits. One of the primary benefits of BHB is its ability to promote weight loss and improve metabolic health. BHB has been shown to increase energy expenditure, reduce appetite, and improve insulin sensitivity, all of which can contribute to weight loss and improved metabolic health. BHB has also been shown to have anti-inflammatory and antioxidant effects. Inflammation is a key contributor to a wide range of chronic diseases, including heart disease, diabetes, and cancer, and reducing inflammation can help to prevent or manage these conditions. In particular, BHB and other ketones contribute to reduced tumor growth as tumors are known to “feed” on glucose and when the body is in a state of ketosis blood glucose levels are extremely low as the body burns ketone bodies for fuel instead. BHB has been shown to reduce inflammation by inhibiting the activity of certain inflammatory proteins in the body, and may also help to reduce oxidative stress by increasing the production of certain antioxidant enzymes. BHB may have neuroprotective effects. Research has suggested that BHB may improve cognitive function and protect against neurological diseases such as Alzheimer’s and Parkinson’s disease. BHB has been shown to increase the production of certain proteins that protect against neurological damage, and may also help to improve the function of mitochondria, which are the energy-producing organelles within cells. BHB may also have potential benefits for athletic performance. BHB has been shown to increase endurance and reduce fatigue during prolonged exercise, potentially by providing an alternative fuel source to glucose and sparing muscle glycogen stores. The optimal dosage of BHB depends on a variety of factors, including body weight, activity level, and overall health. BHB supplements are typically available in powder or capsule form, and dosages may range from 6-12 grams per day.

BHB salts may be formed by the neutralization of BHBA, resulting in a BHB salt cation with a metal ion taking the place of the hydrogen in the hydroxyl group; common BHB salts include sodium BHB, potassium BHB, calcium BHB, and magnesium BHB. These various salts and esters may be combined to produce a mixed ketogenic composition, with differing ratios of multiple forms of BHB to achieve a desired effect or to maximize any synergistic benefits of other ingredients in the formulation or taken separately; depending on the particular formulation, concentration of any one BHB salt may range from 10% to as high as 40%.

Sodium BHB is a form of ketone salt that combines BHB with sodium, a mineral that is important for fluid balance, nerve function, and muscle contraction. Sodium BHB may help to increase energy levels, reduce inflammation, and improve cognitive function, particularly in individuals with neurological disorders such as Alzheimer’s disease. Potassium BHB is a form of ketone salt that combines BHB with potassium, a mineral that is important for fluid balance, muscle function, and blood pressure regulation. Potassium BHB may help to improve athletic performance, increase energy levels, and reduce inflammation. Calcium BHB is a form of ketone salt that combines BHB with calcium, a mineral that is important for bone health and muscle function. Some studies have suggested that calcium BHB may help to improve athletic performance, increase energy levels, and reduce inflammation. Magnesium BHB is a form of ketone salt that combines BHB with magnesium, a mineral that is important for muscle function, nerve function, and bone health. Magnesium BHB may help to improve sleep quality, reduce inflammation, and improve cardiovascular health. In addition to these common BHB salts, BHB may form a conjugate base with transition metals or amino acids, or it may form an ester with other organic functional groups such as alkyl, alkenyl, acyl, aryl, or other organyls.

Both BHB and cetylated fatty acids have been studied for their potential anti-inflammatory effects. BHB has been shown to suppress inflammation by inhibiting the NLRP3 inflammasome, while cetylated fatty acids have been shown to inhibit the production of inflammatory cytokines. Combining these two compounds may have a synergistic effect on reducing inflammation in the body. This combination may be particularly beneficial for individuals with chronic inflammatory conditions such as arthritis, as well as athletes looking to reduce inflammation and improve exercise recovery. When combined with BHB or BHBA, caprylic acid may help to increase ketone levels in the body and improve energy metabolism, which could have potential benefits for conditions such as epilepsy, neurodegenerative diseases, and metabolic disorders. When combined with BHB or BHBA, zeatin may help to further boost the antioxidant and anti-inflammatory properties of ketones, which could have potential benefits for conditions such as Alzheimer’s disease, Parkinson’s disease, and cancer. Additionally, combining caprylic acid or zeatin with various BHB salts, such as sodium, potassium, or calcium BHB, may help to improve the bioavailability and absorption of these compounds in the body, as well as enhance their effects on energy metabolism and cellular signaling pathways.

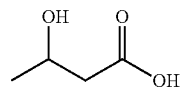

Caprylic acid (also known as octanoic acid), the chemical structure of which is shown below, is a type of medium-chain fatty acid (MCFA) that is naturally found in various sources such as coconut oil, palm kernel oil, and dairy products. It is a saturated fatty acid that contains eight carbon atoms and has been studied for its potential health benefits. One of its main benefits is its ability to support healthy digestion. Caprylic acid has been shown to have antimicrobial properties, which means that it can help to reduce the growth of harmful bacteria, viruses, and fungi in the gut. This can be particularly helpful for people who suffer from digestive issues such as *candida* overgrowth, small intestine bacterial overgrowth (SIBO), and irritable bowel syndrome (IBS). By reducing the overgrowth of harmful microorganisms, caprylic acid can help to restore a healthy balance of gut bacteria and support optimal digestive function. Another potential health benefit of caprylic acid is its ability to support brain health. The brain is primarily composed of fatty acids, and studies have shown that caprylic acid may have neuroprotective effects. It has been suggested that caprylic acid can improve cognitive function and memory, as well as help to prevent neurodegenerative diseases such as Alzheimer's and Parkinson's. This may be due to caprylic acid's ability to increase the production of ketones, which are a type of fuel that the brain can use when glucose is in short supply. In addition to its effects on digestion and brain health, caprylic acid may also have potential benefits for weight loss. It is quickly absorbed and metabolized by the liver, which means it can provide a quick source of energy and may help to increase metabolic rate. Caprylic acid has also been shown to help reduce hunger and increase feelings of fullness, which can help to reduce overall calorie intake and support weight loss efforts. Caprylic acid has also been studied for its potential antimicrobial effects on the skin. It has been shown to have activity against several strains of bacteria that are associated with skin infections, such as *Staphylococcus aureus*. Caprylic acid may be useful for treating conditions such as acne, eczema, and dermatitis. Finally, caprylic acid has potential benefits for oral health. It has been shown to have antibacterial properties that may help to reduce the growth of harmful bacteria in the mouth, which can lead to improved oral hygiene and a reduced risk of cavities and gum disease. Dosage may vary according to a desired effect or formulation combined with other ingredients, but common doses of caprylic acid range up to 2 grams per day taken in divided doses with food.

Combining caprylic acid with CBD (which is described in detail below) may enhance the absorption and bioavailability of CBD, as medium-chain fatty acids such as caprylic acid can improve the solubility of CBD. One potential benefit of combining CBD and caprylic acid is the potential to support healthy brain function. CBD has been studied for its potential neuroprotective effects, which may help to protect neurons from damage or degeneration. Additionally, caprylic acid is metabolized into ketones in the body, which can serve as an alternative fuel source for the brain. This may help to support healthy brain function and improve cognitive performance. Another potential benefit of combining CBD and caprylic acid is the potential to support healthy digestion. Caprylic acid has been shown to have antimicrobial properties, which may help to reduce harmful bacteria in the gut and promote healthy digestion. Additionally, CBD has been studied for its potential anti-inflammatory effects, which may help to reduce inflammation in the gut and support overall digestive health. Combined supplementation with CBD and caprylic acid may also have potential benefits for weight management. Caprylic acid has been shown to have potential thermogenic effects, which may help to promote fat burning and support healthy weight management. Additionally, CBD has been studied for its potential effects on appetite regulation, which may help to reduce food intake and support healthy weight management.

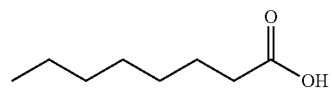

L-BAIBA (L-beta-aminoisobutyric acid), the chemical structure of which is shown below, is a naturally occurring amino acid that has gained attention in recent years for its potential health benefits. L-BAIBA is produced in response to exercise and has been shown to have a number of positive effects on metabolism, energy expenditure, and overall health. One of the main health benefits of L-BAIBA is its ability to increase energy expenditure and promote fat burning. Studies have shown that L-BAIBA can activate brown adipose tissue, which is a type of fat that generates heat and burns calories. By increasing the activity of brown fat, L-BAIBA can help to boost metabolism and increase the number of calories burned, even at rest. Another potential benefit of L-BAIBA is its ability to improve insulin sensitivity and glucose metabolism. Insulin resistance is a major risk factor for type 2 diabetes and other metabolic disorders. Studies have shown that L-BAIBA can improve insulin sensitivity and glucose uptake in skeletal muscle cells, which may help to prevent the development of insulin resistance and type 2 diabetes. L-BAIBA has also been shown to have anti-inflammatory effects, which may help to reduce the risk of chronic diseases such as heart disease and cancer. Inflammation is a common underlying factor in many chronic diseases, and reducing inflammation in the body can help to promote overall health and longevity. In addition to its effects on metabolism and inflammation, L-BAIBA may also have potential benefits for brain health. Studies have shown that L-BAIBA can improve cognitive function and memory in mice, and may have neuroprotective effects that could help to prevent or slow the progression of neurodegenerative diseases such as Alzheimer's. Dosages may vary but in studies using mice tolerated dose ranges from 10-100 mg/kg of bodyweight, and human trials have used doses of up to 1 gram per day.

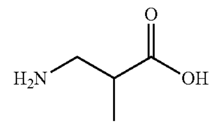

L-carnitine fumarate, the chemical structure of which is shown below, is a specific form of L-carnitine that is bound to fumaric acid, a compound that is involved in the energy production process in cells. The addition of fumaric acid to L-carnitine in the form of L-carnitine fumarate is thought to enhance the stability and bioavailability of the amino acid, making it more easily absorbed by the body. Fumaric acid is also believed to have antioxidant properties, which may further support the health benefits of L-carnitine fumarate. Moreover, L-carnitine fumarate is believed to be more stable than other forms of L-carnitine, making it a preferred choice for supplements. Stability is important because it allows for the preservation of the active ingredient, which ensures that the supplement retains its potency for a longer period of time. While the body can convert regular L-carnitine into L-carnitine fumarate, consuming L-carnitine fumarate directly may provide a more efficient means of obtaining the amino acid and the benefits associated with it.

L-carnitine fumarate has been studied for its potential benefits in improving athletic performance, supporting weight loss, and promoting heart health, among other uses. L-carnitine is involved in the metabolism of fatty acids, and is necessary for the transport of long-chain fatty acids into the mitochondria of cells, where they can be used as a source of energy. L-carnitine fumarate has been shown to have several potential health benefits, including improved athletic performance, weight loss, and heart health. One of the main benefits of L-carnitine fumarate is its ability to improve athletic performance. L-carnitine is involved in the metabolism of fatty acids, which are an important source of energy during exercise. Studies have shown that L-carnitine supplementation can improve exercise performance, reduce muscle damage, and delay fatigue in both athletes and non-athletes. L-carnitine fumarate is a stable form of L-carnitine that is easily absorbed by the body and has been shown to have similar benefits to other forms of L-carnitine. L-carnitine fumarate may also have potential benefits for weight loss. Some studies have shown that L-carnitine supplementation can increase fat burning and reduce body fat in overweight individuals. However, the evidence for these effects is mixed, and more research is needed to fully understand the role of L-carnitine in weight loss. Another potential benefit of L-carnitine fumarate is its ability to support heart health. L-carnitine is involved in the transport of fatty acids into the mitochondria of cells, where they can be used as a source of energy. This process is particularly important for the heart, which relies heavily on fatty acid metabolism for energy. Studies have shown that L-carnitine supplementation can improve heart function in individuals with heart failure, and may also help to reduce the risk of heart disease in healthy individuals. Common dosage ranges from 500 to 2000 mg per day, however this may vary and higher and lower doses may be used according to a particular formulation or desired effect.

5-MTHF (described below) and L-carnitine fumarate both play important roles in energy metabolism. 5-MTHF is involved in the methylation cycle, which is essential for the production of ATP (the body's primary source of energy), while L-carnitine fumarate is involved in transporting fatty acids into the mitochondria, where they can be burned for energy. Combining these two compounds may help to enhance energy production and reduce fatigue. This combination may be particularly beneficial for individuals with chronic fatigue syndrome, as well as athletes looking to improve endurance and performance.

combination of CBD and l-carnitine fumarate has been shown to have numerous positive effects on overall health and wellness. L-carnitine plays a crucial role in energy metabolism and is involved in the transportation of fatty acids into mitochondria, where they are used for energy production. CBD, on the other hand, has potential anti-inflammatory effects and has been shown to positively impact various bodily functions. When combined, these supplements work together to provide several benefits. One of the most notable benefits of this combination is its ability to support healthy energy levels. L-carnitine helps to transport fatty acids, which are essential for energy production, while CBD's anti-inflammatory effects reduce inflammation and promote healthy energy levels. Additionally, the combination has been shown to support healthy weight management by promoting fat burning and regulating appetite. Moreover, CBD and l-carnitine fumarate supplementation can improve muscle recovery and overall exercise performance. L-carnitine has been studied for its potential effects on muscle recovery, and when combined with CBD's anti-inflammatory effects, it can significantly reduce inflammation and promote quick muscle recovery.

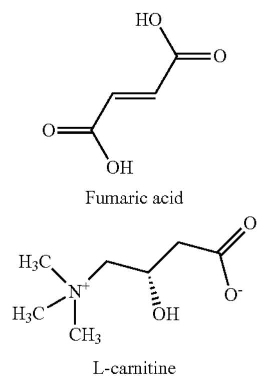

Fumaric acid

L-carnitine

Cetylated fatty acids are a group of compounds derived from fatty acids modified by the addition of a cetyl group. This group of compounds includes various esters of cetyl myristoleate and other cetyl esters that have been modified to enhance their therapeutic potential. These compounds are often marketed as dietary supplements or topical treatments for a wide range of health conditions. One potential benefit of cetylating a fatty acid is increased stability. Fatty acids are often unstable and prone to oxidation, which can reduce their effectiveness and cause them to go rancid over time. Cetylating a fatty acid can improve its stability and extend its shelf life, making it a more effective and reliable treatment option. Another potential benefit of cetylating a fatty acid is improved solubility. Many fatty acids are poorly soluble in water and other body fluids, which can limit their ability to reach and interact with target tissues. Cetylating a fatty acid can increase its solubility, allowing it to more easily dissolve in body fluids and reach its intended target. Cetylating a fatty acid can also enhance its bioavailability, or the degree to which it is absorbed and used by the body. Some fatty acids are poorly absorbed by the body, which can limit their effectiveness. Cetylating a fatty acid can improve its ability to cross cellular membranes and be absorbed into the bloodstream, increasing its bioavailability and enhancing its therapeutic potential. Finally, cetylating a fatty acid can increase its tissue penetration, allowing it to more effectively target and interact with specific tissues or organs. This can be particularly useful for fatty acids that have specific therapeutic benefits, such as reducing inflammation in the joints or improving brain function.

Combining CBD with cetylated fatty acids (CFA) has been shown to have several positive effects on overall health and wellness. Cetylated fatty acids are fatty acids that have been combined with cetyl alcohol to form cetylated fatty acid esters, which have been demonstrated to have potent anti-inflammatory effects. CBD, on the other hand, has been studied for its ability to reduce inflammation and promote healthy immune function, and has been shown to have positive impacts on various bodily functions. Together, these supplements have synergistic effects and work together to provide several definitive benefits. Combining CBD with CFA has been shown to significantly reduce inflammation throughout the body, contributing to overall health and wellness. CFA has been demonstrated to have potent anti-inflammatory effects, while CBD has been shown to have anti-inflammatory and immunomodulatory properties. Together, they have a powerful impact on reducing inflammation, which can improve various health conditions. Additionally, combining CBD with CFA has been shown to reduce joint pain and support joint health. CFA has been studied for its potential to improve joint mobility and reduce joint pain, while CBD has been shown to have potential analgesic effects and may reduce pain and discomfort in the joints. Together, they work to improve joint health and reduce pain and discomfort associated with joint inflammation. Furthermore, the combination of CBD with CFA has been shown to have potential benefits for overall skin health. CFA has been demonstrated to improve skin hydration and reduce the appearance of wrinkles and fine lines. Similarly, CBD has been shown to have anti-inflammatory and anti-oxidant effects on the skin, which can reduce skin inflammation and promote healthy skin. Together, they improve overall skin health and promote a more youthful appearance.

One of the most commonly used cetylated fatty acids is cetyl myristoleate (the chemical structure of which is shown below), which is believed to have anti-inflammatory properties. It is thought to work by inhibiting the production of certain enzymes that are involved in inflammation. This can help reduce pain and stiffness in joints, making it a popular supplement among individuals with arthritis or other inflammatory joint conditions. Another cetylated fatty acid that has gained popularity is cetyl palmitate, which is used in topical creams and lotions to moisturize and soothe dry, irritated skin. Cetylated fatty acids have been studied for their potential health benefits in a number of different contexts. In addition to their anti-inflammatory effects, these compounds are believed to have other properties that may support overall health and wellbeing. For example, some studies have suggested that cetylated fatty acids may help improve mobility and reduce pain in individuals with osteoarthritis. In one study, participants with knee osteoarthritis who took a cetylated fatty acid supplement experienced significant improvements in pain, stiffness, and physical function compared to those who received a placebo. Other studies have suggested that cetylated fatty acids may help reduce inflammation and pain in other parts of the body, such as the back and neck. Cetylated fatty acids have also been studied for their potential effects on immune function. Some research has suggested that these compounds may help boost the immune system by increasing the production of certain types of white blood cells. This could make them useful for supporting overall immune health, as well as for preventing and treating infections. In addition, cetylated fatty acids may have potential benefits for skin health. As mentioned earlier, cetyl palmitate is often used in topical creams and lotions to moisturize and soothe dry, irritated skin. Other cetylated fatty acids may also have similar effects on the skin, helping to reduce redness, inflammation, and other signs of irritation.

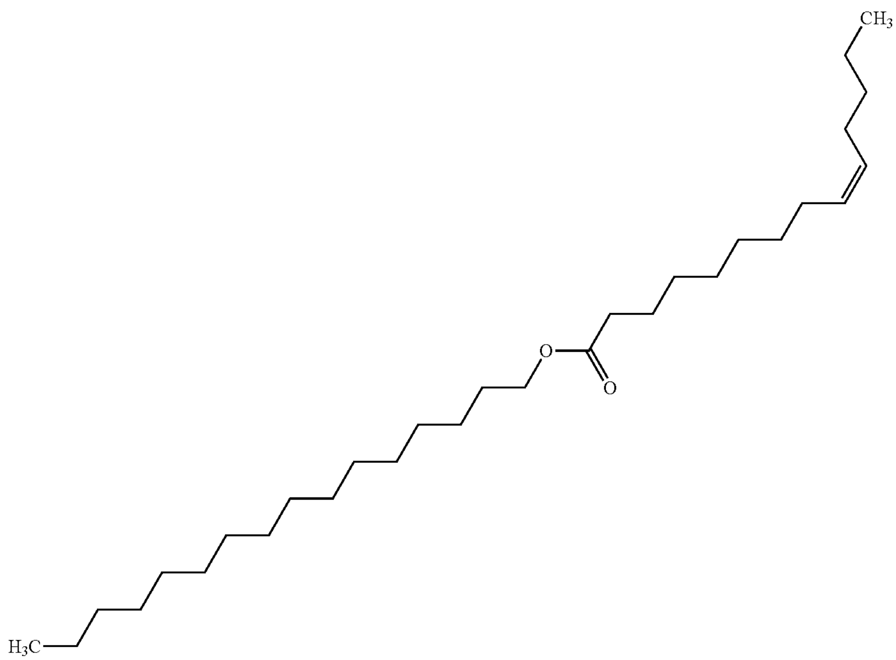 [SMILES: CCCC/C=C\CCCCCCCC(=O)OCCCCCCCCCCCCCCCC]

Zeatin, the chemical structure of which is shown below, is a plant growth hormone that is naturally produced in various plants, including corn, rice, and wheat. It has been studied for its potential health benefits, including anti-aging and skin rejuvenation properties. One of the main benefits of zeatin is its ability to stimulate cell growth and division. This is important for skin health and anti-aging, as the growth and division of skin cells slows down with age. Zeatin has been shown to promote cell growth and proliferation, which can help to improve the appearance of fine lines and wrinkles, and enhance skin elasticity and firmness. Zeatin has also been studied for its antioxidant properties. It has been shown to scavenge free radicals, which are unstable molecules that can damage cells and contribute to aging and disease. By neutralizing free radicals, zeatin may help to protect against oxidative stress and prevent cellular damage. Another potential benefit of zeatin is its ability to regulate inflammation. Inflammation is a natural response to injury or infection, but chronic inflammation can contribute to a range of diseases, including heart disease, diabetes, and cancer. Zeatin has been shown to have anti-inflammatory effects, which may help to reduce the risk of these diseases. Zeatin has also been studied for its potential to promote wound healing. It has been shown to stimulate the production of collagen, a protein that is important for skin elasticity and wound healing. By promoting collagen production, zeatin may help to speed up the healing process and reduce the risk of scarring. While no formal recommended dose has yet been established, various trials and studies have used doses ranging from 0.1 to 1 mg/kg of bodyweight and the specific dose used in a formulation may vary according to other ingredients or a desired result.

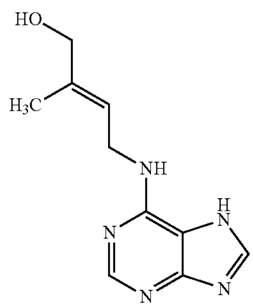 [SMILES: C/C(=C\CNc1ncnc2nc[nH]c12)CO]

Carotenoids are a class of organic pigments that are widely distributed in nature, occurring in fruits, vegetables, and other plant-based foods. They are responsible for the red, orange, and yellow colors found in many fruits and vegetables. There are over 600 different carotenoids, but only about 50 are found in the human diet, and of those, only a few are converted to vitamin A. Carotenoids are divided into two main groups: carotenes and xanthophylls. Carotenes are hydrocarbons that are lipid-soluble, while xanthophylls contain oxygen and are more polar, making them water-soluble. The most well-known carotenoid is beta-carotene, which is converted to vitamin A in the body. One of the main health benefits of carotenoids is their antioxidant properties. They act as free radical scavengers, neutralizing harmful molecules that can damage cells and contribute to the development of chronic diseases such as cancer, heart disease, and Alzheimer's disease. In addition to their anti-oxidant properties, carotenoids have been shown to have anti-inflammatory effects, which can help reduce the risk of chronic diseases. Carotenoids also play an important role in eye health. Specifically, the carotenoids lutein and zeaxanthin accumulate in the macula of the eye, where they protect against damage from blue light and oxidative stress. Studies have shown that a diet rich in lutein and zeaxanthin can help reduce the risk of age-related macular degeneration, a leading cause of blindness in older adults. Other health benefits of carotenoids include their role in immune function and skin health. Beta-carotene, for example, has been shown to enhance immune function by increasing the production of white blood cells. Carotenoids may also help protect the skin from damage caused by UV radiation, which can contribute to premature aging and skin cancer. The best dietary sources of carotenoids include carrots, sweet potatoes, spinach, kale, tomatoes, bell peppers, and mangoes, and absorption can be improved if they are consumed alongside healthy fats such as olive oil or avocado.

Lutein, the chemical structure of which is shown and labeled below, Lutein is a carotenoid that accumulates in the macula of the eye and is known for its protective effects against blue light and oxidative stress. However, recent studies have also shown that lutein supplementation may have cognitive and neurological benefits as well. Studies have found that lutein supplementation improved cognitive function in healthy young adults. Participants who took lutein supplements showed improvements in memory, processing speed, and other cognitive measures compared to those who received a placebo. Another study found that lutein supplementation improved spatial working memory in older adults with mild cognitive impairment. Participants who received lutein supplements showed significant improvements in memory compared to those who received a placebo. Lutein has also been studied for its potential neuroprotective effects. One study (Renzi L M, Dengler M J, Puente A, Miller L S, Hammond B R Jr. *Relationships between macular pigment optical density and cognitive function in unimpaired and mildly cognitively impaired older adults*. Neurobiol Aging. 2014 July; 35(7):1695-9. doi: 10.1016/j.neurobiolaging.2013.12.024. Epub 2013 Dec. 27. PMID: 24508218) found that lutein supplementation reduced inflammation and improved cognitive function in older adults with mild cognitive impairment. Participants who took lutein supplements showed improvements in memory and attention compared to those who received a placebo. The doses used in these studies varied, but most used a daily dose of 10-20 mg of lutein. Nutritional supplements often use similar doses, ranging from as low as 2 mg to as high as 25 mg or more according to a desired effect or the inclusion of additional ingredients such as zeaxanthin.

Zeaxanthin, the chemical structure of which is shown and labeled below, is a carotenoid that is similar in structure to lutein and is also found in high concentrations in the macula of the eye. Like lutein, zeaxanthin is known for its protective effects against blue light and oxidative stress. However, recent research has also suggested that zeaxanthin may have cognitive and neurological benefits. One study (Johnson E J, McDonald K, Caldarella S M, Chung H Y, Troen A M, Snodderly D M. *Cognitive findings of an exploratory trial of docosahexaenoic acid and lutein supplementation in older women*. Nutr Neurosci. 2008 April; 11(2):75-83. doi: 10.1179/147683008X301450. PMID: 18510807) found that supplementation with zeaxanthin, along with other nutrients such as omega-3 fatty acids, improved cognitive function in individuals with mild cognitive impairment. Participants who received the supplement for six months showed significant improvements in memory and attention compared to those who received a placebo. Other studies have found that supplementation with zeaxanthin improved cognitive flexibility and processing speed in healthy young adults, that supplementation with zeaxanthin reduced the risk of stroke in older adults, and that zeaxanthin reduced inflammation and oxidative stress in the brains of mice with Alzheimer's disease. The doses used in these studies varied, but most used a daily dose of 2-20 mg of zeaxanthin.

Meso-zeaxanthin, the chemical structure of which is shown and labeled below, is a carotenoid that is structurally similar to lutein and zeaxanthin and is also found in high concentrations in the macula of the eye. Like other carotenoids, meso-zeaxanthin is known for its antioxidant and anti-inflammatory properties, which protect against oxidative stress and inflammation. Recent studies have suggested that meso-zeaxanthin may have specific benefits for eye health, including improving visual acuity and contrast sensitivity, reducing glare, and protecting against age-related macular degeneration. One of the unique properties of meso-zeaxanthin is its ability to form a complex with lutein and zeaxanthin, which is called the macular pigment. The macular pigment acts as a blue light filter, protecting the retina from damage caused by blue light exposure. Meso-zeaxanthin is thought to be particularly effective at absorbing blue light, which may explain its specific benefits for visual performance and macular health. While research on meso-zeaxanthin is still limited compared to lutein and zeaxanthin, early studies have suggested that supplementation with meso-zeaxanthin may be beneficial for improving visual performance, reducing the risk of age-related macular degeneration, and protecting against oxidative stress and inflammation.

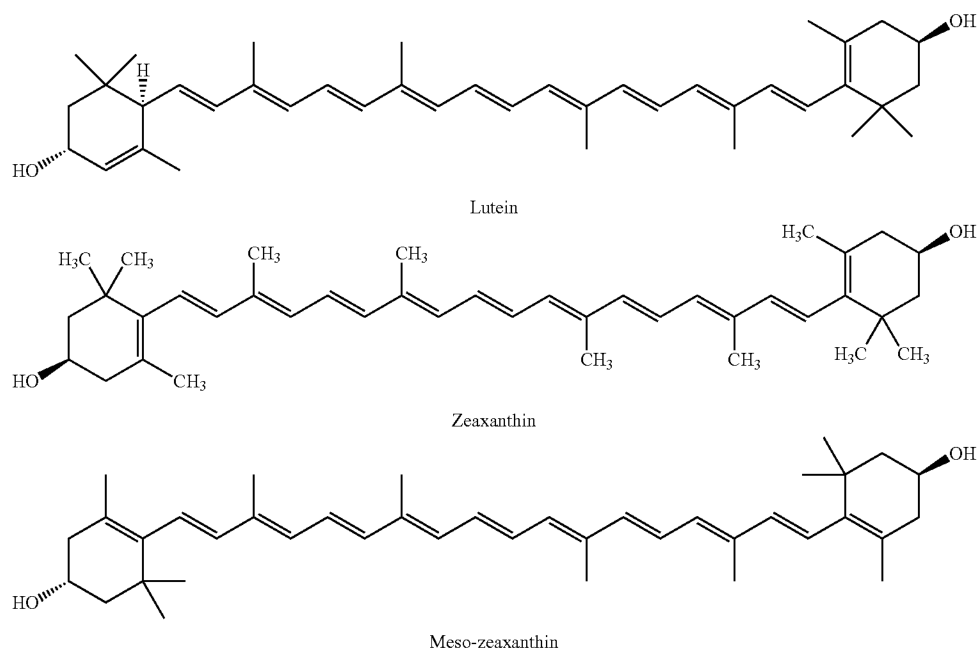

Lutein

Zeaxanthin

Meso-zeaxanthin

Probiotic supplements are dietary supplements that contain live microorganisms, such as bacteria and yeast, that are intended to have beneficial effects on the body, particularly the digestive system. The goal of probiotics is to introduce “good” bacteria to the gut, which can help to balance the microbiome and support healthy digestion and immune function. Probiotics work by colonizing the gut and competing with harmful bacteria for resources. They also help to produce substances that can improve gut health, such as short-chain fatty acids and bacteriocins. In addition, probiotics can stimulate the immune system, which can help to protect against infections and disease.

There are many different strains of bacteria and yeast that can be used in probiotic supplements, each with its own unique benefits. *Lactobacillus acidophilus* is a type of bacteria that is naturally found in the human gut and is known for its ability to produce lactic acid, which can help to improve gut health. *Bifidobacterium bifidum* is another type of bacteria that is naturally found in the human gut and is known for its ability to break down complex carbohydrates and produce substances that can improve gut health. *Saccharomyces boulardii* is a type of yeast that is known for its ability to help prevent and treat diarrhea caused by antibiotics or infections. *Streptococcus thermophilus* is a type of bacteria that is commonly used in the production of yogurt and is known for its ability to improve lactose digestion and support immune function. The dosage of probiotic supplements can vary depending on the specific product and the intended use. Most supplements contain anywhere from 1 billion to 100 billion colony-forming units (CFUs) per dose, with higher doses typically used for more severe digestive issues. In addition to supplements, probiotics can also be obtained from fermented foods, such as yogurt, kefir, sauerkraut, and kimchi. These foods contain live cultures of beneficial bacteria and can provide similar health benefits as probiotic supplements.

Cannabinoids, such as THC and CBD, interact with the endocannabinoid system in the body, which is involved in regulating various physiological processes, including inflammation and immune function. These compounds interact with the endocannabinoid system (ECS), a complex network of receptors and neurotransmitters found throughout the body, including in the gut where it plays a role in regulating digestion and maintaining gut health. Probiotics work by introducing beneficial bacteria to the gut, which can help to balance the microbiome and support healthy digestion and immune function. Some studies have suggested that the use of cannabinoids may also have a beneficial effect on gut microbiota, potentially by reducing inflammation and oxidative stress. There is evidence to suggest that the endocannabinoid system and gut microbiome are closely linked, with the gut microbiome playing a role in regulating endocannabinoid signaling. In one study, researchers found that mice treated with antibiotics had lower levels of endocannabinoids and reduced gut motility, suggesting that the gut microbiome plays a role in regulating endocannabinoid signaling and gut function. Other studies have suggested that the use of cannabinoids may have a beneficial effect on the gut microbiome, potentially by reducing inflammation and oxidative stress. Studies have shown that the ECS is involved in regulating the balance of microorganisms in the gut microbiome. Specifically, cannabinoid receptors are found on the cells lining the gut, as well as on immune cells and other cells in the gut. Activation of these receptors by cannabinoids can lead to changes in the gut microbiome. One study found that THC and CBD both had the ability to modulate the gut microbiome, leading to changes in the levels of specific bacteria in the gut by reducing the production of inflammatory cytokines in the gut and improving the diversity of gut microbiota in mice with colitis. This demonstrates that the combination of probiotics and cannabinoids may have synergistic effects on gut health.

In addition to probiotic supplementation that directly introduces microbiota to the gut biome, prebiotic supplementation may also be used wherein compounds are introduced to encourage the growth of existing gut flora. Prebiotics commonly involve a type of dietary fiber that are not digested by the human body, but instead are fermented by bacteria in the gut. This fermentation process produces short-chain fatty acids, which are a source of energy for the cells in the colon, and also help to support the growth of beneficial bacteria. Polyphenols can act as prebiotics by promoting the growth of specific strains of beneficial bacteria in the gut, such as *Lactobacillus* and *Bifidobacterium* species. They do this by providing a source of nutrition for these bacteria, which can help them to grow and thrive. Additionally, polyphenols have been shown to have antimicrobial properties, which can help to inhibit the growth of harmful bacteria in the gut. There are many different types of polyphenols, each with their own unique properties and potential health benefits. Some common types of polyphenols include flavonoids, phenolic acids, and stilbenes. Some examples of foods that are rich in polyphenols include berries, grapes, green tea, and dark chocolate. When used as prebiotic supplements, polyphenols are typically taken in the form of capsules or powders. The dosages used can vary depending on the specific polyphenol being used and the desired health benefit. For example, some studies have used dosages of up to 500 mg per day of polyphenol supplements to improve gut health and reduce inflammation.

Stilbenes are a type of polyphenol that are found in a variety of plant-based foods, such as grapes, berries, peanuts, and red wine. They are known for their antioxidant and anti-inflammatory properties, and have been shown to have a variety of health benefits, including reducing the risk of cardiovascular disease, improving cognitive function, and promoting gut health. Recent research has suggested that stilbenes may also act as prebiotics, meaning they can promote the growth of beneficial bacteria in the gut. Prebiotics are a type of dietary fiber that are not digested by the human body, but instead are fermented by bacteria in the gut. This fermentation process produces short-chain fatty acids, which are a source of energy for the cells in the colon, and also help to support the growth of beneficial bacteria. Stilbenes can act as prebiotics by promoting the growth of specific strains of beneficial bacteria in the gut, such as *Lactobacillus* and *Bifidobacterium* species. They do this by providing a source of nutrition for these bacteria, which can help them to grow and thrive. Additionally, stilbenes have been shown to have antimicrobial properties, which can help to inhibit the growth of harmful bacteria in the gut. One of the most well-known stilbenes is resveratrol (which is described in greater detail below), which is found in grapes and red wine. Resveratrol has been shown to have a variety of health benefits, including reducing inflammation, improving cardiovascular health, and promoting longevity. When used as prebiotic supplements, stilbenes are typically taken in the form of capsules or powders. The dosages used can vary depending on the specific stilbene being used and the desired health benefit. For example, some studies have used dosages of up to 500 mg per day of resveratrol supplements to improve gut health and reduce inflammation.

Theobromine, the chemical structure of which is shown below, is a naturally occurring compound found in cocoa beans, tea leaves, and other foods. It is similar in structure to caffeine and is known for its mild stimulant effects. In recent years, theobromine supplementation has gained popularity as a potential natural remedy for several health conditions. One of the main health benefits of theobromine supplementation is its ability to improve blood flow and lower blood pressure. Studies have shown that theobromine can relax blood vessels and improve circulation, which may be beneficial for people with high blood pressure, heart disease, or other cardiovascular conditions. Theobromine may also have benefits for people with respiratory conditions such as asthma. Studies have shown that theobromine can help relax the smooth muscle in the airways, which can improve breathing and reduce symptoms of wheezing and coughing. Additionally, theobromine may have mood-enhancing effects similar to caffeine, although these effects are generally milder. Theobromine is known to stimulate the production of dopamine and other neurotransmitters in the brain, which can improve mood, energy, and focus. Common dosages of theobromine range from 100 mg to 1 g per day, though the specific dose may be higher or lower depending on a particular desired result or formulation.

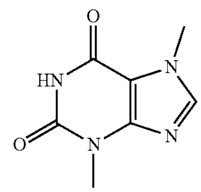

Huperzine A, the chemical structure of which is shown below, is a natural compound derived from the *Huperzia serrata* plant. It is commonly used as a dietary supplement to improve cognitive function and memory, and may have other potential health benefits as well. The recommended dosage for Huperzine A varies depending on the desired effect. One of the primary health benefits of Huperzine A supplementation is its ability to improve cognitive function and memory. In a study published in the Journal of Psychopharmacology (Sun Q Q, Xu S S, Pan J L, Guo H M, Cao W Q. *Huperzine-A capsules enhance memory and learning performance in* 34 *pairs of matched adolescent students*. Zhongguo Yao Li Xue Bao. 1999 July; 20(7):601-3. PMID: 10678121), participants who took Huperzine A showed significant improvements in memory recall and cognitive function compared to those who took a placebo. Huperzine A works by inhibiting the activity of an enzyme that breaks down acetylcholine, a neurotransmitter that is important for learning and memory. By increasing acetylcholine levels in the brain, Huperzine A can improve cognitive function, memory, and mental clarity. Huperzine A may also have neuroprotective effects and may be beneficial for people with neurodegenerative conditions such as Alzheimer's disease. Studies have shown that Huperzine A can protect brain cells from oxidative damage and may reduce inflammation in the brain, which can help slow the progression of these conditions. Huperzine A may enhance the effects of L-DOPA by increasing the availability of acetylcholine, a neurotransmitter that is involved in cognitive function. A study published in the journal Life Sciences (Qian Z M, Ke Y. *Huperzine A: Is it an Effective Disease-Modifying Drug for Alzheimer's Disease*? Front Aging Neurosci. 2014 Aug. 19; 6:216. doi: 10.3389/fnagi.2014.00216. PMID: 25191267; PMCID: PMC4137276) found that a combination of L-DOPA and Huperzine A improved cognitive function in rats more than L-DOPA alone. In addition to its effects on cognitive function and neuroprotection, Huperzine A may also have benefits for people with muscle weakness and other neuromuscular conditions. Huperzine A has been shown to increase levels of a neurotransmitter called acetylcholine in the neuromuscular junction, which can improve muscle strength and function. Typical doses range from 50-400 mcg per day, though this may vary according to a particular formulation or desired effects.

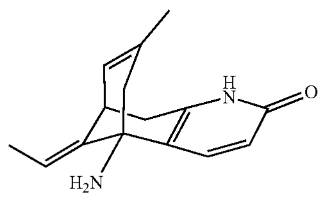 [SMILES: C/C=C1\C2C=C(C)CC1(N)c1ccc(=O)[nH]c1C2]

*Ginkgo biloba* extract is a popular herbal supplement that has been used for centuries to improve cognitive function and circulation, demonstrating effects the work synergistically when combined with theobromine to greatly improve circulatory and cognitive health. The active compounds in *Ginkgo biloba* extract are flavonoids and terpenoids. Flavonoids are antioxidants that protect cells from oxidative damage, while terpenoids are believed to improve blood flow by dilating blood vessels and reducing platelet aggregation. One of the main benefits of *Ginkgo biloba* extract is its ability to improve cognitive function, especially in older adults. Studies have shown that *Ginkgo biloba* extract can improve memory, attention, and processing speed in people with age-related cognitive decline. This is thought to be due to the increased blood flow to the brain, as well as the neuroprotective effects of the flavonoids. Studies have also shown that *Ginkgo biloba* extract may have benefits for people with age-related cognitive decline, dementia, and Alzheimer's disease. In one study, participants with age-related cognitive decline were given *Ginkgo biloba* extract for six months. The results showed significant improvements in memory, attention, and executive function compared to a placebo group. Another study found that *Ginkgo biloba* extract was effective at improving cognitive function in people with mild to moderate Alzheimer's disease. In addition to its effects on cognitive function, *Ginkgo biloba* extract may also have benefits for people with anxiety and depression. The flavonoids in *Ginkgo biloba* extract have been shown to have anxiolytic effects, reducing symptoms of anxiety in people with generalized anxiety disorder. Studies have also shown that *Ginkgo biloba* extract can improve walking distance and reduce pain in people with peripheral artery disease (PAD). Dosage for *Ginkgo biloba* extract commonly ranges from 100-250 mg per day, often taken as multiple smaller doses over the course of the day.

*Bacopa monnieri*, also called water hyssop, is an herb commonly used in Ayurvedic medicine for its potential cognitive-enhancing effects. The active compounds in Bacopa extract include bacosides, alkaloids, and flavonoids. Bacosides are the main active compounds in Bacopa extract and are responsible for its potential cognitive-enhancing effects. They work by increasing the production of certain neurotransmitters, including acetylcholine and serotonin, which are involved in learning, memory, and mood. Studies have shown that Bacopa extract can improve cognitive function, memory recall, and attention span, particularly in older adults. Bacopa extract also contains several alkaloids, including brahmine and herpestine, which have been shown to have neuroprotective and anti-inflammatory effects. These compounds may help protect brain cells from damage caused by oxidative stress and inflammation, which can contribute to cognitive decline and neurodegenerative conditions. Bacopa extract also contains several flavonoids, including luteolin and apigenin, which have antioxidant and anti-inflammatory properties. These compounds may help protect against the damage caused by free radicals and inflammation, which can contribute to cognitive decline and other health conditions. Bacopa extract has been shown to have cognitive-enhancing properties and may have a synergistic effect when combined with L-DOPA. A study published in the *Journal of Ethnopharmacology* (Shinomol G K, Muralidhara, Bharath M M. *Exploring the Role of "Brahmi" (Bacopa monnieri and Centella asiatica) in Brain Function and Therapy*. Recent Pat Endocr Metab Immune Drug Discov. 2011 January; 5(1):33-49. doi: 10.2174/187221411794351833. PMID: 22074576) found that a combination of L-DOPA and Bacopa extract improved cognitive performance in rats more than L-DOPA alone. Common dosages range from 50-600 mg per day, though the exact dose may be higher or lower according to a particular formulation or desired result.

*Hericium erinaceus*, or Lion's Mane, is a type of edible mushroom that has been used for its potential health benefits, including cognitive enhancement. The active compounds in Lion's Mane extract include beta-glucans, erinacines, hericenones, and polysaccharides. Beta-glucans are complex sugars found in Lion's Mane that have been shown to have immune-boosting effects. Beta-glucans can stimulate the activity of immune cells, such as macrophages and natural killer cells, which help defend against infections and diseases. Erinacines and hericenones are two types of compounds found in Lion's Mane that have been shown to have neuroprotective and cognitive-enhancing effects. Erinacines and hericenones can stimulate the production of nerve growth factor (NGF), a protein that plays a crucial role in the growth, maintenance, and survival of neurons. Studies have shown that Lion's Mane extract can improve cognitive function, memory recall, and concentration, particularly in older adults. Lion's Mane extract also contains several polysaccharides, which are complex sugars that have antioxidant and anti-inflammatory properties. These compounds may help protect against the damage caused by free radicals and inflammation, which can contribute to cognitive decline and other health conditions. Common dosages range from 500 mg to 3 g per day, though the exact dose may be higher or lower according to a particular formulation or desired result.

*Withania somnifera*, also called Ashwagandha, is a popular herb in Ayurvedic medicine that has been used for its potential health benefits, including stress reduction, immune system support, and cognitive enhancement. The active compounds in Ashwagandha extract include withanolides, alkaloids, and saponins. Withanolides are the primary active compounds in Ashwagandha extract and have been shown to have anti-inflammatory, antioxidant, and immunomodulatory properties. Withanolides may help reduce inflammation in the body, which can contribute to a wide range of health issues, including cognitive decline. Withanolides may also support the immune system by promoting the activity of immune cells. Studies have suggested that Ashwagandha extract can help reduce stress and anxiety, improve memory and cognitive function, and improve overall well-being. Ashwagandha extract also contains alkaloids, which are nitrogen-containing compounds that have been shown to have sedative and anxiolytic effects. Alkaloids may help reduce anxiety and promote relaxation, which can be beneficial for those experiencing stress-related cognitive decline. Ashwagandha extract also contains saponins, which are natural compounds found in Ashwagandha extract that have been shown to have anti-inflammatory, antioxidant, and immune-boosting effects. Saponins may help improve overall health by reducing inflammation and oxidative stress, which can contribute to cognitive decline and other health issues. Common dosages range from 250-1000 mg per day, though the exact dose may be higher or lower according to a particular formulation or desired result.

Saffron is a spice derived from the flower of *Crocus sativus* and has been used traditionally in various cultures for its medicinal properties. The active compounds in saffron include crocins, safranal, and picrocrocin, which are responsible for its various therapeutic effects. Crocins are water-soluble carotenoids and are the main active components of saffron. Crocins have been shown to have antioxidant, anti-inflammatory, and neuroprotective properties. They may help protect the brain from oxidative stress, inflammation, and cell damage, which can contribute to cognitive decline. Studies have suggested that saffron extract may help improve memory, attention, and other cognitive functions. Safranal, the chemical structure of which is shown and labeled below, is the volatile compound that gives saffron its distinctive aroma and flavor. Safranal has been shown to have antidepressant, anxiolytic, and sedative effects. It may help reduce anxiety and depression, improve mood, and promote relaxation, which can be beneficial for those experiencing stress-related cognitive decline. Picrocrocin, the chemical structure of which is shown and labeled below, is a bitter-tasting compound and is responsible for the bitter taste of saffron. Picrocrocin has been shown to have antioxidant and anti-inflammatory properties. It may help protect the brain from oxidative stress and inflammation, which can contribute to cognitive decline. Common dosages range from 15-50 mg per day, though the exact dose may be higher or lower according to a particular formulation or desired result.

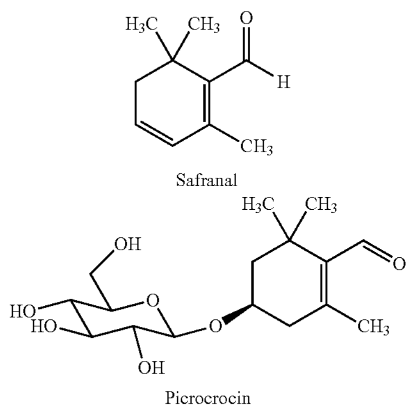

Safranal

Picrocrocin

*Rhodiola rosea*, also called "golden root", is an adaptogenic herb that has been used for centuries in traditional medicine to improve physical and mental performance, reduce fatigue, and enhance overall well-being. The active compounds in *Rhodiola* include rosavin, salidroside, and tyrosol, which are responsible for its various therapeutic effects. Rosavin, the chemical structure of which is shown and labeled below, is a glycoside that is unique to *Rhodiola* and has been shown to have anti-inflammatory and antioxidant properties. It may help protect the brain from oxidative stress, inflammation, and cell damage, which can contribute to cognitive decline. Studies have suggested that *Rhodiola* extract may help improve cognitive function, attention, and mental performance. Salidroside, the chemical structure of which is shown and labeled below, is a glucoside and is the most abundant and active compound in *Rhodiola*. Salidroside has been shown to have anti-inflammatory, antioxidant, and anti-fatigue effects. It may help reduce fatigue, improve mood, and enhance physical and mental performance. Studies have suggested that *Rhodiola* extract may help improve exercise performance and reduce mental fatigue. *Rhodiola* has been shown to have a synergistic effect when combined with L-DOPA, including one study published in the *Journal of Medicinal Food* (Cropley M, Banks A P, Boyle J. *The Effects of Rhodiola rosea L. Extract on Anxiety, Stress, Cognition and Other Mood Symptoms*. Phytother Res. 2015 December; 29(12):1934-9. doi: 10.1002/ptr.5486. Epub 2015 Oct. 27. PMID: 26502953) which found that a combination of L-DOPA and *Rhodiola* extract improved cognitive performance and reduced mental fatigue in healthy adults. Tyrosol, the chemical structure of which is shown and labeled below, is a phenolic compound and is also present in olives and olive oil. Tyrosol has been shown to have antioxidant and anti-inflammatory properties. It may help protect the brain from oxidative stress and inflammation, which can contribute to cognitive decline. Studies have suggested that *Rhodiola* extract may help improve cognitive function and memory. Common dosages range from 100-600 mg per day, though the exact dose may be higher or lower according to a particular formulation or desired result.

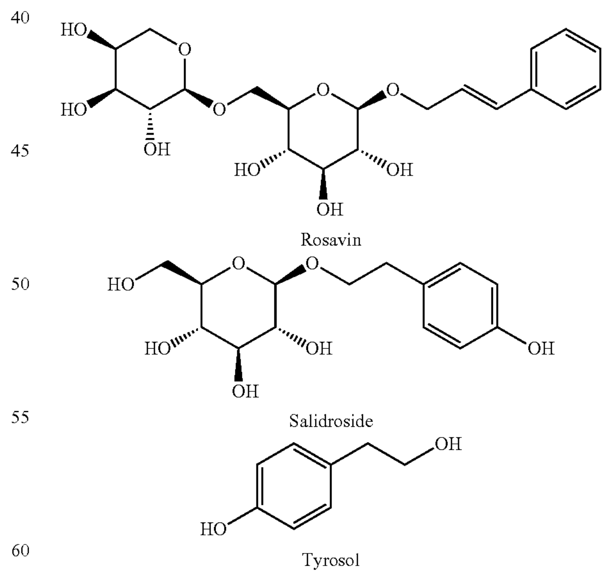

Rosavin

Salidroside

Tyrosol

Phosphatidylserine ("PS"), the chemical structure of which is shown below, is a phospholipid that is a crucial component of the cell membrane in the human body. It is found in high concentrations in the brain and is essential for proper cellular function. PS has been shown to improve cognitive function, including memory, attention, and processing speed. It may also help with learning and problem-solving skills, and may improve mood by reducing symptoms of depression and anxiety. It also may help to reduce the effects of stress on the body, including reducing cortisol levels and improving overall mood. PS may help to slow down the age-related decline in cognitive function, protecting against age-related cognitive decline and neurodegenerative diseases such as Alzheimer's and Parkinson's disease. Typical doses range from 100-500 mg per day, although higher doses have also been used to achieve specific effects or in recipes involving other ingredients.

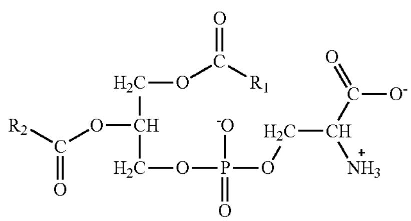

L-glutathione, the chemical structure of which is shown below, is a tripeptide consisting of the amino acids glutamine, cysteine, and glycine. It is found in virtually every cell of the body and is considered to be one of the most important endogenous antioxidants. L-glutathione plays a vital role in detoxifying harmful substances that can damage cells and tissues, as well as maintaining the proper functioning of the immune system. Additionally, L-glutathione is also involved in the synthesis of DNA and proteins, as well as in the metabolism of fats and carbohydrates. L-glutathione has been found to play an important role in protecting the brain against oxidative stress, which can lead to the development of various neurological disorders. For example, studies have shown that L-glutathione levels are decreased in the brains of individuals with Alzheimer's disease, Parkinson's disease, and multiple sclerosis. Additionally, some research suggests that increasing L-glutathione levels may help to prevent or slow the progression of these and other neurological disorders. Furthermore, L-glutathione has been found to have neuroprotective effects against the damage caused by certain toxins and chemicals, such as heavy metals, pesticides, and radiation. It is also thought to help reduce inflammation in the brain, which can be a contributing factor in the development of various neurological disorders. Typical doses range from 250 mg to 1 g, although higher doses have also been used to achieve specific effects or in recipes involving other ingredients.

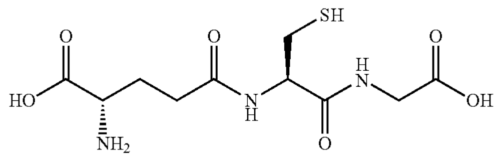 [SMILES: N[C@@H](CCC(=O)N[C@@H](CS)C(=O)NCC(=O)O)C(=O)O]

Alpha-GPC (L-alpha glycerylphosphorylcholine), the chemical structure of which is shown below, is a natural compound that is found in the brain and is also available as a dietary supplement commonly used to improve cognitive function, enhance athletic performance, and promote overall health. It is a precursor to the neurotransmitter acetylcholine, which plays a crucial role in cognitive function, memory, and learning. Alpha-GPC is believed to have a number of neurological benefits, particularly for those with cognitive impairments or age-related decline. One of the most notable benefits of Alpha-GPC is its ability to improve cognitive function and memory. Studies have found that Alpha-GPC supplementation can enhance attention, focus, and memory in healthy individuals, as well as in those with cognitive impairment. Additionally, some research suggests that Alpha-GPC may be beneficial for individuals with Alzheimer's disease, as it may help to improve memory and cognitive function. Furthermore, Alpha-GPC has been found to have neuroprotective effects, meaning it can help to protect brain cells from damage caused by free radicals and other harmful substances. This can be especially important for older adults or those with certain neurological conditions, as these individuals may be at increased risk for brain damage. In addition, Alpha-GPC has been found to increase the production of growth hormone and may therefore have potential benefits for athletic performance, muscle growth, and recovery. It is also believed to have anti-inflammatory effects, which can be beneficial for individuals with various inflammatory conditions, including those affecting the brain. Typical doses range from 300-1200 mg per day, although higher doses have also been used to achieve specific effects or in recipes involving other ingredients.

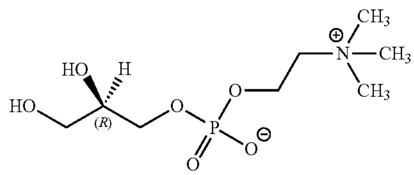

Acetyl-L-carnitine ("ALCAR"), the chemical structure of which is shown below, is a naturally occurring compound in the body that plays a critical role in energy metabolism. It is a derivative of the amino acid, L-carnitine, which is essential for transporting long-chain fatty acids into the mitochondria, where they can be used for energy production. ALCAR is known to cross the blood-brain barrier and has been extensively studied for its neurological benefits. One of the primary neurological benefits of ALCAR is its ability to enhance cognitive function. ALCAR has been shown to improve memory, attention, and overall cognitive performance in both healthy individuals and those with cognitive impairment. It may also have a neuroprotective effect by reducing oxidative stress and inflammation, which are believed to contribute to neurodegenerative diseases such as Alzheimer's and Parkinson's. ALCAR has also been studied for its potential to improve mood and alleviate symptoms of depression. It may enhance the activity of neurotransmitters such as serotonin and dopamine, which are known to play a role in regulating mood and emotion. Additionally, ALCAR has been shown to improve peripheral neuropathy, a condition characterized by damage to the peripheral nervous system. It may improve nerve function and reduce pain in individuals with conditions such as diabetic neuropathy and chemotherapy-induced peripheral neuropathy. Typical doses range from 500-2000 mg per day, although higher doses have also been used to achieve specific effects or in recipes involving other ingredients.

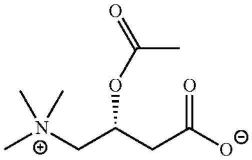

Uridine, the chemical structure of which is shown below, is a naturally occurring nucleoside, which is found in RNA and is essential for normal cellular metabolism. It plays a crucial role in the formation of new brain cells and has been shown to have a range of neurological benefits. One of the most well-known benefits of uridine is its ability to enhance cognitive function, including memory and learning. Research has shown that uridine may increase the production of important brain chemicals, such as acetylcholine and dopamine, which are involved in learning and memory processes. It has also been suggested that uridine may improve the communication between brain cells by increasing the number of synapses, the tiny gaps between neurons that allow them to transmit information. In addition to its cognitive benefits, uridine has also been shown to have a protective effect on the brain. Studies have found that uridine may help to prevent or reduce the damage caused by certain neurodegenerative diseases, such as Alzheimer's and Parkinson's disease. Uridine is also involved in the production of phospholipids, which are essential components of cell membranes. This may help to improve the integrity of the cell membranes in the brain, which could lead to better overall brain health. Typical doses range from 250-1000 mg per day, although higher doses have also been used to achieve specific effects or in recipes involving other ingredients.

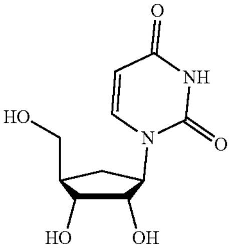

Gamma-aminobutyric acid ("GABA"), the chemical structure of which is shown below, is a neurotransmitter that plays a critical role in regulating brain activity. It is the primary inhibitory neurotransmitter in the central nervous system, which means it helps to calm and regulate the activity of neurons. GABA is involved in a wide range of brain functions, including mood, sleep, and anxiety. Supplementing with GABA has been shown to have a number of neurological benefits. One of the most well-known benefits of GABA supplementation is its ability to reduce anxiety. Research has found that GABA may help to calm the activity of the amygdala, the part of the brain that is responsible for regulating fear and anxiety. GABA supplementation may also improve sleep quality and reduce symptoms of depression. In addition to its anxiolytic and mood-enhancing effects, GABA has also been shown to have neuroprotective properties. Studies have found that GABA may help to prevent neuronal damage caused by oxidative stress, inflammation, and other factors. This may make it beneficial for preventing or treating neurodegenerative diseases, such as Alzheimer's and Parkinson's disease. GABA supplementation may also have benefits for cognitive function. Research has found that GABA may improve memory, learning, and attention in healthy individuals. It may also improve cognitive function in people with mild cognitive impairment or other forms of cognitive decline.

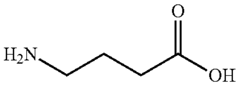

5-methyltetrahydrofolate ("5-MTHF"), the chemical structure of which is shown below, is the active, naturally occurring form of folate that is essential for many biological processes in the body, including supporting homocysteine levels, cardiovascular and cognitive function, memory, DNA synthesis, neurotransmitter synthesis, and methylation. Methylation is a process in which a methyl group is added to a molecule, and it plays an important role in regulating gene expression, detoxification, and many other cellular processes. One of the most significant neurological benefits of 5-MTHF is its ability to support the production of neurotransmitters, which are chemical messengers that transmit signals between nerve cells in the brain. 5-MTHF is a key component in the synthesis of several important neurotransmitters, including serotonin, dopamine, and norepinephrine, and 5-MTHF has also been shown to play a role in reducing inflammation and oxidative stress, which can be beneficial for overall brain health. Research suggests that 5-MTHF supplementation may be helpful for people with certain neurological conditions, such as depression and Alzheimer's disease. For example, a study published in the Journal of Clinical Psychopharmacology found that supplementation with 5-MTHF improved symptoms of depression in patients who did not respond to traditional antidepressant medications. Low levels of folate and its active form, 5-MTHF, are associated with a higher risk of developing neurological disorders such as depression, anxiety, and cognitive impairment. In fact, studies have suggested that supplementation with 5-MTHF may improve symptoms of depression and cognitive dysfunction. Additionally, combining HGH (described below) with 5-MTHF may improve the overall effectiveness of HGH therapy, as 5-MTHF helps to support healthy methylation processes in the body, which are important for overall health and well-being. A typical dosage range for 5-MTHF supplementation is between 400 to 1,000 mcg per day, but dosage may vary according to a particular intended benefit or combination with other ingredients.

Combining CBD with 5-MTHF may offer benefits for mood and cognitive function. Folate, including 5-MTHF, is necessary for the synthesis of neurotransmitters that are important for regulating mood and cognitive function, while CBD has been shown to have anxiolytic and antidepressant effects. Combining CBD with 5-MTHF may enhance the body's ability to produce these neurotransmitters and improve mood and cognitive function. One potential benefit of combining CBD and 5-MTHF supplementation is the potential to support healthy brain function. Both CBD and 5-MTHF have been studied for their potential effects on cognitive function, and may work together to support healthy brain function. Additionally, CBD has been shown to have potential neuroprotective effects, which may help to support brain health over time. Another potential benefit of combining CBD and 5-MTHF is the potential to support overall immune health. Both CBD and 5-MTHF have been studied for their potential effects on inflammation, which is an important factor in immune health. By working together to reduce inflammation, these supplements may help to support overall immune function and reduce the risk of chronic diseases. When these two supplements are combined, they may work together to provide even greater neuroprotective effects. 5-MTHF may help to support healthy DNA synthesis and cell growth, while CBD may help to protect neurons from oxidative stress and inflammation. Additionally, some research has suggested that CBD may enhance the bioavailability and effectiveness of folate supplements, which could further enhance the neuroprotective effects of 5-MTHF.

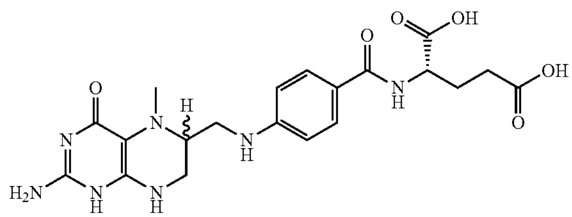 [SMILES: CN1c2c([nH]c(N)nc2=O)NCC1CNc1ccc(C(=O)N[C@@H](CCC(=O)O)C(=O)O)cc1]

CDP Choline (also called citicholine), the chemical structure of which is shown below, is a compound that is naturally produced in the body and is an intermediate in the synthesis of phosphatidylcholine, an important component of cell membranes. It has been shown to have several neurological benefits. One of the most significant benefits of CDP choline is its ability to improve cognitive function, especially in individuals with age-related cognitive decline or brain injury. It enhances memory, attention, and other cognitive functions, leading to improved mental clarity and energy levels. CDP choline has also been found to increase the density of dopamine receptors in the brain, which can improve mood and motivation. It is involved in the production of ATP, which is the primary energy source for cells, and can enhance brain metabolism, further contributing to improved mental function. Furthermore, CDP choline has been shown to protect the brain against damage caused by various toxins and injuries, including ischemia (reduced blood flow) and traumatic brain injury. It is also beneficial for improving visual function in individuals with glaucoma and other eye disorders. The appropriate dosage range for citicoline supplementation can also vary depending on individual factors such as age, health status, and reason for use. However, a typical dosage range for citicoline is between 250 to 500 mg taken orally, two times per day. In some cases, higher dosages of up to 2,000 mg per day may be used under medical supervision.

When combining citicholine with 5-MTHF, the two ingredients demonstrate synergistic effects on cognitive function and mood regulation. For example, citicoline enhances the production of neurotransmitters that are dependent on folate, such as dopamine, leading to improved mood and motivation. Additionally, 5-MTHF enhances the anti-inflammatory effects of citicoline, further protecting the brain from damage. Combining citicholine with cannabinoids (described below) may enhance the cognitive benefits of cannabinoids, such as improving memory and attention span, as well as reducing anxiety.

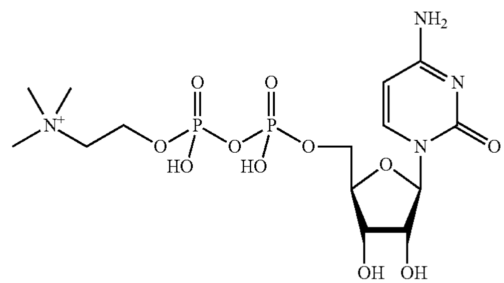

Methylcobalamin, the chemical structure of which is shown below, is a form of vitamin B12 that is essential for proper neurological function. It is involved in the production of myelin, a fatty substance that surrounds and insulates nerve fibers, and is also necessary for the formation of red blood cells. Methylcobalamin has been shown to improve cognitive function, particularly in individuals with age-related cognitive decline or brain injury, and also helps to protect against nerve damage by promoting the growth and repair of nerve cells. It has been used to treat neuropathic pain and diabetic neuropathy. Methylcobalamin plays a role in the production of neurotransmitters such as serotonin and dopamine, which are involved in regulating mood. Supplementation may improve symptoms of depression and anxiety, as well as improve sleep quality. The appropriate dosage range for methylcobalamin supplementation can also vary depending on individual factors such as age, health status, and reason for use. However, a typical dosage range for methylcobalamin is between 1,000 to 5,000 mcg taken orally, one to two times per week. In some cases, higher dosages may be recommended under medical supervision.

Compared to cyanocobalamin, another form of vitamin B12 commonly used in supplements, methylcobalamin has some advantages in terms of neurological benefits. Cyanocobalamin needs to be converted to methylcobalamin in the body to be active, and some individuals may have difficulty with this conversion. Methylcobalamin is already in its active form, making it more readily available for neurological functions. Additionally, cyanocobalamin contains a cyanide molecule, which can be toxic in high doses, while methylcobalamin is considered to be a safer alternative.

When combined with citicoline and 5-MTHF, methylcobalamin may enhance the production of neurotransmitters that are involved in cognitive function and mood regulation. Additionally, all three supplements have anti-inflammatory effects and may help to protect against brain damage caused by inflammation. combining methylcobalamin with 5-MTHF may be particularly beneficial for individuals with conditions such as depression or dementia, as these conditions are associated with deficiencies in both of these nutrients. Methylcobalamin may also enhance the effects of citicoline on brain metabolism and energy production, leading to improved mental clarity and energy levels. Additionally, combining cannabinoids with methylcobalamin may help to support healthy nervous system function and reduce the risk of neurological disorders.

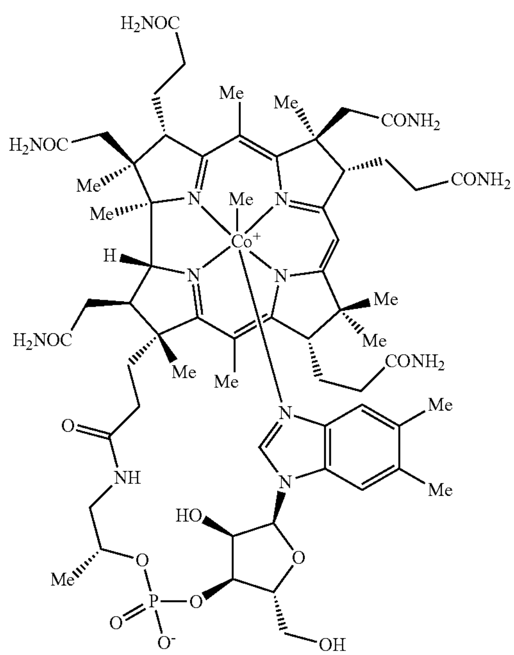

P-5-P (pyridoxal-5-phosphate, also called PLP), the chemical structure of which is shown below, is the active form of vitamin B6. It is a coenzyme involved in over 100 enzymatic reactions in the body, including the production of neurotransmitters, the regulation of gene expression, and the metabolism of amino acids and fatty acids. P-5-P is particularly important for neurological health, as it is involved in several processes that support proper brain function. One of the primary neurological benefits of P-5-P is its role in the production of neurotransmitters. P-5-P is necessary for the synthesis of several neurotransmitters, including serotonin, dopamine, and gamma-aminobutyric acid (GABA). These neurotransmitters are involved in mood regulation, motivation, and cognitive function, and imbalances in their levels have been associated with several neurological disorders. P-5-P is also involved in the synthesis of sphingolipids, which are important components of myelin, the fatty substance that surrounds and insulates nerve fibers. Proper myelination is essential for efficient nerve signaling and the proper functioning of the nervous system. Deficiencies in P-5-P have been linked to demyelinating disorders such as multiple sclerosis. In addition to its role in neurotransmitter synthesis and myelination, P-5-P has anti-inflammatory effects and may help to protect against neuroinflammation, which is associated with several neurological disorders. P-5-P has also been shown to improve cognitive function, particularly in individuals with age-related cognitive decline. Compared to other forms of vitamin B6, P-5-P has some advantages in terms of neurological benefits. Other forms of vitamin B6, such as pyridoxine or pyridoxal, need to be converted to P-5-P in the body to be active, and some individuals may have difficulty with this conversion. P-5-P is already in its active form, making it more readily available for neurological functions. The appropriate dosage range for pyridoxal-5-phosphate (P-5-P) supplementation can vary depending on individual factors such as age, health status, and reason for use. However, a typical dosage range for P-5-P is between 10 to 50 mg taken orally, one to three times per day. Higher doses may be recommended under medical supervision for certain conditions.

When combined with citicoline, 5-MTHF, and methylcobalamin, P-5-P may enhance the synergistic effects of these supplements on brain function and promote overall neurological health. Specifically, P-5-P may enhance the effects of methylcobalamin on myelin production and red blood cell formation, as it is involved in the metabolism of amino acids and fatty acids that are necessary for these processes. This could potentially improve nerve signaling and cognitive function, particularly in individuals with age-related cognitive decline or conditions such as dementia. P-5-P may also enhance the effects of citicoline on brain metabolism and energy production, which could lead to improved mental clarity and energy levels. Additionally, P-5-P and 5-MTHF may work synergistically to support the production of neurotransmitters, particularly serotonin, which is important for mood regulation and cognitive function. Finally, P-5-P may have its own anti-inflammatory effects, which could complement the anti-inflammatory effects of citicoline and 5-MTHF. This could potentially help to protect against neuroinflammation and the development of neurological disorders such as Alzheimer's disease and multiple sclerosis. Additionally, P-5-P is a component in the natural production of HGH in the body, and thus combining HGH with P-5-P may help to optimize the body's natural production of HGH.

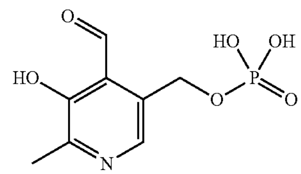 [SMILES: Cc1ncc(COP(=O)(O)O)c(C=O)c1O]

Tocopherols are a group of four organic compounds collectively known as vitamin E, occurring in alpha (α), beta (β), gamma (γ), and delta (δ) forms each comprising a chromane ring and a hydroxyl group, the particular form being determined by the methylation of the chromane ring. These forms vary slightly in their chemical structure and biological activity, as shown and described below. All tocopherols are potent inhibitors of reactive oxygen species at a cellular level, reducing cancer risks, cellular aging, and the development of cardiovascular disease. When used in topical applications in conjunction with carnosine, the mixture has synergistic benefits for skin health, improving firmness, smoothness, and hydration as well as reducing the depth of various wrinkles by 24-27% after just one month of regular application.

α-tocopherol, the chemical structure of which is shown below, is the most common and biologically active form and is commonly used in supplements with dosages measured in International Units (IU). It is a potent antioxidant that helps to protect cell membranes and other lipids from oxidative damage. Alpha-tocopherol is primarily found in foods of animal origin, such as liver, egg yolk, and dairy products. In large doses of 1600-3200 IU/day, the antioxidant effects of α-tocopherol significantly lower blood plasma concentration of F2-isoprostane. Dietary supplementation of α-tocopherol in doses up to 400 IU/day has also been shown to reduce the risk of developing neurodegenerative diseases such as Alzheimer's Syndrome or dementia by as much as 24% on controlled trials, as well as reducing the risk of coronary disease by up to 34% and contributing to lower risk of developing a number of cancers including kidney, lung, and bladder cancers. In combination with 10-20 mg β-carotene and 400-500 mg vitamin C, α-tocopherol has a synergistic effect that has been shown to dramatically reduce the progression of age-related macular degeneration in doses around 400-500 IU, as well as a 23% reduction in the development of age-related cataracts. α-tocopherol has also been shown to improve functional health of sperm in doses of 800-900 IU/day, with additional synergistic benefits in combination with vitamin C.

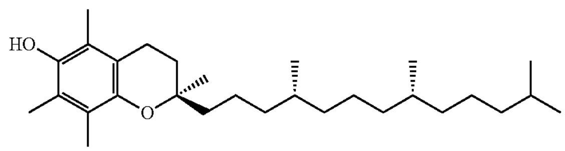 [SMILES: Cc1c(C)c2c(c(C)c1O)CC[C@@](C)(CCC[C@H](C)CCC[C@H](C)CCCC(C)C)O2]

β-tocopherol, the chemical structure of which is shown below, is also a potent antioxidant but is less biologically-active than the α-tocopherol form. It is found in plant-based foods, such as soybeans, nuts, and seeds as well as in various oils such as soybean, grapeseed, and olive oils. The relative biological activity of β-tocopherol is 0.5 as compared to α-tocopherol (i.e., assuming α-tocopherol has a biological activity factor of 1.0).

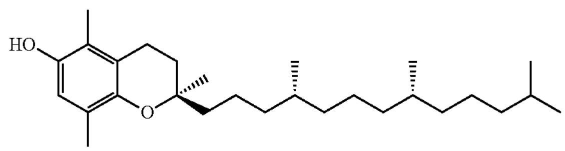 [SMILES: Cc1cc(O)c(C)c2c1O[C@](C)(CCC[C@H](C)CCC[C@H](C)CCCC(C)C)CC2]

γ-tocopherol, the chemical structure of which is shown below, is the second-most abundant form after α-tocopherol and has similar antioxidative capacity. It is found in high concentrations in nuts, seeds, and vegetable oils. It is a more effective scavenger of certain types of free radicals than alpha-tocopherol and is believed to play a key role in reducing inflammation and promoting heart health. However, due to the preferential uptake of the α-tocopherol form, γ-tocopherol is found at roughly 10% of the concentration of the preferred variant in vivo, even when dietary intake occurs in equal portions. The relative biological activity of the γ-tocopherol form is 0.1.

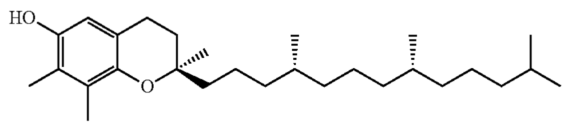 [SMILES: Cc1c(O)cc2c(c1C)O[C@](C)(CCC[C@H](C)CCC[C@H](C)CCCC(C)C)CC2]

δ-tocopherol, the chemical structure of which is shown below, is found in small amounts in some plant-based foods and has a relative biological activity of only 0.03. It has been shown to have antioxidant properties, like other forms of vitamin E. It can help protect cell membranes and other lipids from oxidative damage caused by free radicals. Additionally, it has been suggested that δ-tocopherol may play a role in preventing the formation of harmful nitrogen-containing compounds, which can contribute to the development of certain diseases. Some studies have also suggested that δ-tocopherol may have anti-inflammatory properties. In one study, for example, supplementation with δ-tocopherol reduced markers of inflammation in the blood of individuals with metabolic syndrome. δ-tocopherol has also been suggested to play a role in immune system function.

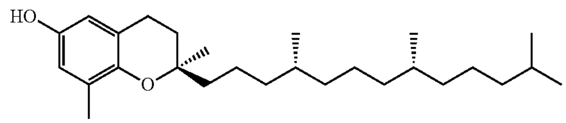 [SMILES: Cc1cc(O)cc2c1O[C@](C)(CCC[C@H](C)CCC[C@H](C)CCCC(C)C)CC2]

Tocotrienols are another group belonging to the vitamin E family, differing in structure from their analogous tocopherol forms by the presence of three double-bonds in the hydrophobic side chain. Like tocopherols, tocotrienols have antioxidant properties that help to protect cells from oxidative stress and damage caused by free radicals. Tocotrienols have been shown to support cardiovascular health by helping to lower cholesterol levels and improve blood flow. They have also been suggested to have anti-inflammatory properties, which may further benefit heart health. Tocotrienols may play a role in protecting the brain from damage and degeneration. Studies have suggested that they may help to improve cognitive function, reduce the risk of stroke, and protect against neurodegenerative diseases like Alzheimer's. Tocotrienols have been shown to have anti-cancer properties in laboratory studies. They may help to prevent the growth and spread of cancer cells, and may also enhance the effects of chemotherapy and radiation therapy.

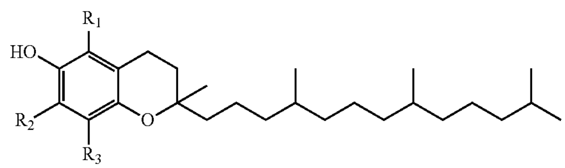

Tocopherols

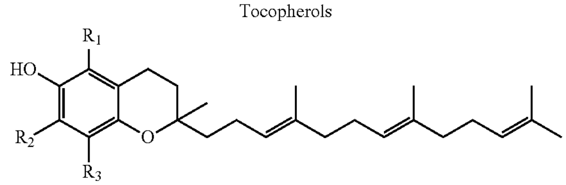

Tocotrienols

*Aloe vera* (also known as *Aloe barbadensis, Aloe indica, Aloe vulgaris*, and a number of other common-use names) is a succulent of the genus *Aloe*, widely cultivated for a variety of medicinal and cosmetic uses and one of the oldest known medicinal plants. Many of aloe's therapeutic properties are attributed to the phenols and polysaccharides in the gel of its leaves, which comprises roughly 98.5-99.5% water with the balance comprising over 200 known compounds in varying portions. Many of the primary medicinal compounds found in aloe are mucopolysaccharides (MPS) characterized by long-chain sugars as shown below.

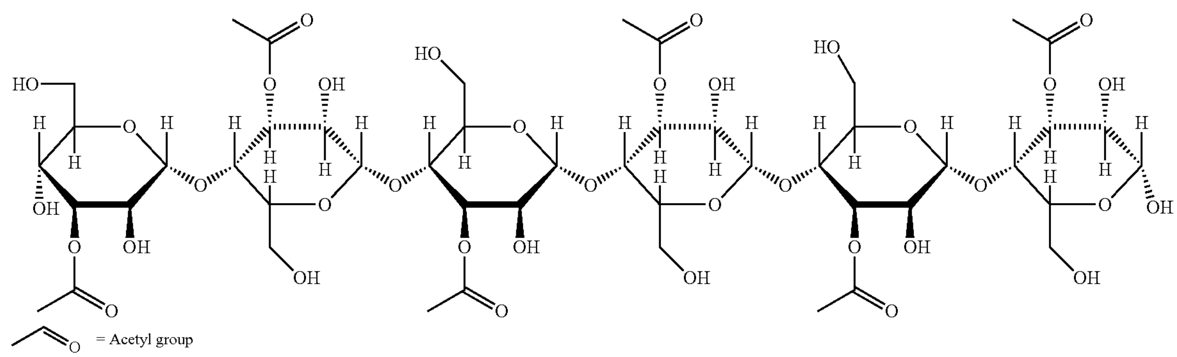

The aloe gel also contains mono/oligosaccharides and hemicelluloses which make up the more inert fraction of the phytocomplex shown below. Other compounds present include a variety of sugars, glycoproteins, flavonoids, minerals, enzymes, and various amino acids.

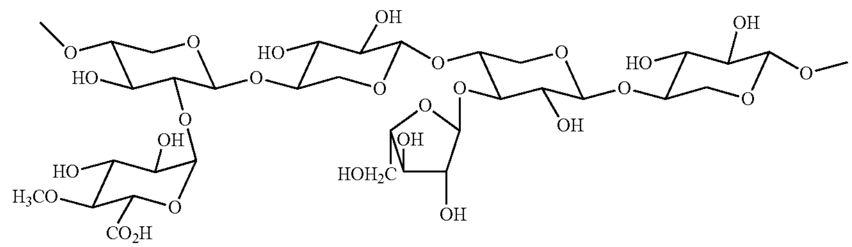

*Aloe* gel is commonly used in a variety of topical applications with therapeutic benefits for skin health and healing of minor injuries such as abrasions, burns, rashes, psoriasis, cold sores, or dry skin and is often combined with antioxidants such as vitamin E for synergistic benefits. For increased benefit, aloe gel may be enzymatically treated to hydrolyze hemicelluloses (thus transforming them into additional sugars and saccharides), or it may be fermented to boost the concentrations of various phytocomplexes present, resulting in as much as a fourfold increase in antioxidative capacity of the gel. In particular, fermenting aloe gel doubles both the amino acid and polyphenol content present in the gel, dramatically improving their availability for therapeutic uses. *Aloe vera* gel can help to enhance the absorption and efficacy of other beneficial ingredients, such as vitamin E, vitamin C, or hyaluronic acid. Look for skincare products that contain aloe vera gel along with other active ingredients. *Aloe vera* gel can be combined with other natural ingredients, such as honey, coconut oil, or tea tree oil, to create a nourishing and healing skincare product. These ingredients can help to enhance the moisturizing, antibacterial, or anti-inflammatory properties of aloe vera gel.

Ceramides are a class of lipid molecules naturally produced in the skin, with an exemplary chemical structure for a ceramide shown below (where R indicates the alkyl group of a fatty acid). Ceramides are a key component of the lipid bilayer in cell membranes, where they perform both barrier and signaling functions. Ceramides are an important component of the skin barrier, which helps to protect the skin from environmental stressors such as pollution, UV radiation, and harsh chemicals. Topical application of ceramides can help to reinforce the skin barrier and improve its function.

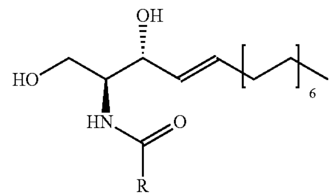

Glycerin (also called glycerol), the chemical structure of which is shown below, is a colorless, odorless, and viscous liquid that is widely used in skincare and cosmetic products. The chemical structure of glycerin is a triol, meaning it has three hydroxyl (—OH) groups attached to a propane backbone. The chemical formula for glycerin is C3H8O3. Glycerin is a natural humectant, which means it has the ability to attract and retain water. At concentrations of 2-5%, glycerin is widely used as a moisturizing ingredient in skincare products, including moisturizers, lotions, and creams. It helps to hydrate and soften the skin, improving its overall appearance and texture. At concentrations of 10-15%, glycerin can have a more significant moisturizing effect on the skin, helping to improve skin texture and reduce the appearance of fine lines and wrinkles. Glycerin also has anti-irritant properties and is often used in skincare products designed for sensitive skin. It can help soothe and calm irritated skin, reducing redness and inflammation. When combined with other ingredients, glycerin is a versatile solvent and is often used in skincare products to help dissolve other ingredients and improve their stability and shelf life, and at high concentrations of 20% or more it also provides thickening properties to improve the texture of formulations.

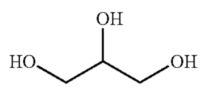

A palmitoyl tripeptide is a synthetic peptide comprising three peptides linked together with palmitoyl (a palmitic acid group). These peptides share similarities when used in topical applications, often employed as anti-aging or recovery agents. Several specific palmitoyl tripeptides and their therapeutic benefits are described below.

Palmitoyl tripeptide-1 (also known as Pal-GHK), the chemical structure of which is shown below, consists of three amino acids: glycine, histidine, and lysine, with a palmitoyl (a fatty acid) group attached to the N-terminus of the glycine residue. The full chemical structure is: palmitoyl-Gly-His-Lys-OH. Pal-GHK is known to stimulate collagen production, which can help reduce the appearance of fine lines and wrinkles, and improve skin elasticity. It can also help improve the skin's moisture levels, which can help reduce dryness and roughness, a property that is further enhanced when combined with polyacrylic acid, described below. Pal-GHK also has anti-inflammatory properties that can help soothe irritated skin and reduce redness, and has been shown to promote wound healing by enhancing cell proliferation and migration. The recommended dose of Pal-GHK in topical skincare products typically ranges from 1% to 5%, however the optimal dose may vary depending on the specific formulation and intended use.

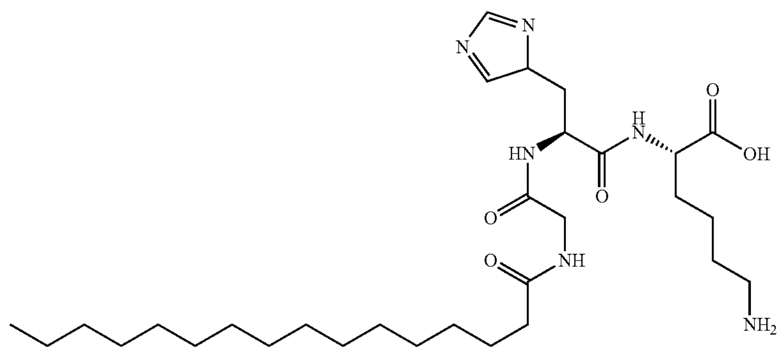 [SMILES: CCCCCCCCCCCCCCCC(=O)NCC(=O)N[C@@H](CC1C=NC=N1)C(=O)N[C@@H](CCCCN)C(=O)O]

Palmitoyl tripeptide-5 (also known as Pal-KTTKS), the chemical structure of which is shown below, consists of three amino acids: lysine, threonine, and threonine, with a palmitoyl group attached to the N-terminus of the lysine residue. The full chemical structure is: palmitoyl-Lys-Thr-Thr-Lys-Ser-OH. The palmitic acid attached to the tripeptide acts as a lipid carrier, helping to deliver the peptide to the skin's surface and increase its stability. Together, the amino acids and palmitic acid in palmitoyl tripeptide-5 work to stimulate collagen production, improve skin elasticity and firmness, and reduce the appearance of fine lines and wrinkles. A concentration of 0.5% is commonly used in skincare products such as serums and moisturizers; at this concentration, palmitoyl tripeptide-5 can help to improve skin texture, reduce the appearance of fine lines and wrinkles, and improve skin firmness and elasticity. A higher concentration of 2% is sometimes used in more concentrated skincare products such as serums. At this concentration, palmitoyl tripeptide-5 can provide more significant anti-aging benefits, including improved skin texture, increased firmness and elasticity, and a reduction in the appearance of fine lines and wrinkles.

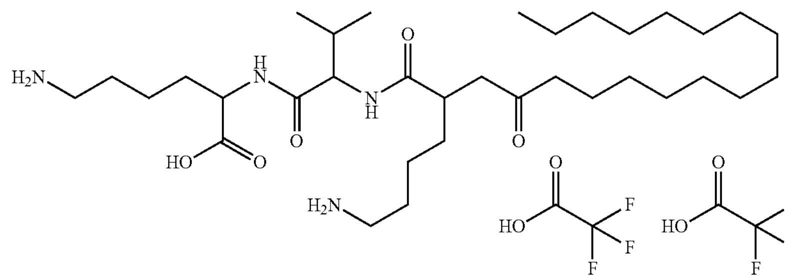

Palmitoyl tripeptide-7 (also known as palmitoyl oligopeptide), the chemical structure of which is shown below, is composed of three amino acids: glycine, glutamine, and proline, with a palmitoyl group attached to the N-terminus of the glycine residue. The full chemical structure is: palmitoyl-Gly-Gln-Pro-Arg-OH. Palmitoyl tripeptide-7 is believed to stimulate the synthesis of extracellular matrix proteins such as collagen and elastin, which can help improve skin elasticity, reduce the appearance of fine lines and wrinkles, and enhance overall skin texture. It has also been shown to have anti-inflammatory and wound healing benefits, and improves skin hydration particularly when combined with hydration enhancers such as polyacrylic acid, described below. The recommended dose of Palmitoyl tripeptide-7 in topical skincare products typically ranges from 1% to 5%, however the optimal dose may vary depending on the specific formulation and intended use.

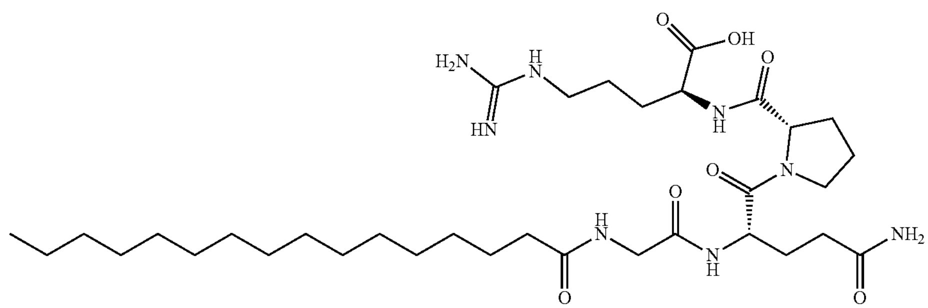 [SMILES: CCCCCCCCCCCCCCCC(=O)NCC(=O)N[C@@H](CCC(N)=O)C(=O)N1CCC[C@H]1C(=O)N[C@@H](CCCNC(=N)N)C(=O)O]

Hesperidin methyl chalcone (HMC), the chemical structure of which is shown below, is a flavonoid derived from citrus fruits, particularly the peel of oranges and lemons. It is a modified form of hesperidin, which is a flavanone glycoside commonly found in citrus fruits. HMC differs from regular hesperidin in its structure due to the addition of a methyl group (—CH3) to the chalcone molecule (as seen in the chemical structure diagram below), which is a type of flavonoid compound. The addition of this methyl group makes HMC more soluble in water and allows it to penetrate the skin more easily than regular hesperidin. This increased solubility and bioavailability contribute to the effectiveness of HMC in topical skincare applications HMC has been shown to have antioxidant, anti-inflammatory, and vasoconstrictive properties, which make it a useful ingredient in skincare products; HMC can improve blood circulation and reduce inflammation, which can help to reduce the appearance of dark circles under the eyes. By strengthening blood vessels and reducing the breakdown of collagen, HMC can help to improve the firmness and elasticity of the skin, and its anti-inflammatory properties can help to reduce skin redness and irritation, making it useful for people with sensitive skin or conditions like rosacea. The recommended concentration of HMC in skincare products is typically between 1% and 5%. However, the optimal concentration may vary depending on the specific product and intended use.

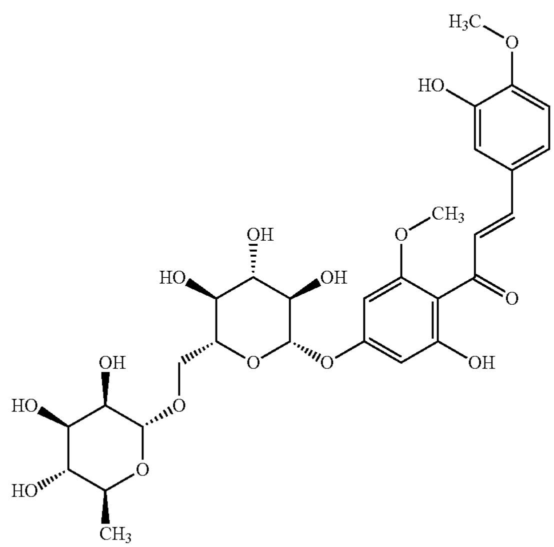 [SMILES: COc1ccc(/C=C/C(=O)c2c(O)cc(O[C@@H]3O[C@H](CO[C@@H]4O[C@@H](C)[C@H](O)[C@@H](O)[C@H]4O)[C@@H](O)[C@H](O)[C@H]3O)cc2OC)cc1O]

Steareth-20, the chemical structure of which is shown below, is a type of non-ionic surfactant that is commonly used as an emulsifier and solubilizer in cosmetic and personal care products. It is made from the reaction of ethylene oxide with stearyl alcohol, which is derived from vegetable or coconut oil. Steareth-20 can help to stabilize and evenly distribute oil-in-water emulsions, which are commonly used in moisturizers, lotions, and other skincare products. It is also used to solubilize oils and other lipophilic ingredients in water-based formulations, improving their efficacy and stability, as well as to enhance the penetration of active ingredients into the skin, which can improve their effectiveness. Combining steareth-20 with hesperidin methyl chalcone (HMC) in a topical formulation at concentrations of 1-5% can help stabilize and evenly distribute oil-in-water emulsions that contain HMC, solubilizing the HMC in water-based formulations and enhancing its penetration into the skin.

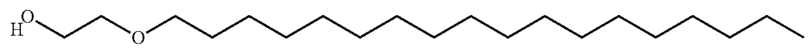

Dipeptide valyl-trytophane is a peptide consisting of two amino acids, Valine and Tryptophan (the chemical structures of each of which are shown and labeled below, valine being described in greater detail further below), joined together by a peptide bond. It is commonly used in skincare products due to its ability to improve the appearance of aging skin. Dipeptide valyl-tryptophane can stimulate collagen production in the skin which can help to improve skin elasticity and reduce the appearance of fine lines and wrinkles, and it also has antioxidant properties that can help to protect the skin against environmental stressors, such as UV radiation and pollution. It can also can improve skin texture by increasing hydration levels and promoting cell turnover, resulting in smoother and more radiant-looking skin, while also reducing the appearance of dark spots and hyperpigmentation, making it useful for people with uneven skin tone. It is typically used in small concentrations of 1% or less, however higher concentrations may be used depending on the particular formulation or intended effects.

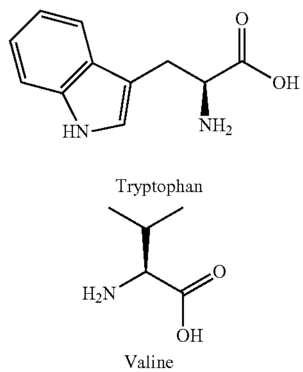

Tryptophan

Valine

In combination with HMC and steareth-20 (described above), dipeptide valyl-tryptophane works synergistically to provide multiple benefits for the skin. The dipeptide valyl-tryptophane and hesperidin methyl chalcone can work together to improve skin texture, reduce the appearance of dark spots and hyperpigmentation, and protect against environmental stressors. Steareth-20 helps to ensure that the active ingredients are evenly distributed on the skin, allowing them to work more effectively. Overall, such a topical formulation can help to promote healthy, radiant-looking skin.

Chlorhexidine gluconate (CHX), the chemical structure of which is shown below, is an antiseptic and disinfectant that is commonly used in healthcare settings to reduce the risk of infection. It is also used in some topical skincare products for its antimicrobial properties. The inclusion of chlorhexidine in a skincare product can provide several benefits for the skin, particularly in terms of antimicrobial protection. As an antiseptic and disinfectant, chlorhexidine can help to reduce the risk of infection and prevent the growth of bacteria and other microorganisms on the skin. This can be particularly beneficial for people with acne-prone skin, as chlorhexidine can help to reduce the number of acne-causing bacteria on the skin, leading to fewer breakouts. Additionally, chlorhexidine can be useful for wound care and can help to promote healing by preventing infections.

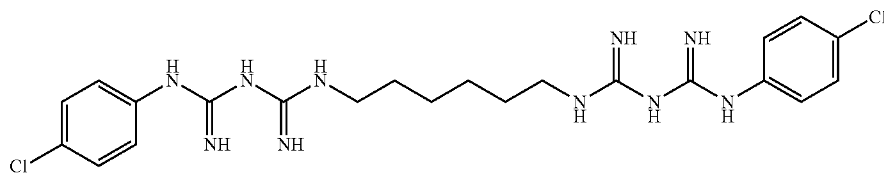 [SMILES: N=C(NCCCCCCNC(=N)NC(=N)Nc1ccc(Cl)cc1)NC(=N)Nc1ccc(Cl)cc1]

Grapeseed oil is derived from the seeds of grapes and contains several active compounds that can provide benefits for the skin in topical formulations, including linoleic acid, proanthocyanidins, tocopherols, resveratrol, and oligomeric proanthocyanidin complexes.

Proanthocyanidins are a group of naturally occurring flavonoid compounds that are found in many fruits, vegetables, and plant extracts. They are powerful antioxidants that can help to protect the skin from damage caused by free radicals and UV radiation. Oligomeric proanthocyanidin complexes (OPCs) are a specific type of proanthocyanidin that are found in grape seed extract and pine bark extract. OPCs are particularly potent antioxidants that have been shown to improve skin elasticity, reduce the appearance of fine lines and wrinkles, and improve skin hydration. In topical formulations, proanthocyanidins and OPCs can provide several benefits for the skin. Their antioxidant properties can help to protect the skin from damage caused by environmental stressors and prevent premature aging. They can also help to improve skin texture, reduce the appearance of hyperpigmentation, and promote overall skin health. Additionally, OPCs have been shown to be particularly effective at improving skin hydration and elasticity, making them a valuable ingredient in anti-aging formulations.

Resveratrol, the chemical structure of which is shown below, is a naturally occurring polyphenol that is found in the skin of grapes, berries, and other plants. It has been shown to have a range of beneficial effects when used in topical formulations. One of the primary benefits of resveratrol is its antioxidant activity. It can help to protect the skin from damage caused by free radicals and UV radiation, which can lead to premature aging and skin damage. Resveratrol also has anti-inflammatory properties, which can help to reduce redness and irritation and soothe the skin. resveratrol can be effective at concentrations as low as 0.1%, although higher concentrations may provide greater benefits; the particular concentration used may be adjusted based on the intended formulation and benefits, or the combination with other ingredients.

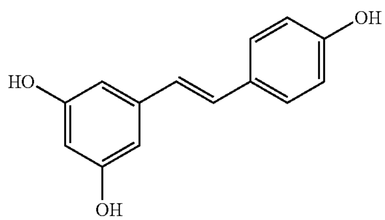 [SMILES: Oc1ccc(/C=C/c2cc(O)cc(O)c2)cc1]

Shea butter is a fat extracted from the nuts of the African shea tree (*Vitellaria paradoxa*). It is composed of several fatty acids, including oleic acid, stearic acid, linoleic acid, palmitic acid, and arachidic acid, the chemical structure of each of which is shown and labeled below. Shea butter also contains several other components, including vitamins A and E, as well as plant sterols and polyphenols. The exact composition of shea butter can vary depending on factors such as the geographic region where it is produced and the processing methods used. However, the fatty acid profile is relatively consistent and contributes to the unique properties of shea butter as a skincare ingredient.

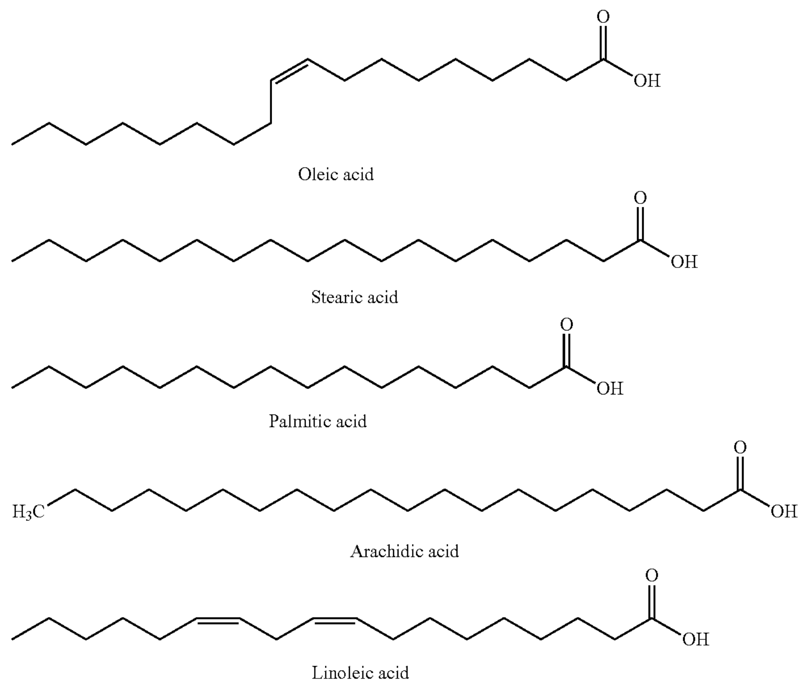

Oleic acid

Stearic acid

Palmitic acid

Arachidic acid

Linoleic acid

Linoleic acid, the chemical structure of which is shown above, is an omega-6 fatty acid that has several topical applications for the skin. One of its main benefits is its ability to help strengthen the skin barrier, which can help to reduce transepidermal water loss and keep the skin hydrated. Additionally, linoleic acid has anti-inflammatory properties that can help to soothe irritated skin and reduce redness. Linoleic acid has also been shown to help reduce the appearance of acne and improve skin texture, likely due to its ability to regulate sebum production. When combined with other ingredients in topical formulations, linoleic acid can provide even greater benefits for the skin. For example, combining linoleic acid with niacinamide can help to improve skin texture and reduce the appearance of hyperpigmentation. Combining linoleic acid with antioxidants like vitamin C can help to protect the skin from damage caused by free radicals and UV radiation. Finally, combining linoleic acid with ceramides can help to strengthen the skin barrier even further and reduce the appearance of fine lines and wrinkles. Overall, the topical applications of linoleic acid are wide-ranging and can be further enhanced when combined with other beneficial ingredients in well-formulated skincare products.

Olive fruit oil is a natural ingredient that has been used in topical skincare formulations for centuries. It contains several active components that provide numerous benefits to the skin. One of the primary active ingredients in olive fruit oil is squalene (the chemical structure of which is shown below), a natural emollient that can help to hydrate and soften the skin. Squalene is easily absorbed into the skin, helping to restore the skin's natural moisture barrier and protect it against environmental damage. It is also an antioxidant, meaning it can help to reduce the appearance of fine lines and wrinkles, as well as prevent free radical damage to the skin. Another important active ingredient in olive fruit oil is oleic acid, a fatty acid that can help to nourish and soothe the skin. Oleic acid has been shown to help reduce inflammation in the skin, making it useful for those with sensitive or irritated skin. It can also help to improve skin texture and reduce the appearance of acne scars and other blemishes. Olive fruit oil also contains a range of other beneficial components, including vitamin E, polyphenols, and phytosterols. Vitamin E is an antioxidant that can help protect the skin from free radical damage and reduce the appearance of fine lines and wrinkles. Polyphenols are also antioxidants that can help to reduce inflammation and improve skin elasticity. Phytosterols are compounds that can help to strengthen the skin's natural barrier, reducing moisture loss and improving overall skin health. The optimal concentration of olive fruit oil in topical formulations varies depending on the specific product and desired effects, but is typically between 1-10%.

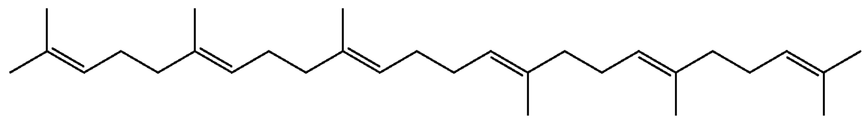

Squalene

Apricot kernel oil is a natural ingredient that is commonly used in topical skincare formulations because of its numerous beneficial properties. It contains several active components that provide a range of benefits to the skin. One of the primary active ingredients in apricot kernel oil is linoleic acid, an essential fatty acid that helps to strengthen the skin's natural barrier and improve overall skin health. Linoleic acid is also a natural anti-inflammatory, making it useful for those with sensitive or irritated skin. Additionally, it can help to regulate the production of sebum, the oil that can clog pores and contribute to acne. Another important active ingredient in apricot kernel oil is oleic acid, a fatty acid that can help to nourish and moisturize the skin. Oleic acid is easily absorbed into the skin, helping to restore the skin's natural moisture barrier and protect it against environmental damage. It can also help to improve skin texture and reduce the appearance of fine lines and wrinkles. Finally, apricot kernel oil contains a range of other beneficial components, including vitamins A and E, as well as phytosterols. Vitamin A is a powerful antioxidant that can help to reduce the appearance of fine lines and wrinkles, while vitamin E is another antioxidant that can help to protect the skin from free radical damage. Phytosterols are compounds that can help to strengthen the skin's natural barrier, reducing moisture loss and improving overall skin health. The optimal concentration of apricot kernel oil in topical formulations varies depending on the specific product and desired effects, but is typically between 1-10%.

Rapeseed oil is a popular vegetable oil that is pressed from the seeds of various Brassicaceae cultivars, and is rich in several active components that offer numerous benefits when used in topical formulations. Rapeseed oil is an excellent source of both omega-3 and omega-6 fatty acids, which are essential for maintaining healthy skin. These fatty acids help to improve skin barrier function, reduce inflammation, and increase skin hydration. Common concentrations of omega-3 and omega-6 fatty acids in rapeseed oil range from 20-50% and can be added to formulations at a concentration of 0.5-5%. Rapeseed oil contains high levels of vitamin E (described in further detail above, see tocopherols and tocotrienols), a powerful antioxidant that helps to protect the skin from damage caused by free radicals. Vitamin E also has anti-inflammatory properties and can help to reduce the appearance of fine lines and wrinkles. Common concentrations of vitamin E in rapeseed oil range from 10-20% and can be added to formulations at a concentration of 0.5-2%. The oil also contains phytosterols, which are plant compounds that have been shown to have anti-inflammatory and antioxidant properties. They can help to reduce redness and irritation in the skin, improve skin elasticity, and promote a more even skin tone. common phytosterols found in rapeseed oil are beta-sitosterol and campesterol, the chemicals structures of each of which are shown and labeled below. These phytosterols are plant-based compounds that have a similar structure to cholesterol and can help lower cholesterol levels in the body. Beta-sitosterol is the most abundant phytosterol found in rapeseed oil, and it has been shown to have anti-inflammatory properties and may help improve symptoms of benign prostatic hyperplasia (BPH). Campesterol is another common phytosterol found in rapeseed oil, and it has been shown to have potential anti-cancer properties.

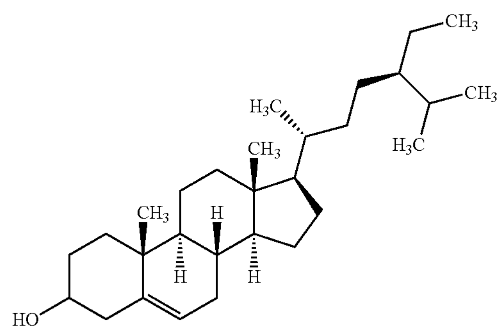

Beta-sitosterol

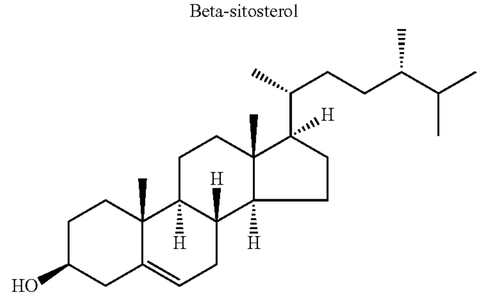

Camposterol

Licorice root extract is a complex mixture of various compounds often used in food and traditional medicine, extracted from the roots of the *Glycyrrhiza glabra* plant. Glycyrrhizin is the main active component of licorice root extract and has been shown to have anti-inflammatory and antioxidant properties. It can help to reduce redness and irritation in the skin and protect against free radical damage. The extract also comprises glabridin and liquiritin, flavonoids that has been shown to have anti-inflammatory and skin-brightening properties. These compounds can help to reduce the appearance of hyperpigmentation and dark spots, and generally promote a more even skin tone. A concentration of up to 2% licorice root extract is often used in topical formulations, and the chemical structures for the described active ingredients are shown and labeled below.

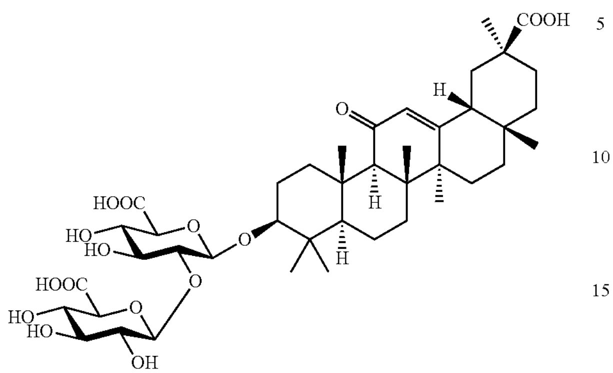

Glycyrrhizin

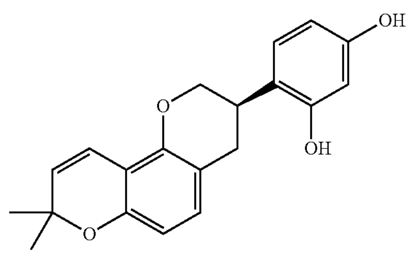

Glabridin

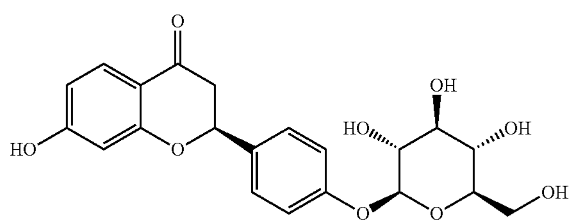

Liquiritin

*Althaea officinalis*, also known as marshmallow root, is a plant commonly used in traditional medicine for its healing properties. In topical formulations, *Althaea officinalis* extract is believed to provide a range of benefits for the skin due to its active components. Marshmallow root extract contains high amounts of polysaccharides, which have been shown to have hydrating and anti-inflammatory properties. They can help to soothe and moisturize the skin, reduce redness and irritation, and improve the overall appearance of the skin. Marshmallow root extract also contains flavonoids, including quercetin and kaempferol (the chemical structures of each of which are shown and labeled below), which have antioxidant and anti-inflammatory properties. They can help to protect the skin against free radical damage and reduce inflammation, redness, and irritation. Tannins are another active component of marshmallow root extract that have astringent and anti-inflammatory properties. They can help to tighten and firm the skin, reduce the appearance of pores, and reduce inflammation and irritation. A concentration of up to 2% is often used in topical formulations, though some formulations may use higher concentrations according to a particular intended effect or combination with other ingredients.

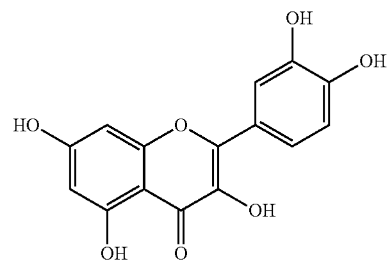

Quercetin

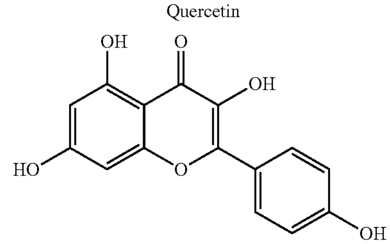

Kaempferol

Rice bran extract is derived from the outer layer of rice grains and is rich in vitamins, minerals, and antioxidants. In topical formulations, rice bran extract provides a range of benefits for the skin due to its active components. Ferulic acid, the chemical structure of which is shown and labeled below, is a powerful antioxidant that helps to protect the skin against free radical damage and reduce the signs of aging. It can also help to brighten the skin and reduce the appearance of hyperpigmentation. Gamma oryzanol is a is a mixture of lipid compounds found in rice bran extract that has been shown to have anti-inflammatory and antioxidant properties. It can help to reduce redness and inflammation in the skin, improve skin elasticity, and protect against free radical damage. The primary constituent compounds of gamma-oryzanol are Cycloartenyl ferulate (also called Oryzanol A), 24-Methylenecycloartanyl ferulate (also called Oryzanol C), and Campesteryl ferulate; their respective chemical structures are shown and labeled below. Rice bran extract also comprises phytic acid (the chemical structure of which is shown and labeled below), a natural exfoliant that helps to remove dead skin cells and promote cell turnover. It can help to brighten the skin and reduce the appearance of fine lines and wrinkles. Typical concentration of rice bran extract range as high as 1-2%, though the exact concentration may vary based on a desired effect or based on other ingredients present, and May 5 be higher.

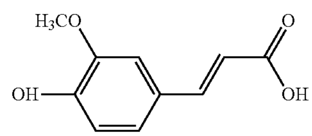

Ferulic acid

-continued

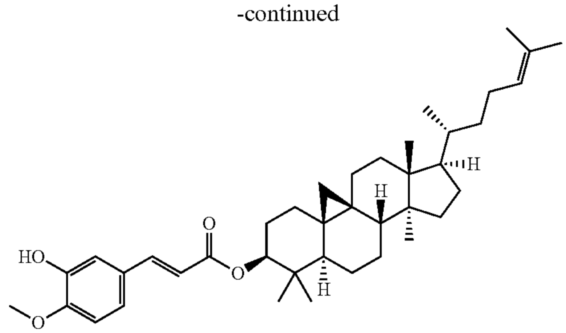

Cycloartenyl ferulate

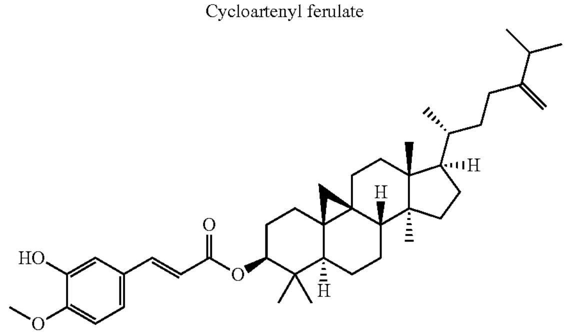

24-Methylenecycloartanyl ferulate

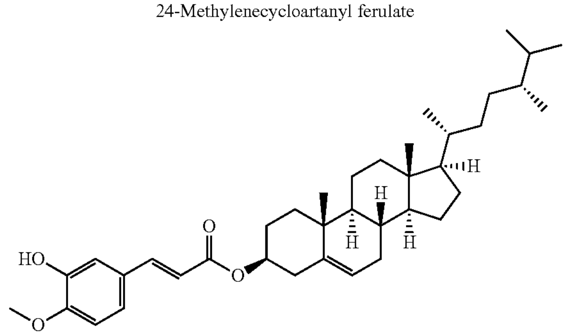

Camposterol ferulate

-continued

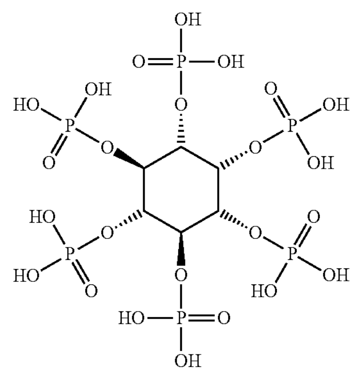

Phytic acid

Polyglyceryl-3 diisostearate, the chemical structure of which is shown below, is a chain of three glycerol molecules with an isostearate chain on each end. Polyglyceryl-3 diisostearate is primarily used as an emulsifier, helping to mix oil and water-based ingredients together to create a stable and uniform product. It is often used in creams, lotions, and other emulsions, and it can also be used as a co-emulsifier in conjunction with other emulsifiers to improve their effectiveness. Polyglyceryl-3 diisostearate also has emollient properties, helping to soften and smooth the skin. It can be used in moisturizers and other skincare products to provide hydration and improve the texture of the skin.

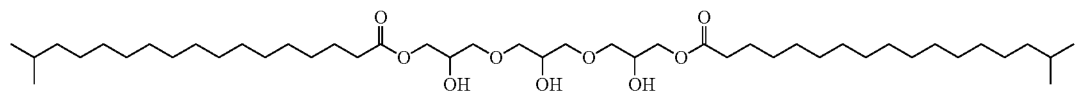 [SMILES: CC(C)CCCCCCCCCCCCCCC(=O)OCC(O)COCC(O)COCC(O)COC(=O)CCCCCCCCCCCCCCC(C)C]

Butyl avocadate, the chemical structure of which is shown below, is an ester of butyl alcohol and fatty acids extracted from avocado oil, including oleic acid, palmitoleic acid, linoleic acid, stearic acid, and palmitic acid (which are illustrated and described above). It is a natural ingredient that is commonly used in topical skincare formulations because of its numerous beneficial properties. It has been shown to help regulate the production of sebum, the oil that can clog pores and contribute to acne, as well as reduce inflammation, redness, and irritation in the skin. Additionally, butyl avocadate acts as a natural emollient that can help to hydrate and soften the skin, making it particularly useful for those with dry or sensitive skin. The ingredient also contains antioxidants that can help protect the skin from free radical damage, reduce the appearance of fine lines and wrinkles, and promote a more youthful, radiant complexion. Lastly, butyl avocadate has some sun-protective effects, helping to prevent UV damage and reduce the risk of skin cancer. The optimal concentration of butyl avocadate in topical formulations varies depending on the specific product and desired effects but is typically between 0.5-2%.

Retinol (also called vitamin A1), the chemical structure of which is shown below, is the primary form of vitamin A that is preferentially absorbed in the human body and is commonly found in a number of animal-based dietary sources including fish, dairy, and animal livers. When used topically (generally in a cream or gel-based solution with a 10% concentration of retinol, though higher or lower concentrations may be used depending on the application), retinol can help to stimulate collagen production to improve skin texture, reduce the appearance of fine lines and wrinkles, and improve the overall smoothness of the skin. Retinol also increases cell turnover, which improves skin recovery by stimulating the production of new keratinocytes and increasing skin thickness. Retinol has also shown benefits for skin hydration and hyperpigmentation, where it reduces localized melanin overproduction and helps retain moisture in the skin tissues to aid in recovery and improve skin firmness and texture.

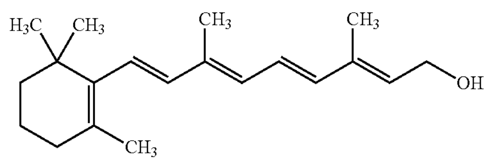 [SMILES: CC1=C(/C=C/C(C)=C/C=C/C(C)=C/CO)C(C)(C)CCC1]

Polyacrylic acid (also known under the trade name Carbomer), the chemical structure of which is shown below, is a water-soluble anionic polymer chain of acrylic acid; the charged side chains bind to water molecules causing the polymer to retain water and expand in size, a property which is useful in a number of topical applications. By improving skin hydration, polyacrylic acid can help soften and smooth the skin's surface, which can improve the overall texture and appearance of the skin, and can help increase the volume of the skin, which can temporarily reduce the appearance of fine lines and wrinkles. This also can have a cooling and soothing effect on the skin, which can help reduce redness and irritation. Polyacrylic acid can also be used as a vehicle to deliver other active ingredients deeper into the skin, where they can be more effective, similar to hyaluronic acid as described below. At concentrations of 0.1-0.5%, polyacrylic acid can act as a humectant, helping to attract and retain water in the skin. This can help improve skin hydration and reduce dryness. Raising the concentration to 1-5% results in a plumping effect on the skin, helping to temporarily reduce the appearance of fine lines and wrinkles. It can also help improve the texture and overall appearance of the skin. At still higher concentrations of 5-10%, polyacrylic acid can act as a thickening agent, helping to give skincare products a more luxurious texture. It can also help improve the delivery of other active ingredients.

Polyacryclic acid can be combined with palmitoyl tripeptides in a synergistic formulation, taking advantage of the hydrating effects and recovery-boosting properties of each ingredient. Polyacrylic acid can help to reduce moisture loss from the skin, while palmitoyl tripeptide-1 can stimulate collagen production and improve skin elasticity. Together, these ingredients can help to improve skin hydration and reduce dryness, as well as improve the texture of skincare products, making them easier to apply and more comfortable to wear. This can help to improve the overall texture of the skin, making it look and feel smoother and more even. Palmitoyl tripeptide-1 can stimulate collagen production and improve skin elasticity, which can help to reduce the appearance of fine lines and wrinkles. By combining this ingredient with polyacrylic acid, you could potentially enhance its anti-aging benefits. Overall, combining polyacrylic acid with palmitoyl tripeptide-1 in a topical formulation could potentially provide a range of benefits for the skin, including improved hydration, texture, and anti-aging benefits.

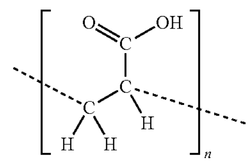

Butylene glycol is a group of four structural isomers of butanediol, the chemical structure of each of which is shown below. The two middle isomers shown (1,3-butanediol and 1,4-butanediol, respectively) are commonly used in skincare products, while 1,2-butanedial (the leftmost structure shown) is commonly used as a flavoring agent in food products and 2,3-butanediol (the rightmost shown) is used in plastics and pesticides. 1,3-butanediol is a clear, colorless liquid that is highly soluble in water. It is commonly used in skincare formulations as a humectant and moisturizer, helping to attract and retain water in the skin. It can also help to improve the texture and spreadability of skincare products, making them easier to apply and more comfortable to wear. 1,4-butanediol is a clear, colorless liquid that is less soluble in water than 1,3-butylene glycol. It is commonly used in skincare formulations as a solvent and viscosity-reducing agent, helping to improve the texture and spreadability of skincare products. It can also act as a humectant, helping to attract and retain water in the skin.

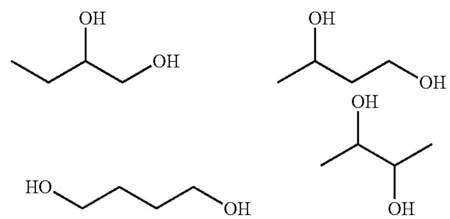

Pentylene glycol (chemical name 1,5-pentanediol), the chemical structure of which is shown below, is a colorless viscous liquid often used as a plasticizer or emulsifying agent and is a versatile ingredient that is commonly used in skincare products due to its ability to function as a moisturizer, preservative, and solvent. The concentration of pentylene glycol in skincare products can vary depending on the specific product and its intended use. At low concentrations of 0.1-1%, pentylene glycol can act as a humectant, helping to attract and retain moisture in the skin. It can also improve the spreadability and texture of skincare products, making them easier to apply and more comfortable to wear. At higher concentrations of 1-5%, pentylene glycol can act as a preservative, helping to prevent the growth of harmful bacteria and fungi in skincare products. It can also help to improve the efficacy of other preservatives in the formulation, increasing the shelf life of the product. At still higher concentrations in the range of 5-10%, pentylene glycol can act as a solvent, helping to dissolve other ingredients in the formulation. It can also act as a co-solvent, enhancing the solubility of other active ingredients in the product.

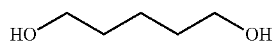

Pullulan, the chemical structure of which is shown below, is a natural polysaccharide produced by the fermentation of starch by the fungus *Aureobasidium pullulans*. It is commonly used in topical formulations due to its ability to provide a range of benefits to the skin and its relative non-toxicity that is well-tolerated by the human body, and it is also biodegradable which makes for a more environmentally-friendly product. Pullulan has the ability to form a thin, transparent film over the skin, which can help to lock in moisture and prevent dehydration. This film can also help to improve the skin's texture and appearance, making it look smoother and more hydrated. Pullulan has been shown to have anti-aging properties, including the ability to improve the skin's elasticity and reduce the appearance of fine lines and wrinkles. This is due in part to its ability to form a film over the skin, which can help to improve the skin's firmness and tone. Pullulan has also been shown to have antioxidant properties, which can help to protect the skin from damage caused by free radicals and environmental stressors. This can help to prevent premature aging and promote overall skin health.

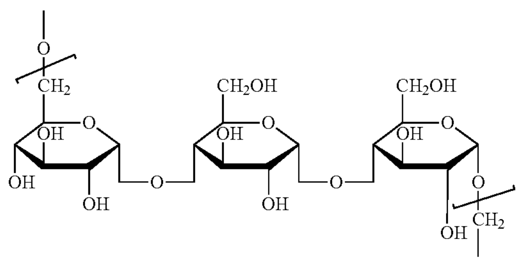

*Nannochloropsis oculata* is a type of microalgae that is rich in nutrients and bioactive compounds, and its extract has various uses in different industries. In the skincare industry, *Nannochloropsis oculata* extract is used in topical formulations due to its ability to provide a range of benefits to the skin. The extract contains polysaccharides such as laminarin and fucoidan (the chemical structures of which are shown and labeled below), and other compounds that can help to hydrate and moisturize the skin. This can help to improve the skin's texture and appearance, making it look smoother and more supple. The extract has also been shown to have anti-aging properties, including the ability to stimulate collagen production and reduce the appearance of fine lines and wrinkles. This can help to improve the skin's elasticity and firmness, and promote a more youthful appearance. The extract contains pigments such as chlorophyll and carotenoids, which can help to brighten and even out the skin tone. This can help to reduce the appearance of dark spots and hyperpigmentation, and promote a more radiant complexion, and has antioxidant properties, which can help to protect the skin from damage caused by free radicals and environmental stressors. This can help to prevent premature aging and promote overall skin health. The extract is also rich in omega-3 fatty acids such as eicosapentaenoic acid (EPA) and docosahexaenoic acid (DHA), the structures for which are shown and labeled below, which can help to improve the skin's barrier function and reduce inflammation. This can help to prevent dryness and irritation, and promote overall skin health.

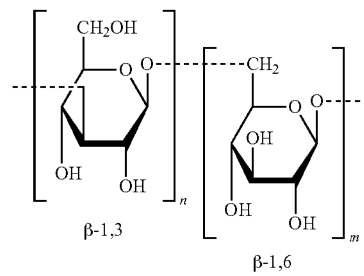

Laminarin

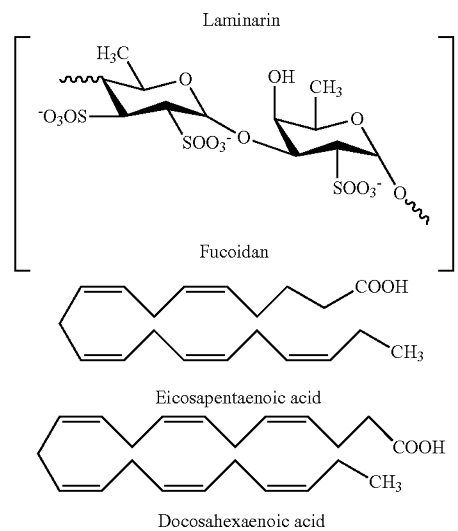

Fucoidan

Eicosapentaenoic acid

Docosahexaenoic acid

Macadamia oil is a rich, nourishing oil that is derived from the nuts of the macadamia tree. It contains a range of active components that are beneficial for the skin, including monounsaturated fatty acids, particularly oleic acid (omega-9) and palmitoleic acid (omega-7), the chemical structures of which are shown below. These fatty acids help to moisturize and nourish the skin, and can help to improve the skin's barrier function. Macadamia oil also contains phytosterols, which are plant-based compounds that are similar in structure to cholesterol. Phytosterols can help to soothe and calm the skin, reduce inflammation, and improve the skin's natural protective barrier. Macadamia oil is rich in tocopherols, powerful antioxidants that help to protect the skin from damage caused by free radicals and environmental stressors. Vitamin E tocopherols and tocotrienols can also help to moisturize and nourish the skin, and support overall skin health, and are described in greater detail below. Macadamia oil also contains squalene, a natural compound that is found in human sebum. Squalene can help to moisturize and protect the skin, and improve its texture and appearance, and is described in greater detail below.

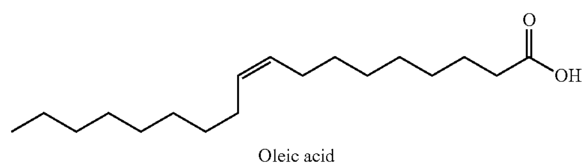

Oleic acid

-continued

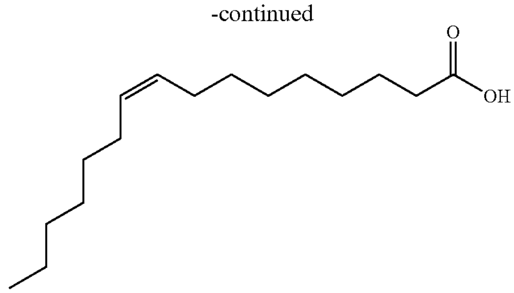

Palmitoleic acid

Lysine, the chemical structure of which is shown below, is an essential amino acid (meaning it cannot be synthesized by the human body and must be acquired directly from dietary sources) that plays a critical role in the manufacture of proteins and the cross-linking of collagen peptides, and has also been shown to have a number of benefits when applied topically to the skin. Lysine has been shown to be effective in the treatment of cold sores, reducing the severity and duration of cold sores when applied topically in concentrations of 1-6%. When used in higher concentrations up to 10%, lysine has been shown to reduce signs of aging and improve wound healing by promoting collagen synthesis and increasing the production of growth factors that are important for tissue repair.

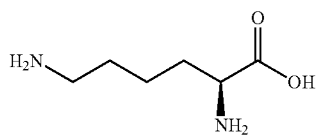

Tripeptide-10 citrulline, the chemical structure of which is shown below, is a synthetic peptide combining arginine, lysine, isoleucine, and citrulline; it regulates the production of collagen and improves the organization of collagen structures, helping to restore the skin's suppleness and resiliency. Topical formulations including tripeptide-10 citrulline have been shown to improve suppleness as much as 54% within four weeks of treatment. The optimal dose or concentration of tripeptide-10 citrulline in topical applications can depend on the specific use case and the formulation of the product. In general, concentrations of 0.5% to 2% tripeptide-10 citrulline are commonly used in skincare products.

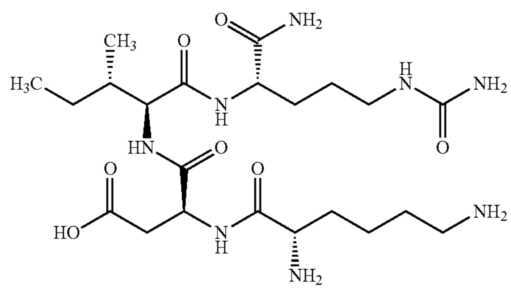 [SMILES: CC[C@H](C)[C@H](NC(=O)[C@H](CC(=O)O)NC(=O)[C@@H](N)CCCCN)C(=O)N[C@@H](CCCNC(N)=O)C(N)=O]

Undecylenoyl phenylalanine (UP), the chemical structure of which is shown below, is an ingredient commonly used in skincare products for its potential to lighten and even out skin tone. UP lightens skin by inhibiting eumelanin synthesis and inactivating tyrosinase, as well as inhibiting the action of adenyl cyclase, thereby decreasing melanocyte activity and reducing melanin production. This can help reduce the appearance of dark spots, age spots, and hyperpigmentation, resulting in a brighter, more even skin tone. Topical application with concentrations ranging from 0.5-5% (depending on the particular formulation and intended benefits) has shown skin lightening effects in as little as 7 days of treatment, with gradual reduction in age-related imperfections and improved complexion over 2 months. UP has also been found to have some UV protective properties which can help prevent skin damage caused by sun exposure, and when used in conjunction with moisturizing ingredients UP has been shown to increase collagen production in the skin, which can help reduce the appearance of fine lines and wrinkles and help improve skin texture and firmness.

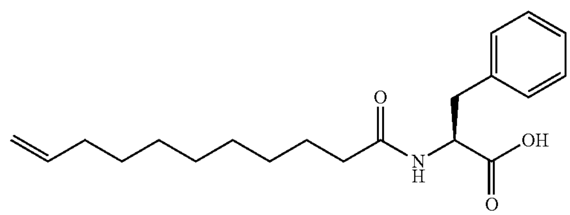 [SMILES: C=CCCCCCCCCC(=O)N[C@@H](Cc1ccccc1)C(=O)O]

Arginine, the chemical structure of which is shown below, is an amino acid generally considered "conditionally essential", common in all protein-rich foods. In addition to its nutritional role, topical application of arginine has been shown to reduce inflammation and signs of aging, improve hydration, protect against UV-related damage, and stimulate wound healing. L-arginine is a metabolic precursor to creatine, which plays a key role in the regeneration of cellular ATP and tissue recovery. Arginine has been found to stimulate collagen production, which can help improve the healing of wounds and reduce the appearance of scars as well as improving skin elasticity. Typical concentrations of arginine usually range from 1-5%, though some formulations may use higher or lower concentrations depending on factors such as application method, targeted benefits, and other ingredients present.

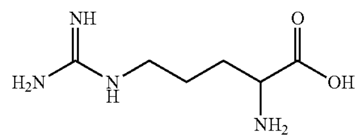 [SMILES: N=C(N)NCCCC(N)C(=O)O]

Proline, the chemical structure of which is shown below, is an amino acid essential in the production of collagen, which is the building block of connective tissues throughout the body and vital in maintaining proper skin firmness and appearance. L-proline has the highest water-binding capacity of the amino acids found in the body, making it an excellent supplement for improving skin hydration and restoring firmness and texture. In combination with arginine, proline restores and rejuvenates the skin through these complementary processes, resulting in rapid healing and restoration of the skin. A topical formulation using both arginine and proline can provide a range of potential benefits for the skin, such as improving hydration, reducing the appearance of fine lines and wrinkles, and supporting healthy skin cell turnover. Typical concentrations of arginine usually range from 0.1-5%, though some formulations may use higher or lower concentrations depending on factors such as application method, targeted benefits, and other ingredients present; in such a topical formulation, arginine may be present in a 1:1 ratio with proline, or one of the two may be present in a higher ratio depending on the intended benefits. In a typical formulation, additional ingredients such as water and glycerin may be used to help to hydrate the skin, while the arginine and proline support healthy skin cell function and collagen synthesis. Sodium hyaluronate helps to further boost hydration, while xanthan gum may be used as a thickener to improve the texture of the product. Sodium hydroxide may be added to adjust the pH of the formulation, and phenoxyethanol may be used as a preservative to prevent the growth of harmful bacteria and fungi.

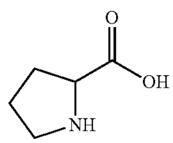

Glycine, the chemical structure of which is shown below, is the simplest amino acid and has been shown to have moisturizing and anti-inflammatory properties. It can help soothe and calm the skin and may also help support healthy skin function. When used in combination with arginine and proline in a topical formulation, the three amino acids work synergistically together to maximize their individual benefits and provide a more comprehensive approach to skin care. For example, a formulation containing arginine, proline, and glycine may help improve skin hydration, support collagen synthesis, reduce the appearance of fine lines and wrinkles, and soothe and calm the skin. In such an application, the specific concentration of each active ingredient may be adjusted to optimize its benefits relative to the other constituent amino acids; for example, a typical skincare cream or gel may comprise 2% arginine and 1% each of proline and glycine (or in a more-concentrated formulation, 4% and 2%, respectively). Arginine is known to play a key role in the synthesis of collagen, a protein that provides structure and elasticity to the skin. Therefore, a higher concentration of arginine in the formulation may help to support collagen synthesis and improve skin elasticity; Proline and glycine are also important amino acids for collagen synthesis and can help improve skin elasticity and reduce the appearance of fine lines and wrinkles. However, their roles in collagen synthesis are not as prominent as arginine. Therefore, a slightly lower concentration of proline and glycine in the formulation may still provide benefits to the skin, while allowing for a higher concentration of arginine to support collagen synthesis.

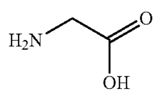

Copper acetate (also known as cupric acetate or the more precise nomenclature of copper (II) acetate), the chemical structure of which is shown below, is a dark-green crystalline copper compound used as a pigment and topical fungicide throughout history. Copper acetate is often used in cosmetic and skincare products, such as anti-aging creams, moisturizers, and wound healing products. It can also be used in medical applications, such as wound dressings, to promote healing and prevent infections. Copper acetate has antioxidant properties, which means it can help protect the skin from damage caused by free radicals, which are unstable molecules that can cause cell damage and premature aging; it may also help promote wound healing by stimulating the growth of new blood vessels and promoting the production of collagen, a protein that is important for skin structure and elasticity. Copper acetate has been shown to have anti-microbial properties, which means it can help kill or inhibit the growth of certain bacteria and fungi that can cause skin infections, and it is known to have been used in this role by various cultures at least as far back as the bronze age. Combining copper acetate with a mixture of arginine, proline, and glycine in a topical formulation may offer several benefits for the skin, including enhanced collagen production, increased antioxidant activity, improved wound healing, and enhanced anti-inflammatory and anti-microbial properties. Typically, only small amounts of copper acetate are required to experience these synergistic benefits, and an exemplary skincare product such as a cream might comprise 0.05% copper acetate in combination with the above exemplary concentration of 2%/1%/1% arginine, proline, and glycine, respectively. While copper acetate has many potential benefits for the skin, it is typically used in very small amounts in skincare formulations due to its potency and potential to cause skin irritation at higher concentrations. Copper acetate is also a comparatively expensive ingredient, so using it in small amounts can help keep the cost of the skincare product down while still providing the benefits of its synergy with the amino acids described above.

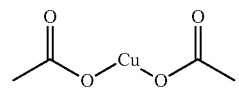

*Silybum marianum*, known by various common names including milk thistle, Scotch thistle, and Saint Mary's thistle, is a plant of the family Asteraceae originally native to southern Europe but now found throughout the world. Various plant parts and extracts of milk thistle have been used in traditional medicine in various cultures for centuries, in particular the extract silymarin, a polyphenol which comprises the compounds silibinin A and B, the chemical structures of which are shown below (silibinin A at left, silibinin B at right). Silymarin works in conjunction with other free radical scavengers such as glutathione and tocopherols, improving the capture of free radicals and reducing oxidative stress. Silymarin has also been shown to specifically reduce the process of lipid peroxidation, protecting lipids against oxidative damage that inhibits the uptake of fat-soluble compounds, making for a potent synergy with tocopherols that boosts their efficacy as antioxidants while also improving their bioavailability. When applied topically, silymarin has also been shown to have anti-inflammatory properties and dramatically reduces the occurrence of acne lesions in daily therapeutic doses around 210 mg.

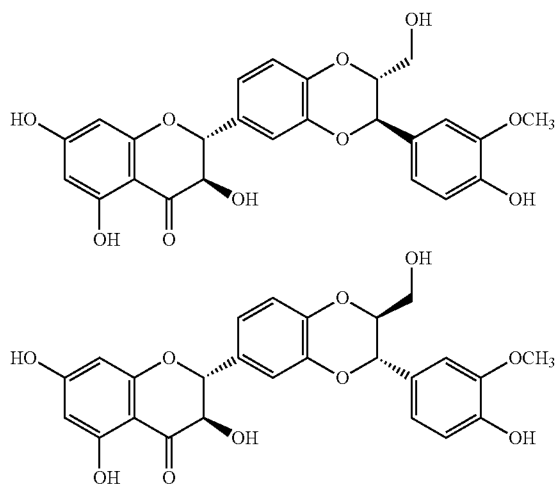

Carnosine, the chemical structure of which is shown below, is a dipeptide of beta-alanine and histidine, found exclusively in meats and other animal-based dietary sources (there are no known plant-based dietary sources for carnosine). Carnosine has a number of antioxidant properties including both scavenging free radicals as well as unsaturated aldehydes produced by cellular lipid membranes during oxidative stress via the process of lipid auto-peroxidation. It also has anti-glycation properties, reducing the formation of glycation end-products that contribute to premature aging effects and a variety of degenerative disorders such as Alzheimer's and diabetes. Other benefits of carnosine include buffering the pH of muscle tissue, functioning as a neurotransmitter (high levels of carnosine are found in neural tissue), and slowing a number of aging processes by increasing the Hayflick limit (the programmed limit on the number of times a cell population will divide before cell division ceases) in cells and slowing the telomere shortening rate. These properties make carnosine a useful adjunct in combination with silymarin and tocopherols, where their respective antioxidant and anti-aging benefits work synergistically to complement each other. In test studies, topical applications of this synergistic mixture have been shown to improve skin health and reduce age-related wrinkles by as much as 27%.

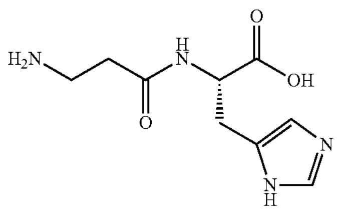 [SMILES: NCCC(=O)N[C@@H](Cc1cnc[nH]1)C(=O)O]

*Lactobacillus* is a genus of rod-shaped bacteria common to the gastrointestinal tract, many of which are marketed as a probiotic supplement in a number of food products such as milk, yogurt, cheese, kefir, and other dairy products. *Lactobacillus* species are commonly used in fermented dairy and other food products such as sauerkraut, where they break down lactose and other sugars and produce lactic acid to impart a "tart" flavor characteristic of fermented foods. In topical applications, *Lactobacillus* may themselves be fermented to produce a nonliving lysate, which has been shown to provide a soothing effect and strengthen the skin's ability to function as a defensive layer against pathogens. This is due to encouragement of the microbiota living on the skin, where the *Lactobacillus* ferment lysate helps maintain an ideal mix of flora to reduce the occurrence and severity of a number of skin conditions caused by dysfunction of the skin barrier. The lysate inhibits the reproduction of harmful bacteria on the skin to regulate the population, and also regulates the production of skin oils to reduce irritation from under- or over-production.

*Coffea canephora* is a species of coffee plant originally native to sub-Saharan Africa, also commonly known as *Coffea robusta*. In addition to being brewed as coffee (often roasted), the seeds of this plant contain a variety of compounds with therapeutic uses that can be extracted and used in formulations for internal or topical use, including antioxidants, alkaloids, amino acids, and volatile compounds. Extracts from green coffee beans (dried, un-roasted beans with the husks removed) have proven beneficial in skin care for protection from harmful effects of sun exposure, reducing cellulite formation, and improving complexion both in skin and hair care. Coffee bean extract has been shown to increase collagen production, improving skin firmness, hydration, and texture and contributing to overall skin health. The extract also acts as a diuretic, further contributing to skin benefits particularly in improving firmness and reducing the appearance of wrinkles.

Citric acid, the chemical structure of which is shown below, is a weak organic acid occurring naturally in a wide variety of fruits, notably those of the citrus family with lemons and limes having the highest naturally-occurring concentrations (as high as 8% by dry weight). It is commonly used as a food additive to impart a sour or "tart" flavor as an acidulant, as well as in various creams, gels, and liquids for cosmetic or topical medicinal purposes. It has astringent, exfoliating, and antioxidant properties, which make it a popular ingredient in a variety of topical applications; it is often used as a natural exfoliant in skincare products, such as facial scrubs and body washes. Its acidic properties help to slough away dead skin cells and unclog pores, leaving the skin looking smoother and more radiant. Citric acid can help to brighten the skin and reduce the appearance of age spots, sun damage, and other types of hyperpigmentation by inhibiting the production of melanin, the pigment that gives skin its color. Citric acid has antioxidant properties that can help to protect the skin from damage caused by free radicals, which can lead to premature aging. It is often used in anti-aging skincare products to help reduce the appearance of fine lines and wrinkles, and has a synergistic effect when combined with vitamin E and aloe gel. Citric acid can help to control excess oil production in the skin, which is a common cause of acne. It can also help to unclog pores and reduce inflammation, making it a popular ingredient in acne treatment products.

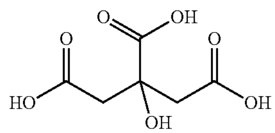 [SMILES: O=C(O)CC(O)(CC(=O)O)C(=O)O]

Allantoin, the chemical structure of which is shown below, is a diureide of glyoxylic acid, produced from uric acid during purine catabolismit may also be extracted from the leaves of the comfrey plant; comfrey leaves have been used for centuries to aid in skin healing and reducing swelling around minor injuries. While allantoin is also found in a number of plants including beets, chamomile, and tobacco seeds, therapeutic usage often relies on synthetically-produced allantoin for practical reasons. Allantoin is a natural humectant, helping to draw moisture to the skin and prevent dryness to improve skin hydration and leave the skin feeling soft and smooth. Allantoin has anti-inflammatory properties that can help to soothe and calm irritated or inflamed skin. It is often used in products for sensitive skin or skin conditions such as eczema or psoriasis, and it has been shown to enhance the healing of wounds and promote the growth of new tissue. It can help to improve skin elasticity and reduce the appearance of scars and stretch marks. Allantoin also has antioxidant properties that can help to protect the skin from damage caused by free radicals, which can lead to premature aging. It can help to reduce the appearance of fine lines and wrinkles and improve skin firmness and elasticity. These properties make it a useful agent in combination with aloe vera gel for improving skin health and reducing the long-term effects of oxidative damage.

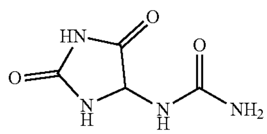 [SMILES: NC(=O)NC1NC(=O)NC1=O]

Dextran, the chemical structure of which is shown below, is a branched polysaccharide polymer originally isolated from wine and commonly produced at an industrial scale using bacterial cultures. Dextran has a number of medical uses including use as a blood plasma expander, an anti-coagulant, use in scaffold material for tissue engineering (such as during reconstructive surgery or for growing grafts for later implantation), as well as immunomodulation making it a useful adjunct in vaccines. Dextran is also a useful drug delivery vehicle, where it is use in combination with various compounds and targeted to specific tissues or cells in the body. This can increase the efficacy and reduce the toxicity of certain drugs, making it beneficial in combination with many ingredients for enhancing their respective effects.

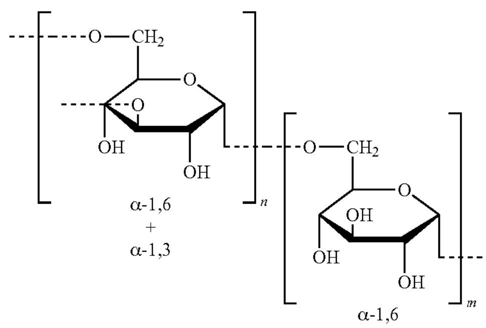

Nonapeptide-1 (also known as melanostatine), the chemical structure of which is shown below, is a peptide consisting of nine amino acids linked together by peptide bonds. Peptides are small chains of amino acids that play important roles in many biological processes in the body, including cell signaling, enzyme regulation, and structural support. Nonapeptides can have a variety of functions depending on their specific sequence and context. For example, some nonapeptides are involved in regulating the activity of hormones, neurotransmitters, or growth factors. Others can act as antimicrobial agents or immune modulators. One well-known nonapeptide is oxytocin, which is sometimes called the "love hormone" or "cuddle hormone" because it is released in the brain during social bonding activities such as hugging, kissing, or breastfeeding. Oxytocin also plays a role in childbirth, lactation, and sexual reproduction. Nonapeptides can be synthesized in the laboratory or isolated from natural sources such as plants, animals, or microorganisms. They have a wide range of potential applications in medicine, biotechnology, and materials science, including drug discovery, tissue engineering, and biosensors.

Nonapeptide-1 in particular is a synthetic peptide that is used in the cosmetic industry for its skin brightening properties. Nonapeptide-1 works by inhibiting the production of melanin, the pigment that gives skin its color. Melanin production is controlled by a number of different enzymes, and one of the key enzymes involved in this process is called tyrosinase. Nonapeptide-1 works by blocking the activity of tyrosinase, which in turn reduces the amount of melanin produced by the skin. This can help to even out skin tone and reduce the appearance of age spots, sun damage, and other types of hyperpigmentation. In addition to its skin brightening properties, nonapeptide-1 has been shown to have antioxidant and anti-inflammatory effects. These properties can help to protect the skin from damage caused by free radicals and reduce inflammation, which can contribute to skin aging.

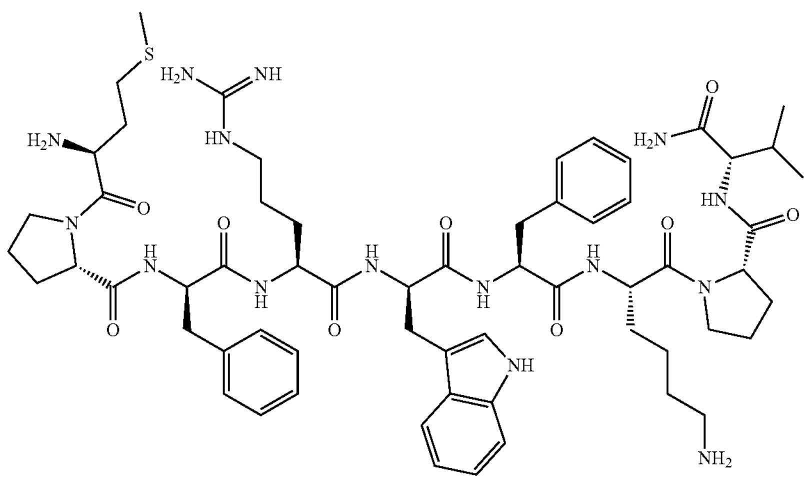 [SMILES: CSCC[C@H](N)C(=O)N1CCC[C@H]1C(=O)N[C@H](Cc1ccccc1)C(=O)N[C@@H](CCCNC(=N)N)C(=O)N[C@H](Cc1c[nH]c2ccccc12)C(=O)N[C@@H](Cc1ccccc1)C(=O)N[C@@H](CCCCN)C(=O)N1CCC[C@H]1C(=O)N[C@H](C(N)=O)C(C)C]

Dextran and nonapeptide-1 can work together in different ways, depending on the specific context or application. In some cases, dextran and nonapeptide can be used to improve the delivery of drugs to specific cells or tissues in the body. Dextran is a type of polysaccharide that can form a hydrogel or gel-like structure when mixed with water. This structure can be used to encapsulate drugs and protect them from degradation or elimination in the body. Nonapeptide-1, on the other hand, can bind specifically to certain types of cells or tissues, such as cancer cells or inflamed tissues. By attaching nonapeptide to the surface of dextran-based drug carriers, the carriers can be targeted to specific cells or tissues, increasing the efficacy and reducing the side effects of the drugs.

Dextran and nonapeptide can also be used together to promote wound healing. Dextran hydrogels have been shown to have excellent wound-healing properties, including the ability to absorb excess exudate (fluid) and create a moist environment that promotes tissue regeneration. Nonapeptide can stimulate the proliferation and migration of certain types of cells, including fibroblasts and endothelial cells, which are important for tissue repair and angiogenesis (the formation of new blood vessels). By combining dextran and nonapeptide, a wound dressing or scaffold can be created that enhances the natural healing processes of the body and accelerates the closure of the wound.

Niacinamide (also known as nicotinamide), the chemical structure of which is shown below, is a form of vitamin B3 that occurs in trace amounts mainly in meat, fish, nuts, and mushrooms, as well as to a lesser extent in some vegetables. It has been shown to have anti-inflammatory and sebum-regulating properties in topical applications, which can be helpful in the treatment of acne and can reduce redness and inflammation associated with rosacea. It can help to reduce the production of sebum, which can contribute to acne, and also reduce inflammation and redness. Niacinamide also reduces the appearance of hyperpigmentation, including age spots and melasma, by inhibiting the transfer of melanin from melanocytes to the surrounding skin cells. Niacinamide has been shown to improve the appearance of fine lines and wrinkles, and can also help to improve skin elasticity and texture by increasing the production of collagen and other proteins that are important for skin health. Niacinamide has also been shown to have photoprotective properties, which can help to reduce the risk of skin cancer by reducing DNA damage caused by UV radiation and by reducing the production of free radicals. Niacinamide also increases the biosynthesis of ceramides in the skin, strengthening the skin as a permeability barrier.

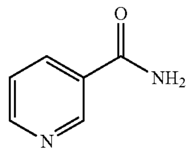

Sodium hyaluronate, the chemical structure of which is shown below, is the sodium salt of hyaluronic acid, a key component in connective, neural, and epithelial tissues as well as synovial fluid and extracellular matrix in the human body. It functions as a tissue lubricant by forming a viscoelastic solution in water, modulating the interactions of various tissues as they move against each other. It is therefore commonly used in dietary supplements to promote joint and skin health, often in combination with collagen. In gel form, sodium hyaluronate forms a cross-linked polymer that can be used to envelop and deliver other compounds for absorption, enabling topically-applied sodium hyaluronate to help facilitate the absorption of macromolecules such as HGH or somatropin, without the need for invasive delivery methods. This functions through the process of endocytosis, a cellular process in which cells take in materials by engulfing them with their cell membrane. When sodium hyaluronate is applied topically to the skin or mucous membranes, it can interact with the cells in these tissues, stimulating endocytosis and allowing for improved absorption and greater bioavailability of larger molecules.

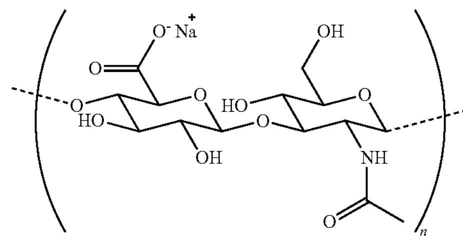

Squalane, the chemical structure of which is shown below, is a hydrogenated derivative of squalene, a naturally-occurring oil that is secreted by the skin particularly in regions of the forehead, nose, and ears. Squalane is commonly sourced from shark liver oil, as well as plant-based sources including olive oil, rice, and sugar cane. The complete hydrogenation of squalane improves its resistance to oxidative damage, making it more stable and thus more suitable for use in therapeutic products as it is not subject to auto-oxidation resulting in gradual loss of efficacy.

This also gives squalane a higher molecular weight and contributes to a less "greasy" feel when used in topical medications or cosmetics, and it is readily absorbed into the skin reducing the sensation of residue on the surface.

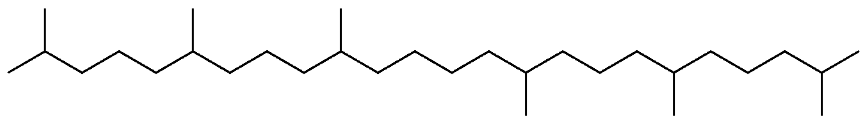 [SMILES: CC(C)CCCC(C)CCCC(C)CCCCC(C)CCCC(C)CCCC(C)C]

At a cellular level, squalane strengthens the lipid barrier layer of cells, promoting proper membrane function in the absorption and bioregulation of compounds and improving the intracellular production of ATP. It is also an intermediate compound in the production of sterol, the building block of a variety of biologically-important compounds including cholesterols and steroids. The chemical structure of sterol is shown below.

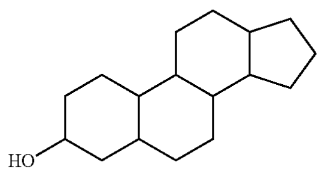 [SMILES: OC1CCC2C(CCC3C4CCCC4CCC23)C1]

Delivery of large biomolecules (such as HGH) or biosimilars (such as somatropin) has largely been limited to invasive routes (e.g., intramuscular and subcutaneous injection), because of their poor absorption and enzymatic degradation. However, administration via invasive routes presents several disadvantages-pain and risk of infection from syringes, unsuitability for administration to "needle-phobic" patients, and difficulty in providing effective self-administration. But delivering such medicaments transdermally is challenging because of the large size and complex electrochemistry of the molecules and the effectiveness of the skin barrier; in particular, the stratum corneum, which is the outermost part of the skin. Because of the stratum corneum, only low-molecular weight drugs with moderate lipophilicity are typically transferred administered transdermally via passive diffusion (for example, via patches or gels). Mechanical or other technological aids to skin barrier evasion, including iontophoresis or microneedles, provide some help, but these require medical professionals and are expensive and difficult to administer over time. A more advantageous approach would be to use penetration (or permeation) enhancers to help large biomolecules across the skin barrier without technological assistance. Even more preferable would be the use of natural phytochemicals to act as penetration enhancers to help large biomolecules cross the skin. Additionally, it is advantageous in some cases to administer a smaller precursor molecule that more easily crosses the skin barrier and then stimulates synthesis of the larger target biomolecules in vivo.

For example, L-DOPA is an amino acid that is synthesized in vivo in humans; it is a precursor to the crucial neurotransmitters dopamine, norepinephrine, and epinephrine. It has psychoactive properties and is used as a treatment in Parkinson's disease. L-DOPA has also been shown in numerous studies to promote the increase of serum HGH levels in humans. L-DOPA is a key phytochemical in velvet beans (*Mucuna pruriens*). The chemical formula of L-DOPA is:

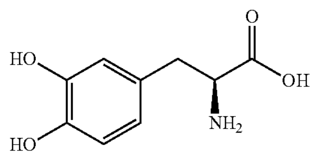

L-DOPA can be transdermally administered, preferably as a naturally-occurring phytochemical (such as via velvet bean extract), to supplement systemic HGH levels by providing increased precursor concentrations.

Another unconventional approach to transdermally administering large biomolecules is via the use of homeopathic principles. It has been shown that the use of a homeopathic preparation of somatropin—which does not require a prescription—can provide therapeutic benefits when delivered transdermally. If one assumes that homeopathic principles have validity, then the use of highly-diluted and activated formulations may provide a like benefit to that provided by injection of prescribed large doses of the same medicament. For example, over more than ten years a gel that includes a homeopathic formulation of somatropin at 30D dilution provides real benefits to its users, including an increase in serum HGH levels after application of the gel. It is likely that the fact that homeopathy does not rely on the actual presence of large amounts of the target biomolecule, but rather it relies on the presence of an energetically-activated aqueous solution of small phytochemicals. Moreover, a high degree of synergy is achieved by using natural photochemical penetration enhancers to improve the transdermal delivery rate of the energized homeopathic formulation. Thus the use of a variety of means to overcome the intrinsic difficulties of transdermal hormone supplementation provides the benefits of such supplementation without the risks of injecting prescription-based hormone treatments.

Another rapidly emerging area of natural health treatments is based on exploiting the rich phytochemical landscape made available by the opening up of legal *cannabis* products. *Cannabis* has been extensively cultivated throughout the world for centuries. Worldwide effects-targeted cultivation has progressed to the point where there are hundreds, if not thousands, of cultivars or strains which contain differing levels of the many active compounds that give *cannabis* its wide range of sought-after medical effects. One family of active compounds that are specific to *cannabis* is the cannabinoid family, of which more than 80 have been identified that may have overlapping but different medical effect profiles. These have been further separated into subclasses comprising: tetrahydrocannabinols (THC); cannabidiols (CBD); cannabichromenes (CBC); cannabinol (CBN); cannabigerols (CBG); cannabinodiol (CBDL); and other cannabinoids (cannabicyclol (CBL), cannabielsoin (CBE), cannabitriol (CBT) and other miscellaneous types.

In raw *cannabis*, the cannabinoids within the flowers' trichomes are carboxylated, meaning they have a COOH carboxylic acid group in their structure. These are mildly, if at all, psychoactive. In order for there to be psychoactivity the cannabinoids must be decarboxylated, or "decarbed" in layman's terms. Non-psychoactive THCA, for example, is decarboxylated to THC, a psychoactive cannabinoid. Both drying (or aging) and heat accomplish this chemical reaction, but the application of heat also results in the loss of certain other *cannabis* components such as the terpenes, which are highly volatile. Both the decarboxylated cannabinoids and the carboxylated cannabinoids exhibit important therapeutic effects for health, and although one can be chemically converted into the other, carboxylated cannabinoids becoming decarboxylated cannabinoids, As used herein both will be referred to as simply cannabinoids.

The biological effects of the cannabinoids may be mediated through two receptors specific for a class of endogenous cell signaling molecules, such as but not limited to N-arachidonoylethanolamine also known as AEA or anandamide, a neurotransmitter that predominantly binds to the cannabinoid receptor CB1 and a second compound, 2-arachidonoylglycerol also known as 2-AG which predominantly binds to the CB2 receptor. Expression of the CB1 receptor is found at highest levels in the central nervous system of humans and animals, particularly in the hippocampus, basal ganglia, neocortex, and spine (although expression in peripheral organs such as but not limited to the peripheral nervous system, liver, intestines, and kidneys is also present). Activation of the CB1 receptor has been linked to feelings of euphoria and an increase in appetite, among other effects. Expression of the CB2 receptor is found in the central and peripheral nervous system, the immune system and immune response-related cells, and peripheral organs, among other areas of expression. Activation of the CB2 receptor may have an analgesic effect, reduce inflammation, and increase of immune response towards certain pathogenic bacteria and fungi. The CB2 receptor may also mediate anti-cancer effects attributed to cannabinoids. Most recently, in relation to the CB2 receptor, it has been determined that different ligand agonists may specifically or predominantly activate specific receptor responses indicating a level of ligand functional selectivity for effects linked to the receptor.

Other cannabinoid receptors are found in almost every organ of the body including the skin, the digestive tract, and even in the reproductive organs. Cannabinoid receptors interact with cells in a lock (the cell receptor) and key (the cannabinoid) type of mechanism. The combination of the cell receptors and the cannabinoids comprise the endocannabinoid system, or ECS, which is an intricate network of cell receptor proteins that perform various functions in the body and is considered to be the greatest neurotransmitter system in the body. Bearing this in mind, it becomes important to realize and understand how *cannabis* can have an impact on numerous health issues including, but not limited to, Alzheimer's disease, memory loss, multiple sclerosis (MS) and other neurodegenerative diseases, and pain control and relief.

The major differences between the various cannabinoids are determined by the extent to which they are psychologically active (psychoactive). Three substantial classes of cannabinoids, including the cannabigerols (CBGs), cannabichromenes (CBCs), and cannabidiols (CBDs), are not known to have psychoactive effects. Δ-9-tetrahydrocannabinol (THC), cannabinol (CBN), and some other cannabinoids are known to be psychoactive to varying degrees. Non-psychoactive CBD is likely the most abundant cannabinoid, contributing up to 40% of *cannabis* resin in some strains (particularly those referred to as hemp strains); CBD has also been implicated in lessening the psychoactive effects of THC.

Of the over 80 known cannabinoid species, those most prevalent and most studied in *cannabis* cultivars are:

THC—Δ-9-tetrahydrocannabinol
CBD—cannabidiol
CBC—cannabichromene
CBN—cannabinol
CBG—cannabigerol
THCv—tetrahydrocannabivarin
CBDv—cannabidivarin
Δ-8-THC—Δ-8-tetrahydrocannabinol
THCA—Δ-9-tetrahydrocannabinolic acid
CBDA—cannabidiolic acid A number of these 80-plus cannabinoids display a plurality of important medical effects. The subset of the aforementioned cannabinoids for which these medically beneficial effects are characterized and confirmed are presented here with their chemical formulae and structures.

THC: As used herein, THC refers to Δ-9-tetrahydrocannabinol, the chemical formula for which is $C_{21}H_{30}O_2$ and the structure of which is:

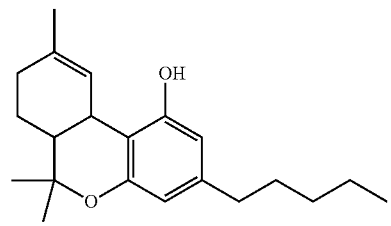 [SMILES: CCCCCc1cc(O)c2c(c1)OC(C)(C)C1CCC(C)=CC21]

THC is recognized as the primary psychoactive compound in *cannabis* and is the most common cannabinoid. Along with its psychoactive properties, THC may be medically used to alleviate several types of pain including the nerve-related pain of diabetic neuropathy and multiple sclerosis. Additionally, THC may be effective in alleviation of the symptoms of PTSD and reduction of nausea and vomiting, particularly that caused by chemotherapy. It has been shown to aid those with anorexia, as well as cancer and HIV associated wasting syndrome as it is an appetite stimulant. It improves breathing for asthmatics, acting as a potent bronchodilator, it relieves eye pressure in patients with glaucoma, improves insomnia, sleep apnea, and reduces nightmares. THC aids those with inflammatory bowel diseases such as Crohn's disease, ulcerative colitis and leaky gut, as well as other intestinal diseases by decreasing intestinal permeability and strengthening intestinal tight junctions. THC slows and prevents Alzheimer's disease and helps control seizures. THC reduces pain and tremors and improves sleep for those with Parkinson's disease. THC, CBD, CBG, and CBC together work synergistically as a powerful cancer tumor-fighting combination. This combination is more powerful than any single one of these working alone.

CBD: As used herein, CBD stands for cannabidiol, the chemical formula for which is $C_{21}H_{30}O_2$ and the structure of which is:

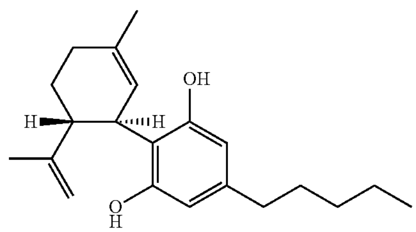 [SMILES: C=C(C)[C@@H]1CCC(C)=C[C@H]1c1c(O)cc(CCCCC)cc1O]

CBD, or cannabidiol, is a non-psychoactive member of the cannabinoids and is one of the most prevalent chemical compounds in the *cannabis* plant. Found predominantly in the resin glands of the female plant, this compound can stop muscle spasms and epileptic seizures, and can reduce idiopathic anxiety, a prevalent and significantly debilitating aspect of mental illness. It is used to treat nicotine addiction, osteoporosis, diabetes, cancer, obsessive-compulsive disorder, Lupus, Parkinson's disease, and motor disorders, and soothes neuropathic and chronic pain. It has anti-inflammatory, antioxidant, neuroprotectant, anxiolytic, antidepressant, analgesic, anti-tumor, and anti-psychotic effects. CBD is powerful all by itself, but it is even more powerful when combined with other cannabinoids such as THC.

CBC: As used herein, CBC stands for cannabichromene, the chemical formula for which is $C_{21}H_{30}O_2$ and the structure of which is:

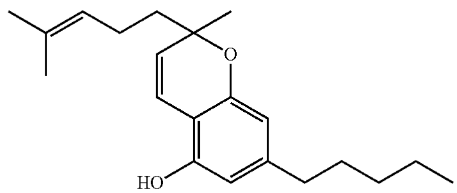 [SMILES: CCCCCc1cc(O)c2c(c1)OC(C)(CCC=C(C)C)C=C2]

Cannabichromene, or CBC, is the third most prevalent cannabinoid in the marijuana plant in general. In some strains CBC is more prevalent than CBD, and like CBD it is non-psychoactive.

CBC is anti-inflammatory and even more so when combined with THC. It has anti-tumor effects and shows promise in fighting breast cancer. When combined with CBD, THC, and CBG, the cancer fighting effects are intensified. It may be useful as an antidepressant and may be more powerful than the other cannabinoids in this capacity. CBC shows antiviral and mild antifungal activity. While CBC addresses several other health issues, including inflammation, cancer, depression, and fungal infections, it also increases the number of brain cells and therefore is useful in the treatment of several brain related disorders. CBC promotes neurogenesis in individuals at any age. This not only affects memory and learning, but can off-set certain dementias which occur when the brain stops growing new cells. It is likely that CBC can alleviate to some extent certain forms of depression and neuro-degenerative diseases via this particular mechanism of neurogenesis.

CBN: As used herein, CBN stands for cannabinol, the chemical formula for which is $C_{21}H_{26}O_2$ and the structure of which is:

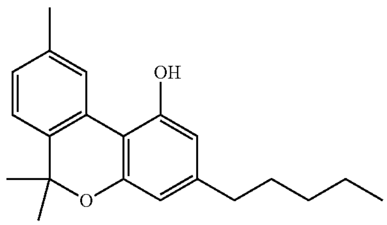 [SMILES: CCCCCc1cc(O)c2c(c1)OC(C)(C)c1ccc(C)cc1-2]

Cannabinol, or CBN, emerges when the dried *cannabis* flower becomes stale; over time, THC and CBD, which are generated by enzymatically-driven synthesis from CBG, break down through oxidative degeneration into CBN. CBN has antibiotic properties, including against methicillin-resistant *Staphylococcus aureus* (MRSA), and also has pain-relieving properties through the release of endorphins. It may delay the onset of, and relieve symptoms of, degenerative motor neural diseases such as amyotrophic lateral sclerosis (ALS) and MS. It works as an appetite stimulant and is more powerful than CBD and CBG in this regard. It has been found to have potent sedative characteristics, making it possibly the most potent single sedative of all the cannabinoids. When combined with THC, CBN has also been found to be effective at lowering the ocular pressure which produces blindness in glaucoma patients. CBN also promises to be useful in future for lowering blood pressure overall.

CBG: As used herein, CBG stands for cannabigerol, the chemical formula for which is $C_{21}H_{32}O_2$ and the structure of which is:

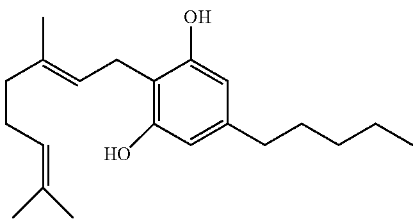 [SMILES: CCCCCc1cc(O)c(C/C=C(\C)CCC=C(C)C)c(O)c1]

CBG, or cannabigerol, is found in *cannabis* early in the growth cycle, making it somewhat difficult to find in large quantities (CBG is synthesized from smaller constituents, and serves as the feedstock for enzymatic synthesis of THC, CBD, and other cannabinoids, and so CBG is regarded as the source of all cannabinoids. It is non-psychoactive and can also be cultivated in hemp, in which it occurs in greater quantities. CBG has antibiotic properties stronger than CBN and comparable to CBD and is effective against various types of bacteria and fungi. It has therapeutic potential for skin conditions like psoriasis and eczema. CBG is reportedly a more potent pain reliever than THC, and functions as an antidepressant and mood-stabilizer by preventing the uptake of GABA and by increasing serotonin levels in the brain.

THCV: As used herein, THCV stands for tetrahydrocannabivarin, the chemical formula for which is $C_{19}H_{26}O_2$ and the structure of which is:

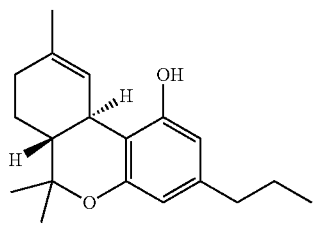 [SMILES: CCCc1cc(O)c2c(c1)OC(C)(C)[C@@H]1CCC(C)=C[C@@H]21]

THCV, or tetrahydrocannabivarin, is one of the several cannabinoids that works in synergy with THC, and mitigates some of the negative psychoactive impacts of THC. THCV's medical uses are antiepileptic, anticonvulsant, and anti-seizure; it is neuroprotective and mitigates some of the short-term memory and speech impairment that comes from THC; it promotes weight loss by suppressing the appetite and possibly decreasing body fat and boosting energy metabolism.

CBDV: As used herein, CBDV stands for cannabidivarin, the chemical formula for which is $C_{19}H_{26}O_2$ and the structure of which is:

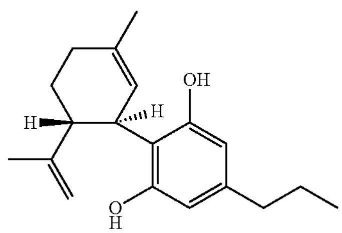 [SMILES: C=C(C)[C@@H]1CCC(C)=C[C@H]1c1c(O)cc(CCC)cc1O]

Cannabidivarin, or CBDV, is a slightly-degraded close relative of CBD. It is used as an anticonvulsant, an antiepileptic, and has antiemetic properties (as well as aiding those with gastrointestinal issues).

Δ-8-THC: As used herein, Δ-8-THC stands for Δ-8-tetrahydrocannabinol, the chemical formula for which is $C_{21}H_{30}O_2$ and the structure of which is:

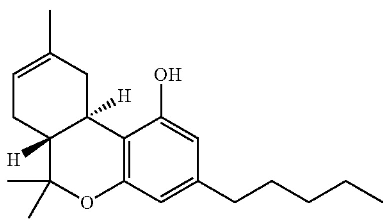 [SMILES: CCCCCc1cc(O)c2c(c1)OC(C)(C)[C@@H]1CC=C(C)C[C@@H]21]

Δ-8-tetrahydrocannabinol is different from Δ-9-tetrahydrocannabinol in that it is less psychoactive. It has both neuroprotective and anti-anxiety properties, as well as being anti-emetic, and may be a stronger appetite stimulant than Δ-9-THC, making it an important consideration for people undergoing chemotherapy.

THCA: As used herein, THCA stands for Δ-9-tetrahydrocannabinolic acid, the chemical formula for which is $C_{22}H_{30}O_4$ and the structure of which is:

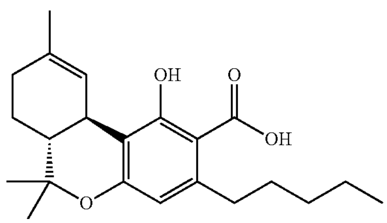 [SMILES: CCCCCc1cc2c(c(O)c1C(=O)O)[C@@H]1C=C(C)CC[C@H]1C(C)(C)O2]

Δ-9-tetrahydrocannabinolic acid, or THCA, is a non-psychoactive compound found in *cannabis* prior to decarboxylation to the psychoactive version, THC, by application of heat or drying or both. THCA levels are particularly high in the live or freshly harvested plant, but as the plant dries, THCA slowly converts to THC, a process expedited by smoking or vaping. Because THCA readily converts to the psychoactive THC upon heat application such as smoking or vaping, it cannot be inhaled or absorbed into the body by these particular means. THCA shows anti-inflammatory properties and may thus be used in treatment of arthritis and lupus. Its neuroprotective properties may make THCA a candidate for treatment of neurodegenerative diseases; its anti-emetic properties making it a possible treatment for nausea and appetite loss, and its anti-proliferative properties making it a candidate in treatment in certain cancers such as but not limited to prostate cancer.

CBDA: As used herein, CBDA stands for cannabidiolic acid, the chemical formula for which is $C_{22}H_{30}O_4$ and the structure of which is:

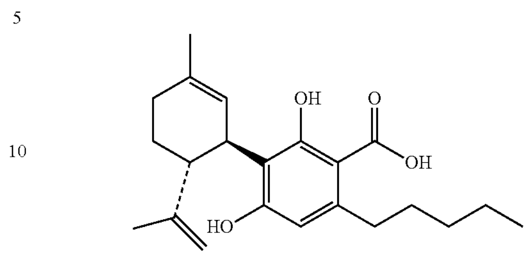

Cannabidiolic acid, or CBDA, cannot administered by smoking or vaporizing because doing so decarboxylates it to CBD, similar to THCA conversion to THC. The therapeutic uses for CBDA include antibacterial, anti-emetic, anti-inflammatory, and cancer cell anti-proliferative.

Another family of active compounds present in, but not exclusive to, *cannabis* are the terpenes and decarboxylated terpenes, which are known as terpenoids. Decarboxylation occurs with the removal of the COOH functional group, and can be seen in drawings of the structures. These two terms are commonly used interchangeably, and although they are not chemically identical in structure or chemical formula as terpenoids are decarboxylated versions of some terpenes and exist in plants in this decarboxylated form, for the purposes of this invention both will be referred to as simply terpenes. Though *cannabis* contains up to 200 different terpenes and terpenoids, there are approximately 10 primary terpenes and 20 secondary terpenes that occur naturally in significant concentrations in the *cannabis* plant.

Terpenes are vital components of *cannabis*, and are important medicinally active compounds that are found in up to 1.5% of the total extraction. They are a large and diverse class of organic compounds, produced by a wide variety of plants giving them their flavor, aroma, and color. Terpenes are the building blocks of a plant's essential oils, and essential oils contain mixtures of the various terpenes found in the plants from which they were extracted.

The isoprene skeleton ($C_5H_8$) may be found in naturally occurring terpenes (also known as isoprenoids), but these terpene compounds do not arise from isoprene itself. Terpenes may be thought of as multiples of isoprene subunits, which is the cornerstone of the "isoprene rule" for terpenes.

The ten primary terpenes and twenty secondary terpenes that occur in significant concentrations are as follows:

The primary terpenes are: myrcene, α-pinene, ocimene, terpineol, β-caryophyllene, linalool, limonene, terpinolene, valencene, and geraniol.

The secondary terpenes are: phellandrene, carene, terpinene, fenchol, borneol, bisabolol, phytol, camphene, sabinene, camphor, isoborneol, menthol, cedrene, nerolidol, guaiol, isopulegol, geranyl acetate, cymene, eucalyptol, and pulegone.

These terpenes have non-psychoactive therapeutic effects and may be safely used to treat a variety of health conditions. They may also be combined with each other and with cannabinoids, yielding a whole new range of health effects. Some combinations of terpenes act in synergy with boosting effects, while others act as antagonists with effects that inhibit. Some terpenes increase the assimilation of THC, while others may affect the flow of dopamine and serotonin, two of the main regulators of mood and behavior.

Cannabinoid-terpenoid interactions have the potential to produce synergy with respect to the treatment of pain, inflammation, depression, anxiety, addiction, mood and behavior, epilepsy, cancer, fungal infections and bacterial infections, including MRSA.

The primary and secondary terpenes with some of their medical actions are as follows:

Primary Terpenes:

Myrcene—Myrcene, specifically β-myrcene, is a monoterpene and the most common terpene produced by *cannabis* (some varieties contain up to 60% β-myrcene as a fraction of the total terpene content). A-myrcene is not found in nature and was first synthesized in 1965. The chemical formula for β-myrcene is $C_{10}H_{16}$ and the structure is:

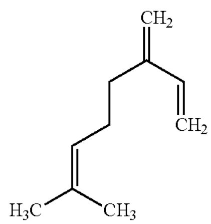

Myrcene is found in most varieties of *cannabis* as well as menthol, lemon grass, and hemp, and is widely used in the perfume industry. Its aroma has been described as musky, earthy, and herbal.

Myrcene has some very special medicinal properties, including lowering the resistance across the blood-brain barrier allowing itself and many other chemicals to cross the barrier more easily and quickly. Myrcene also increases cell membrane permeability, and in the case of cannabinoids like THC, β-myrcene allows the cannabinoid to take effect more quickly. More uniquely still, β-myrcene has been shown to increase the maximum saturation level of the CB1 receptor, allowing for a greater maximum psychoactive effect. Myrcene has anti-microbial and anti-septic properties, and acts as a natural anti-depressant, anti-carcinogen and anti-inflammatory agent. It is a potent analgesic and is anti-mutagenic. It blocks the action of cytochrome, aflatoxin B and other pro-mutagenic carcinogens. It acts as an inhibitor of gastric and duodenal ulcers. Its sedative and relaxing effects make it ideal for the treatment of insomnia and pain.

α-Pinene—Alpha-pinene is a monoterpene alkene isolated from pine needle oil as well as from *cannabis*. There are two structural isomers of pinene found in nature: α-pinene and β-pinene, with α-pinene being the most widely encountered terpenoid in nature. With an aroma and flavor of pine, this is partially where pine trees get their scent. The chemical formula is $C_{10}H_{16}$ and the structure is:

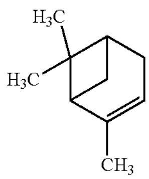

Pinene is one of the principal monoterpenes that is important physiologically in both plants and animals. It tends to react with other chemicals, forming a variety of other terpenes (like limonene), as well as other compounds.

Medicinally, α-pinene has an anti-tumor effect and has shown anti-cancer activity. Alpha-pinene is used as an anti-inflammatory, expectorant, bronchodilator, memory enhancer, as a local antiseptic, and it may decrease oil production in oily skin. It acts as a broad spectrum antibiotic and is highly effective against MRSA when combined with the cannabinoids CBD and CBN, all three working in synergy with each other. Alpha-pinene increases alertness and counteracts some of the negative effects of the cannabinoids THC, such as anxiety. It is also believed that the negative memory effects of THC may be lessened if mixed with α-pinene.

Ocimene—Ocimene is a group of isomeric monoterpenes found in a wide variety of fruits, spices, and plants. Alpha-ocimene and the two β-ocimenes, cis-β-ocimene and trans-β-ocimene, differ in the position of the isolated double bond: in the alpha isomer it is terminal. β-ocimene exists in two stereoisomeric forms, cis and trans, with respect to the central double bond. Ocimene is often found naturally as a mixture of its various forms. The chemical formula is $C_{10}H_{16}$ and the three structures are:

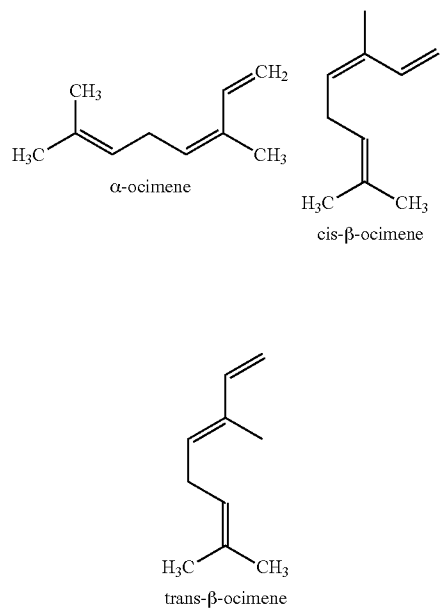

α-ocimene cis-β-ocimene trans-β-ocimene

Ocimene is recognized by its sweet, fragrant, herbaceous, and woodsy aromas, which feature prominently in several perfumes as well as flavorings, and which help plants defend themselves in their natural environment. Ocimene occurs naturally in botanicals as diverse as *cannabis*, mint, parsley, pepper, basil, mangoes, orchids, kumquats, and allspice.

Ocimene's potential medical benefits include antiviral, antifungal, antiseptic, decongestant, and antibacterial benefits.

Terpineol—Found in *cannabis* as well as in over 150 other plants, terpineol exists as four isomers: α-terpineol, β-terpineol, γ-terpineol and terpinen-4-ol, are four closely related monoterpene alcohols. These are found mixed in plants and their essential oils, with α-terpineol comprising the majority of the mixture. The chemical formula is $C_{10}H_{18}O$ and the four structures are:

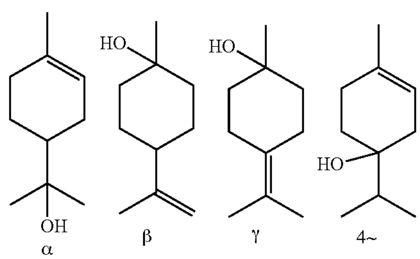

Terpineol has a floral aroma, resembling lilacs, clove, citrus, or apple blossoms, and other than *cannabis* it also occurs naturally in lilacs, pine trees, lime blossoms, and *eucalyptus*, as well as contributing to the distinctive, pine smoke-based aroma of lapsang souchong tea. From a flavor perspective, terpineol tastes like mint and anise. Terpineol is most frequently found in *cannabis* strains which also contain high levels of α-pinene. Due to α-pinene's strong aroma, terpineol may be difficult to detect by odor when the two occur simultaneously as the scent of α-pinene masks the more delicate floral scent of terpineol.

Terpineol, specifically α-terpineol, is known to have calming, relaxing effects and is a mild sedative. Terpineol inhibits skin acne, acts as an antibiotic, anti-inflammatory, antioxidant and has anti-malaria properties. Terpineol's most important property is its anti-cancer property it is able to kill tumors directly.

β-Caryophyllene—β-caryophyllene is a bicyclic sesquiterpene with the formula $C_{15}H_{24}$ and the structure:

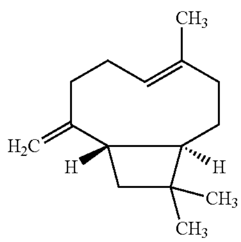

β-Caryophyllene (BCP) is a natural bicyclic sesquiterpene abundantly found in essential oils from various spices, fruits and medicinal as well as ornamental plants; β-caryophyllene is found in many plants such as various *cannabis* strains, copaiba, Thai basil, cloves, cinnamon leaves and black pepper, oregano, and other edible herbs; in minor quantities, it may be found in lavender as well as in many green, leafy vegetables. Its aroma has been described as peppery, woody spicy, and hoppy, as in hops used for brewing beer, to which *cannabis* is closely related. β-caryophyllene is the major terpene and active component of copaiba oil, which is known to exhibit strong antioxidant and anti-inflammatory action. In a study of the action of β-caryophyllene, the major constituent of copaiba oil, on the systemic inflammation, oxidative status, and liver cell metabolism associated with rheumatoid arthritis, it was found that β-caryophyllene reduced swelling of joints and lymph nodes as well as the number of circulating and articular leukocytes. Moreover, β-caryophyllene eliminated increases of protein carbonyl groups and myeloperoxidase activity in the liver and plasma of arthritic subjects and increased levels of reactive oxygen species and reduced glutathione in the arthritic liver. These beneficial actions were of the same type and strength as those of copaiba oil (*Copaifera reticulata*) and, therefore, β-caryophyllene is likely responsible for the anti-inflammatory and antioxidant actions of the oil.

β-caryophyllene is the only terpene known to interact with the endocannabinoid system, and does so at the CB2 receptor, which does not produce a high (that is, the CB-2 receptor is not implicated in *cannabis* psychoactivity). β-caryophyllene selectively binds to the CB2 receptor where it is a functional CB2 agonist, giving it an anxiolytic and anti-depressant effect and showing that β-caryophyllene may be useful in treating anxiety and depression. β-caryophyllene also has anti-oxidant, anti-inflammatory, anti-cancerous, and local anesthetic effects. Further, β-caryophyllene is unique for being both a terpene and a dietary cannabinoid, a food component which acts as a cannabinoid and binds to CB2 receptors.

Other phytocannabinoids in combination, especially cannabidiol (CBD) and β-caryophyllene, when delivered orally, appear to be promising candidates for the treatment of chronic pain due to their high safety and low adverse effects profiles. That is, the CB2 agonism of β-caryophyllene improves the therapeutic effectiveness of CBD synergistically. Therefore β-caryophyllene, through its CB2 receptor-dependent pathway, may be an excellent therapeutic agent to prevent nephrotoxicity (poisonous effect on the kidneys) caused by anti-cancer chemotherapy drugs such as cisplatin, in addition to its excellent anti-inflammatory and antioxidant effects.

β-caryophyllene also has antinociceptive properties, blocking sensory neuron detection of pain stimuli. This further suggests that copaiba oil or β-caryophyllene is useful in treating a number of medical issues such as arthritis and neuropathy pain. It is anti-inflammatory because of its ability to bind directly to the endocannabinoid receptor known as CB2. It is also protective of the cells lining the digestive tract, which offers promise for treating some ulcers, and is anti-fungal. β-caryophyllene holds promise for cancer treatment.

Combining β-caryophyllene with other ingredients, such as those mentioned above, may provide potential synergistic effects and enhance their benefits. For example, combining β-caryophyllene with curcumin may enhance the anti-inflammatory and antioxidant properties of both compounds, potentially improving conditions such as arthritis, digestive disorders, and certain types of cancer. Similarly, combining β-caryophyllene with CBD may also provide synergistic benefits. CBD is known for its anti-inflammatory and anxiolytic effects, and β-caryophyllene has been shown to activate the same receptors in the body as CBD, potentially enhancing these effects. This combination may also have potential as a treatment for chronic pain and certain mental health disorders. Finally, combining β-caryophyllene with capsaicin, the active compound in chili peppers, may provide potential benefits for weight loss and metabolic health. Both compounds have been shown to increase thermogenesis, or the process by which the body generates heat and burns calories, potentially leading to increased fat loss and improved metabolic health. Combining β-caryophyllene with 5-MTHF may enhance their individual benefits for mental health and cognitive function. β-caryophyllene has been shown to have anti-inflammatory and anxiolytic effects, while 5-MTHF is involved in the production of neurotransmitters such as serotonin, which is important for regulating mood and cognitive function. By combining these two compounds, it is possible that their effects on mental health and cognitive function could be enhanced, potentially improving conditions such as depression and anxiety. Combining β-caryophyllene with caprylic acid may have potential benefits for gut health and immune function. β-caryophyllene has been shown to have anti-inflammatory and immunomodulatory effects, while caprylic acid has been shown to have antimicrobial properties and may help promote the growth of beneficial gut bacteria. By combining these two compounds, it is possible that their effects on gut health and immune function could be enhanced, potentially improving conditions such as gut dysbiosis and autoimmune disorders. Combining β-caryophyllene with cetylated fatty acids may provide potential benefits for joint health and inflammation. β-caryophyllene has been shown to have anti-inflammatory and analgesic effects, while cetylated fatty acids have been shown to reduce inflammation and improve joint mobility. By combining these two compounds, it is possible that their effects on joint health and inflammation could be enhanced, potentially improving conditions such as arthritis and other inflammatory joint disorders Copaiba oil is an oleoresin extracted from the trunk of the *Copaifera* tree and is widely used in popular medicine in that region for different purposes, such as anti-inflammatory, antitumoral and antimicrobial. Oil extracted from copaiba acts similarly as anti-inflammatory compounds (inhibiting histaminergic and serotoninergic pathways) and presents antinociceptive effect (possibly mediated by opioid receptors). Furthermore β-caryophyllene is a selective agonist to the peripheral cannabinoid receptor CB2, which is related to the treatment of pain and inflammation.

Linalool—Linalool is a terpene alcohol that occurs as two enantiomers d-linalool and 1-linalool, with the chemical formula $C_{10}H_{18}O$ and the structures:

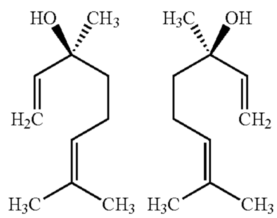

Linalool has a floral lavender aroma with a hint of spice. In addition to *cannabis*, linalool may be found in an array of flowers and spice plants such as lavender, bay laurel, sweet basil, mint, cinnamon, citrus and even some fungi. Linalool is a critical precursor in the formation of vitamin E.

Linalool may be used as an anti-inflammatory or as an immune booster, and may significantly reduce lung inflammation caused by cigarette smoke as well as reducing lung irritation potentially caused by inhaling *cannabis* smoke. Linalool helps to restore cognitive and emotional function partially via its anti-inflammatory effect, and may therefore be used to treat various forms of dementia, and particularly Alzheimer's disease. It helps with insomnia, and because it also lessens the anxiety brought on by pure THC, it helps in the treatment of anxiety and psychosis. Linalool has anesthetic effects and is calming, relaxing and mood lifting, and helps reduce headaches and migraines. Linalool may be useful to help treat liver cancer, and also helps to modulate motor movements, giving it anti-epileptic properties. It is an effective insecticide against fruit flies, fleas, and cockroaches, making it useful as an insect repellent and for use in and around the home and garden.

Limonene—Limonene is a monocyclic monoterpene and one of two major compounds formed from pinene. It exists as two enantiomers, d-limonene and l-limonene, and has the chemical formula $C_{10}H_{16}$. The structures are:

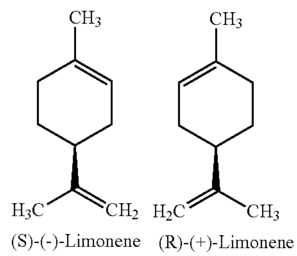

(S)-(-)-Limonene (R)-(+)-Limonene

Limonene has a citrusy aroma and the more common d-isomer smells like oranges. While it is found in *cannabis*, it is also present in citrus fruit and especially lemons, juniper, and peppermint. It assists in the absorption of other terpenes through the skin and other body tissues. Limonene has anti-fungal, anti-bacterial, and anti-depressant effects; it promotes a general uplift in mood and attitude, and it helps promote weight-loss. It is a strong antioxidant and exerts anti-carcinogen properties as it may reduce the formation of some tumor growths and alleviate fat buildup in the liver induced by diet. Limonene is known to increase blood pressure which is useful for those with low blood pressure. It has very low toxicity and adverse effects are rarely associated with it.

Terpinolene-Terpinolene, also called δ-terpinene (δ-terpinene), is one of a class of isomeric monoterpenes, all of which have the chemical formula $C_{10}H_{16}$, and which differ from each other only in the position of the carbon-carbon double bonds. The α-terpinene, γ-terpinene, δ-terpinene (terpinolene) are all found in plant essential oils, whereas β-terpinene is synthetically prepared from sabinene. The chemical structures are:

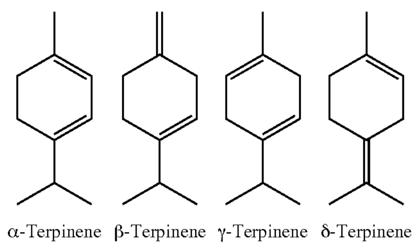

α-Terpinene β-Terpinene γ-Terpinene δ-Terpinene

Terpinolene is characterized by a fresh, piney, floral, herbal, sometimes smoky or woody, and occasionally citrusy aroma and flavor. It is found in a variety of fragrant plants including *cannabis*, nutmeg, tea tree, conifers, citrus, apples, cumin, marjoram, sage, rosemary, Monterey cypress, and lilacs. It is used in soaps, perfumes, cosmetics, flavorings, and in the semiconductor industries.

Terpinolene is a central nervous system depressant used to induce drowsiness or sleep or to reduce psychological excitement. It has a sedative effect when inhaled, making it useful for insomnia and anxiety.

Terpinolene markedly reduces the expression of the AKT1 gene, which produces the protein AKT1 kinase, an enzyme that plays a vital role in various important signaling pathways and cellular processes. AKT1 kinase helps regulate cell growth and division (proliferation), differentiation, cell survival, and apoptosis (cell death) when cells become damaged or are no longer needed. The AKT1 gene belongs to the class of genes known as oncogenes. When mutated, oncogenes have the potential to cause normal cells to become cancerous. The activation of AKT is connected with many types of cancers as it increases cell proliferation and suppresses apoptosis. By suppressing the AKT1 gene expression, both rampant cell proliferation and lack of apoptosis are suppressed, making terpinolene a valuable anti-cancer agent.

Terpinolene, together with vitamins A and E, prevents the oxidation of "bad cholesterol" (low-density lipoprotein, or LDL) and is therefore helpful in the treatment of heart disease.

Terpinolene's potential medical benefits include: antioxidant, sedative, antibacterial, antifungal, insect repellent, anti-proliferative (anti-cancer) and non-genotoxic, making it very safe and very healing.

Valencene—Valencene is a bicyclic sesquiterpene with chemical formula $C_{15}H_{24}$ and is found in Valencia oranges as well as *cannabis*. The chemical structure is:

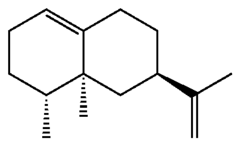

It has a sweet, fresh, citrusy, woody, aroma and flavor and is used in both the flavor and perfume industries.

Valencene is toxic to ticks and mosquitoes at lesser concentrations than DEET and doesn't have the toxicity of DEET. Valencene is an effective insect repellent for ticks, mosquitos, and other insects. It is also anti-inflammatory, and may lower the levels of inflammatory markers in macrophages.

Geraniol—Geraniol is an acyclic monoterpene alcohol whose formula is $C_{10}H_{18}O$ and which boils at about 447° F. and frequently occurs in strains that also produce linalool. Not only from *cannabis*, geraniol is also found in rose, geranium, lime, lemon, lemongrass, nutmeg, bergamot, carrot, coriander, lavender, blueberry, blackberry, and tobacco. Geraniol emits a rose-like scent that makes it a popular perfume additive. The chemical formula is:

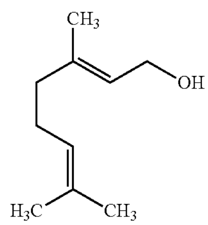

Geraniol is an effective mosquito repellent, an antioxidant, and shows a potential protective effect against neuropathy. It is anti-cancer and inhibits the growth and biosynthesis of colon cancer cells, and when combined with farnesol and perill alcohol, suppress pancreatic tumor growth making it especially useful for cancer of the pancreas which currently is extremely difficult to cure.

Secondary Terpenes:

Phellandrene—Phellandrene refers to a pair of cyclic monoterpenes that have a similar molecular structure and similar chemical properties, α-phellandrene and β-phellandrene, which are double-bond isomers of each other. In α-phellandrene, both double bonds are endocyclic (within the ring structure) and in β-phellandrene, one of them is exocyclic (external to the ring structure). Phellandrene has the chemical formula $C_{10}H_{16}$ and is described as pleasant, fresh, citrusy, minty and peppery-woody. The chemical structures are:

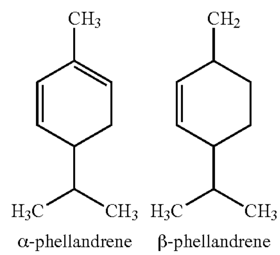

α-phellandrene β-phellandrene

Phellandrenes are used in the perfume and the flavoring industries because of their pleasing aromas and because they are absorbed through the skin. α-phellandrene may form dangerous, explosive peroxides on contact with air at elevated temperatures. β-phellandrene is non-hazardous, and both phellandrenes may be found in *cannabis* as well as in spices such as allspice, cinnamon, garlic, dill, pepper, parsley, and in the essential oils of *angelica, eucalyptus, lavandula*, mentha, fennel, ginger, and *Pinus* species.

Insoluble in water but miscible with ether, phellandrene is one of the easiest terpenes to identify in the lab. When a solution of phellandrene in a solvent (or an oil containing phellandrene) is treated with a concentrated solution of sodium nitrate and then with a few drops of glacial acetic acid, very large crystals of phellandrene nitrate speedily form.

Phellandrene has special medicinal values and has been used in traditional Chinese medicine to treat digestive disorders. It is one of the main compounds in turmeric leaf oil, which is used to prevent and treat systemic fungal infections. Phellandrene possesses antidepressant properties and is also used as an insecticide.

Carene—Δ-3-Carene is a bicyclic monoterpene with a sweet, pungent odor. It is found naturally in *cannabis* and in many healthy, beneficial essential oils, including cypress oil, juniper berry oil and fir needle essential oils, and is a main constituent of pine and cedar resin. It is also present in bell pepper, basil oil, grapefruit and orange juices, citrus peel oils from fruits like lemons, limes, mandarins, tangerines, oranges, kumquats, and it is a major component of turpentine, comprising as high as 42% depending on the source. The chemical formula is $C_{10}H_{16}$ and the chemical structure is:

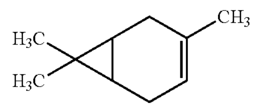

Δ-3-Carene is used as a flavoring in many products.

It is nontoxic but may cause irritation when inhaled. It is possible that high concentrations of δ-3-carene in some strains may be partly responsible for symptoms of coughing, itchy throat, and eye afflictions when smoking *cannabis*.

Δ-3-carene is an effective anti-inflammatory. In higher than natural concentrations, δ-3-carene may be a central nervous system depressant and a skin irritant. It is often used to dry out excess body fluids, such as tears, runny noses, sweat, and menstrual flows.

Terpinene—Terpinenes are a group of isomeric terpenes with the chemical formula $C_{10}H_{16}$ and this group is composed of three natural isomeric terpenes and one synthetic one that differ from each other in the positions of the carbon to carbon double bond. A-terpinene, δ-terpinene (terpinolene), and γ-terpinene are naturally occurring, whereas β-terpinene is not found in nature but may be synthetically produced from sabinene. A-terpinene is also called terpinolene. The chemical structures are:

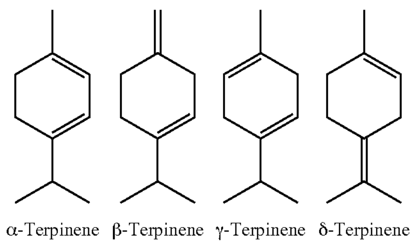

α-Terpinene β-Terpinene γ-Terpinene δ-Terpinene

Terpinene is a major component of essential oils made from citrus fruits, and has a lemon odor. A-terpinene is widely used in the flavor, perfume, cosmetics, soap, pharmaceutical industries, as well as in food and confectionary.

Terpinene is considered to be a well-tolerated additive in the pharmaceutical industry, and it has very strong antioxidant properties.

Fenchol—Fenchol, also called 1,3,3-trimethyl-2-norbornanol, is a terpene and an isomer of borneol with the chemical formula $C_{10}H_{18}O$ and the chemical formula is:

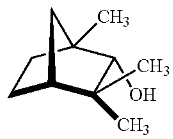

This particular terpene is an enantiomer, d-fenchol or (1R)-endo-(+)-fenchol, but it has no mirror image found in nature, thus it is enantiopure.

Found in *cannabis*, it also occurs naturally in basil, fennel, nutmeg, pine, rosemary oil, lime oil, beer and more. It has a bitter, lime flavor and is used extensively in perfumes, flavorings, soaps, detergents, and personal care products. It is known to exhibit antibacterial properties.

Borneol—Borneol, a terpene alcohol, has the chemical formula $C_{10}H_{18}O$ and exists naturally as two enantiomers, 1-borneol and d-borneol, both of which are found in nature. It is easily oxidized to camphor, has an aroma of camphor, mint, and earth, and is a component of many natural essential oils. It is found in *cannabis* resin and herbs like thyme, rosemary, and cinnamon. The chemical structure is:

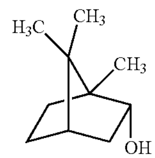

Borneol is used in the perfume industry, as well as in dietary and herbal supplements in the USA.

Borneol is used as a calming sedative, it is used to fight fatigue, stress, to relax, and to recover from illness. Borneol is used as an anti-inflammatory, an anti-nociceptive/analgesic, a skin tonic, a local anesthetic, as an anti-insomnia, anti-septic, a digestive aid, a sedative and an antispasmodic. It is used to improve circulation, to reduce pain and swelling, as a bronchodilator, a cough suppressant, and an insect repellant.

Bisabolol—Also called levomenol, α-bisabolol is a natural monocyclic unsaturated sesquiterpene alcohol with the chemical formula $C_{15}H_{26}O$ and a chemical structure of:

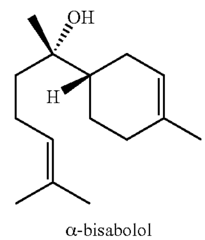 [SMILES: CC(C)=CCC[C@](C)(O)[C@@H]1CC=C(C)CC1]

α-bisabolol

A-bisabolol is found in *cannabis*, the Brazilian shrub candeia, and German chamomile. It has a floral aroma.

A-bisabolol, which is nontoxic and nonirritating to the skin, possesses anti-inflammatory and wound healing properties, as well as antimycotic and antibacterial effects, and may be used as a deodorizer. It is a potent inhibitor of fungi, *Candida albicans*, and gram-positive bacteria. It shows promise in the treatment of certain cancers as it induces apoptosis in leukemia.

Phytol—Phytol is a natural linear diterpene alcohol with the chemical formula $C_{20}H_{40}O$ that may be used as a precursor to prepare synthetic forms of vitamin E and vitamin K1. Found in *cannabis* and green tea, phytol results from the degradation of chlorophyll and is an oily liquid that is nearly insoluble in water, but soluble in most organic solvents. The chemical structure is:

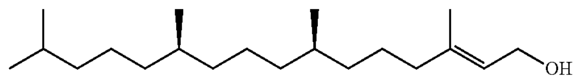 [SMILES: C/C(=C\CO)CCC[C@H](C)CCC[C@H](C)CCCC(C)C]

Phytol inhibits the enzyme that degrades the neurotransmitter GABA (γ-aminobutyric acid), which may partially account for its relaxing effect. In the body, phytol is essential in activating enzymes that have a positive effect on the production of insulin. It is beneficial in regulating blood glucose, for reducing blood pressure and for reducing cholesterol levels in blood.

Camphene—Camphene is a bicyclic monoterpene with the chemical formula $C_{10}H_{16}$ and the chemical structure:

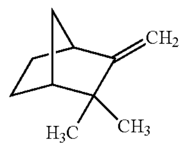

Camphene readily volatilizes at room temperature and has a pungent odor similar to camphor. It is a minor component of many essential oils such as turpentine, cypress, neroli, valerian camphor, citronella and ginger. It is used as a flavoring for food, and in the perfume industry. It is produced industrially by catalytic isomerization of the more common α-pinene.

Camphene is found in essential oils extracted from *cannabis* and certain trees, and it may play a critical role in cardiovascular health. Camphene possesses antioxidant, anti-inflammatory, and antibiotic characteristics, and shows promise for pain relief.

Camphene may reduce plasma cholesterol and triglycerides. Given the importance this plays in heart disease, camphene might be used as an alternative to pharmaceutical drugs which cause intestinal problems, liver damage, and muscle inflammation.

Sabinene—Sabinene is a bicyclic monoterpene with the chemical formula $C_{10}H_{16}$, and exists as d and l enantiomers. The chemical structures are:

d-Sabinene

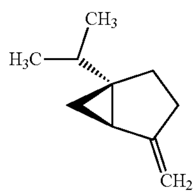

l-Sabinene

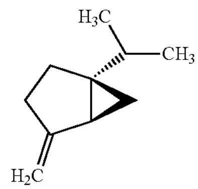

It has an aroma of spice, pine, and orange, and is found in many plants including *cannabis*, Norway spruce, black pepper, basil, and *Myristica fragrans*—the world's main source of nutmeg. It is used in the perfume industry and in the food industry as a flavoring.

Sabinene has antioxidant and anti-inflammatory properties, and benefits liver function, digestion, relieves arthritis, and may soothe skin conditions.

Camphor—Camphor is a waxy, flammable, white crystalline solid with the chemical formula $C_{10}H_{16}O$. Camphor occurs naturally as d-camphor, the l-enantiomer being synthetically produced.

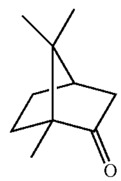

It is commonly found in *cannabis*, rosemary leaves, camphor basil, and in *Cinnamomum camphora*, which goes by several common names including camphor tree, camphorwood, and camphor laurel. Camphor is also found in kapur trees, and a few other related trees in the laurel family, notably *Ocotea usambarensis*.

The ancient Egyptians used camphor as one of the ingredients used for mummification. It has been used as an ingredient in sweet and savory foods in medieval Europe and Arabia. Camphor is readily absorbed through the skin, and when applied topically produces a cooling sensation similar to that of menthol. It acts as a slight local anesthetic, relieves pain, itching and swelling, and has antimicrobial properties. It is used as a cough suppressant, a decongestant, an insect repellent notably for cockroaches and fleas, and is used to make mothballs. Camphor has been used to treat sprains, swellings, inflammation, and fevers. In very small quantities taken internally, it is used to treat minor heart symptoms and fatigue. Camphor increases heart rate, is a skin vasodilator, and reduces appetite.

Isoborneol—Isoborneol is a bicyclic terpene alcohol with the chemical formula $C_{10}H_{18}O$ and the chemical structure:

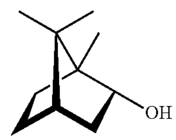

Borneol

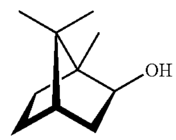

Isoborneol

Isoborneol is a waxy solid with an odor similar to that of camphor and is found in *cannabis* and mugwort. Isoborneol exhibits antiviral properties and is a potent inhibitor of herpes simplex virus type 1. Besides being antiviral, it also has antioxidant, anti-inflammatory, and antimicrobial properties.

Menthol-Menthol is a terpene alcohol with the chemical formula $C_{10}H_{20}O$ and the chemical structure:

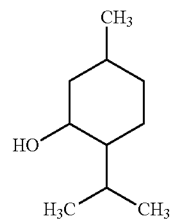

Menthol is found in *cannabis* and in members of the mint family such as corn mint and peppermint (*Menthae piperitae aetheroleum*). Menthol is a white or colorless crystalline solid at room temperature. It is used in candies, cigarettes, cosmetics, personal care products, and medicines.

Menthol produces a cooling sensation on the skin and soft tissues of the mouth by activating the TRPM8 receptor protein that senses the change in temperature in cold-sensing nerves. However, menthol gives a cool sensation without any actual fall in temperature in that area. This lowers inflammation in the area, causing the nearby blood vessels to dilate, and increases blood flow to the area which delivers fresh nutrients to repair the area and removes any toxic wastes generated. This process speeds healing. Menthol may also bind to another receptor called kappa opioid receptor that may also produce a numbing effect.

Menthol exhibits analgesic properties and is used topically to treat inflammatory pain caused by conditions such as arthritis, bursitis, tendonitis, muscle strains or sprains, backache, bone pain, bruising, and cramping.

Menthol cigarettes have a lower cancer risk and cause far less cigarette related cancers than their non-mentholated counterparts, making menthol an important and possibly mitigating component of inhaled *cannabis.*

Menthol is also a powerful penetration enhancer (PE) for transdermal drugs, often increasing drug uptake by a factor of 10 or more.

Cedrene—Cedrene is a sesquiterpene with the chemical formula $C_{15}H_{24}$ and exists in two isomeric forms, α-cedrene and -β-cedrene, which differ in the position of one double bond.

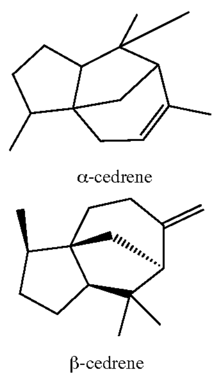

α-cedrene

β-cedrene

Cedrene is a light yellowish transparent oil with the aroma of cedar wood and is found in *cannabis*, fenugreek, and in the essential oil of cedar.

Cedrene possesses antiseptic, antimicrobial, antifungal, and anticancer properties, particularly against T-cell lymphoma, which may occur in the blood as leukemia or in lymph nodes (lymphoma), skin, or other areas of the body.

Nerolidol—Also known as peruviol, nerolidol is a naturally occurring sesquiterpene alcohol present in various plants with a floral odor, and has the chemical formula $C_{15}H_{26}O$. It exists in two isomeric forms, cis and trans, which differ in their geometry about the central double bond. The chemical structures are:

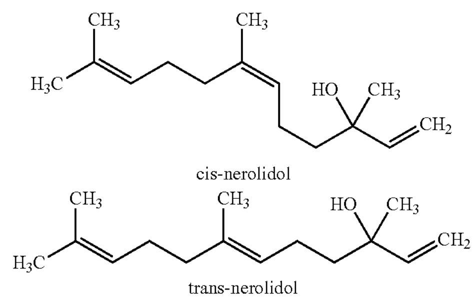

cis-nerolidol trans-nerolidol

Nerolidol has a floral, citrus, woody, fresh bark aroma, and may be found in *Cannabis sativa*, neroli, niaouli, ginger, jasmine, lavender, tea tree, citronella, lemon grass, and *Brassavola nodosa*, a Mexican orchid.

Nerolidol is widely used in perfumes as both a base note fragrance component and as a fixative; it is also used in cosmetics, personal care products, detergents and cleaning products, and as a food flavoring agent.

It has anti-fungal, anti-leishmaniasis (an infection caused by protozoan *Leishmania* parasites, which are spread by the bite of phlebotomine sand flies) and anti-malarial properties. It also produces a sedative effect. It may enhance skin penetration for the transdermal delivery of therapeutic drugs.

Guaiol—Guaiol, also called champacol, is a sesquiterpenoid alcohol found in several plants, including *Cannabis indica*, guaiacum and cypress pine. It is a crystalline solid at room temperature with the chemical formula $C_{15}H_{26}O$ and the structure:

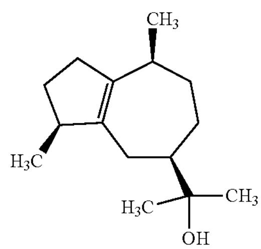 [SMILES: C[C@H]1CC[C@@H](C(C)(C)O)CC2=C1CC[C@@H]2C]

Guaiol has a woody, rosy, floral aroma. *Cannabis* strains known to contain guaiol include Liberty Haze, Blue Kush, Chocolope, and Medical Mass.

Guaiol has been used for centuries as a treatment for diverse ailments ranging from coughs to constipation to arthritis and syphilis. It is also an effective insect repellent and insecticide. Guaiol's potential medical properties include: Antimicrobial, Anti-inflammatory, laxative, diuretic, and insect repellant.

Isopulegol—Isopulegol is a monoterpene alcohol found in *cannabis*, corn mint, European pennyroyal, lemongrass and geranium, and possesses a minty aroma. It has the chemical formula $C_{10}H_{18}O$ and the structure:

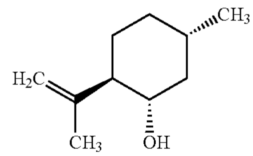

Isopulegol is used as a flavoring agent in food, in cosmetics, and in perfumes, personal care products, and cleaners. It is a chemical precursor to menthol and shows many promising routes for therapeutic use. Isopulegol possesses gastroprotective, anti-convulsive, anti-inflammatory, antioxidant, and stress-reducing effects, and it reduces the severity of seizures and anxiety in animal models.

Geranyl Acetate—Geranyl acetate has several other names including geraniol acetate, and is a monoterpene ester with a sweet, strong, floral rose and fruity aroma. It is a colorless liquid at room temperature and has the chemical formula $C_{12}H_{20}O_2$ with the structure:

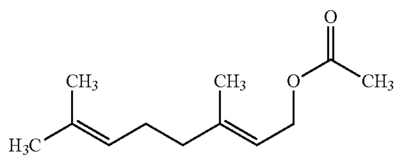

It is used in the fragrance and flavor industries, and is found in products such as soaps, detergents, personal care products, fabric softeners, and as a middle note in perfumes.

Geranyl acetate is found in a variety of natural essential oils, such as *cannabis*, citronella, palmarosa, geranium, coriander, neroli, lemongrass, petitgrain, carrot, *sassafras*, rose, and many others. It exhibits strong antimicrobial, antifungal, and anti-inflammatory effects.

Cymene—Also called p-cymene, para-cymene, methyl-isopropyl-benzene, and 1-isopropyl-4-methylbenzene among others, this aromatic, para substituted benzene ring is an alkylbenzene monoterpene with the formula $C_{10}H_{14}$ and the structure:

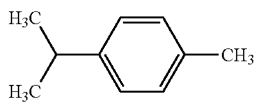

The other two isomers of methyl-isopropyl-benzene are o-cymene (ortho-cymene) and m-cymene (meta cymene), however only p-cymene is a naturally occurring compound. It has a citrusy-woody-spicy odor with herbal hints, and is found in cumin, thyme, anise, coriander, mace, oregano, *eucalyptus* and in *angelica* root and *angelica* seed oil, bay leaf oil, basil oil, carrot seed oil, clove bud oil, clary sage oil, and grape fruit oil. It is used in flavoring beverages, cakes and confectionery, as well as in the fragrance, paint, and furniture industries.

P-cymene has documented anti-inflammatory effects, it shows potential protective effects against acute lung injury, and is effective against pathogenic bacteria, especially *Escherichia coli*. When combined with carvacrol it is also antibacterial and possibly even more so. P-carvacrol, thymol and p-cymene work synergistically together and have anti-fungal properties; p-cymene by itself showed strong antifungal activity against numerous *candida* species. P-cymene also shows anti-inflammatory, antinociceptive and analgesic properties.

A useful derivative of cymene is 2,5-Dimethoxy-p-cymene, or thymohydroquinone dimethyl ether. 2,5-Dimethoxy-p-cymene is a phytochemical found in the essential oils of plants within the family Asteraceae, such as *Arnica montana*. These essential oils, which contain the compound as a major component of the oil, have antifungal, antibacterial, and insecticidal properties. Furthermore, 2,5-Dimethoxy-p-cymene appears to act synergistically with conventional chemotherapy and radiotherapy, and some clinical studies in humans have been initiated.

Eucalyptol—Eucalyptol has many other names, including 1,8-cineol (or cineole), cajeputol; 1,8-epoxy-p-menthane, and eucalyptole. Eucalyptol is a cyclic monoterpenoid ether and it is the main component of *eucalyptus* essential oil having the chemical formula $C_{10}H_{18}O$ and the chemical structure:

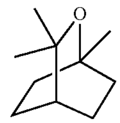

Eucalyptol has a minty, earthy, spicy aroma and is found in several plants including *Cannabis sativa*, camphor laurel, bay leaves, tea tree, mugwort, sweet basil, wormwood, rosemary, common sage, and other aromatic plants. Eucalyptol is used in flavorings in baked goods, confectionery, meat products, beverages, and mouth wash; in fragrances, cigarettes and cosmetics.

Eucalyptol has many medicinal uses. It relieves pain, suppresses coughs, and improves concentration and inner balance. Plants containing eucalyptol enhance meditation and concentration. Eucalyptol has potent antifungal effects and is used as an insecticide and insect repellent. Eucalyptol inhibits cytokine production in lymphocytes and monocytes, giving it an anti-inflammatory effect, and it reduces inflammation and pain when applied topically. It is able to kill in vitro leukemia cells of two cultured leukemia cell lines. Eucalyptol is effective for controlling asthma and reduces airway mucus hypersecretion by its anti-inflammatory cytokine inhibition, and it is an effective treatment for rhinosinusitis. Moreover, eucalyptol has been found to be a powerful penetration enhancer (PE) for transdermal drug delivery, often increasing drug intake by a factor of more than 10 via the transdermal route.

Combining eucalyptol with 5-MTHF may enhance their individual benefits for cognitive function and mental health. Eucalyptol has been shown to have anti-inflammatory and antioxidant effects, while 5-MTHF is involved in the production of neurotransmitters such as serotonin, which is important for regulating mood and cognitive function. By combining these two compounds, it is possible that their effects on cognitive function and mental health could be enhanced, potentially improving conditions such as depression and cognitive decline. Combining eucalyptol with caprylic acid may have potential benefits for gut health and immune function. Eucalyptol has been shown to have antimicrobial and anti-inflammatory effects, while caprylic acid has been shown to have antimicrobial properties and may help promote the growth of beneficial gut bacteria. By combining these two compounds, it is possible that their effects on gut health and immune function could be enhanced, potentially improving conditions such as gut dysbiosis and other immune-related disorders. Combining eucalyptol with cetylated fatty acids may provide potential benefits for joint health and inflammation. Eucalyptol has been shown to have anti-inflammatory and analgesic effects, while cetylated fatty acids have been shown to reduce inflammation and improve joint mobility. By combining these two compounds, it is possible that their effects on joint health and inflammation could be enhanced, potentially improving conditions such as arthritis and other inflammatory joint disorders.

Pulegone—Pulegone, a monocyclic monoterpenoid, is a secondary terpene component of *cannabis*. It exists naturally in two enantiomeric forms, d-pulegone and l-pulegone, with d-pulegone being the most abundant. The chemical formula is $C_{10}H_{16}O$ and the structure is:

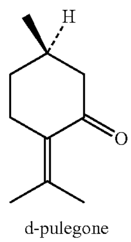

d-pulegone

It has an aroma of peppermint and camphor, and it is found in several plants besides *cannabis*, such as catnip, peppermint, spearmint, pennyroyal, and rosemary. It is used for flavoring foods, drinks, and dental products, as a spice, it is used as fragrance components in detergents and cosmetics, it is used in herbal medicines, perfumery, and aromatherapy.

Pulegone is an emmenagogue, a mucolytic, and is good for congestion of the respiratory system. Pulegone may have significant sedative and fever-reducing properties. It may also alleviate the side effects of short-term memory loss sometimes associated with higher levels of THC. Pulegone is a powerful insecticide.

Traditionally, plants containing pulegone, such as pennyroyal, have been used as herbal teas for non-ulcer dyspepsia, primary dysmenorrhoea, secondary amenorrhoea and oligomenorrhoea, as an abortifacient, and as a diaphoretic. Pennyroyal essential oil has been used for the same conditions. Pulegone is a hepatotoxic (liver poison) and nephrotoxic (kidney poison) constituent of the folklore abortifacient pennyroyal oil.

Today, *Mentha piperita* (peppermint) and *Mentha pulegium* (pennyroyal) are used for colds, headache, migraine, as a diuretic, antispasmodic, anticonvulsive, anti-emetic, heart stimulant, sedative, and to treat the symptoms of inflammatory bowel syndrome. Rosemary inhibits acetylcholinesterase in the brain yielding more acetylcholine and allowing nerve cells to communicate more effectively with one another, giving promise for treatment of memory issues and dementias.

One other terpene found in *cannabis* that bears mentioning is humulene.

Humulene—Humulene is a monocyclic sesquiterpene containing an 11-membered ring and is also known as α-humulene and α-caryophyllene (an isomer of β-caryophyllene). Humulene is often found in combination with it's isomer, β-caryophyllene, it has the chemical formula $C_{15}H_{24}$ and the structure is:

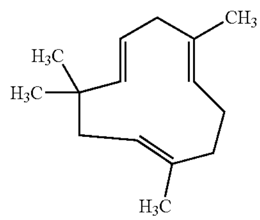

Humulene is found in *Cannabis sativa* strains, hops and Vietnamese coriander, pine trees, orange trees, marsh elders, tobacco, sage, *ginseng*, ginger, and sunflowers, among other plants. Humulene is what gives beer its distinct "hoppy" aroma, and also contributes to the same hoppy aroma in *cannabis*.

Humulene is anti-tumor, anti-bacterial, is a strong anti-inflammatory, and is anorectic (suppresses appetite). It is often blended with β-caryophyllene and used as a potent remedy for inflammation. Humulene aids in weight loss by acting as an appetite suppressant.

In the body, terpenes act on receptors and neurotransmitters. They readily combine with, or dissolve in, lipids or fats. Terpenes may act as serotonin uptake inhibitors, they may enhance norepinephrine activity, and they may increase dopamine activity, and they may augment synaptic γ-aminobutyric acid (GABA) levels by inhibiting re-uptake. These actions are similar to many of the commonly prescribed anti-depressant drugs used today.

The differences in the amounts and types of both cannabinoids and terpenes, along with the other lesser compounds within the *cannabis* varieties, imbue the various *cannabis* extracts with medicinal significance. Adding or increasing one or more of these compounds can alter the effects of *cannabis* extract, as certain compounds work in synergy to augment desirable effects while other compounds act as antagonists to inhibit undesirable effects.

*Cannabis* has been used to treat pain since at least the third millennium BC. In recent decades, and especially since changes in state laws allowing medical use of *cannabis*, there has developed a substantial body of anecdotal evidence that *cannabis*, particularly smoked *cannabis* plant matter, provides substantial relief from chronic pain caused by numerous chronic health conditions such as cancer, multiple sclerosis, arthritis, nerve damage, back pain, fibromyalgia, and similar conditions. In fact, smoked *cannabis* plant matter appears to be a preferred method of pain treatment by those with chronic medical conditions, even though other forms of administration of *cannabis* are available for medical use. This preference is likely due to a variety of factors. First, smoking *cannabis* allows the user to easily control the dosage, as the effects are felt quickly, and additional amounts can be smoked if the initial effects are insufficient. Second, the concentrations of active *cannabis* compounds in the bloodstream are high compared to oral administration, and more powerful, as the active *cannabis* compounds go directly into the bloodstream instead of being processed into other compounds by the liver. Third, the combined effect of the dozens of *cannabis* compounds in *cannabis* plant matter may provide a more pleasant subjective effect, or other benefits such as reduced inflammation, beyond that of a purified cannabinoid medical product. In an aspect of the embodiment, *cannabis* compounds can be selected in formulations designed to specifically to address each of these issues, while avoiding the detriments of smoked *cannabis* plant matter, such as respiratory irritation and the increased potential for lung disease. Further arguing in favor of specifically-formulated *cannabis*-based products is the fact that certain modern North American and European strains of *cannabis* display relatively high concentrations of THC (a potent psychoactive compound), but relatively little CBD or other phytocannabinoid content.

A substantial body of medical literature supports the anecdotal evidence that *cannabis* can be used to treat chronic pain. The endocannabinoid system is active in the control of pain. Compounds found in *cannabis* act on the endocannabinoid system, and certain of these compounds have a powerful analgesic effect. For example, THC is believed to be ten times more powerful than morphine in mediating pain in wide dynamic range neurons in the ventroposterolateral nucleus of the thalamus. Cannabidiol (CBD) is also believed to have strong analgesic effects, due to its function as an endocannabinoid modulator, likely through its ability to promote signaling of the adenosine receptor A2A by inhibiting the adenosine transporter. Cannabigerol (CBG), a "minor cannabinoid" found in small quantities in *cannabis*, is believed to have even greater analgesic activity than THC.

Chronic pain conditions are often resistant to standard treatments, including treatment with opioid medications such as morphine. There is some medical evidence that suggests that cannabinoids are complementary to treatment with opioids, offering additional pain reduction on top of that provided by the opioids. Combining *cannabis* treatments for chronic pain with opioid treatments for chronic pain may have the benefit of reducing patient pain levels, reducing reliance on (and addiction to) opioids, or both.

As mentioned above, a combination of hormone supplementation targeting increased HGH serum levels in conjunction with analgesic therapies and antibiotic/antifungal therapies, delivered transdermally, is desirable. Many uses of HGH supplementation—improved vitality in the elderly, improved performance amongst athletes, wasting disease such as amyotrophic lateral sclerosis (ALS), and myalgic encephalomyelitis/chronic fatigue syndrome (ME/CFS)—are also associated with the need for management of chronic pain or antimicrobial indications. For both topical and systemic purposes, the ability to transdermally deliver both hormone supplementation and treatment of local, topical, or chronic pain is beneficial and indeed preferable over hormone supplementation via injection or oral administration, as long as the skin barrier can be overcome in an appropriate way.

The inventor has conceived, and reduced to practice, a composition and methods of treatment using transdermal supplementation that overcome the limitations of transdermal delivery by various synergistic combinations of penetration enhancers, homeopathic formulations based on large biomolecules, and transdermal administration of hormone precursors in lieu of the actual large biomolecule itself. In some aspects, further methods of treatment of chronic or acute, systemic or local pain are also provided. In further aspects, antimicrobial treatments such as antibiotic, antiviral, and/or antifungal are provided by the addition of antimicrobial phytochemicals to a transdermal gel formulation.

In a preferred aspect, a transdermal gel formulation is provided that comprises a homeopathic formulation of somatropin in conjunction with the HGH precursor L-DOPA, which is more readily amenable to transdermal administration. In an aspect, the homeopathic formulation of somatropin is a 30D formulation. In some aspects, the homeopathic formulation of somatropin may be in the range of 24D-36D, or in a range of 18D-42D. In some aspects, L-DOPA is provided via velvet bean extract. In some aspects, velvet bean extract comprises less than 1% by weight of the transdermal gel formulation. In other aspects, velvet bean extract comprises between 0.1% and 0.9% by weight if the transdermal gel formulation.

In a preferred aspect, the transdermal gel formulation comprises one or more synergistic compounds that target skin health and improve absorption of the homeopathic formulation. Specifically, a synergistic mixture of tocopherols and aloe vera gel may be used to deliver the homeopathic mixture while providing therapeutic benefits for the skin to which it is applied. In an aspect, alpha-tocopherol may be provided in an amount between 400-500 IU, combined with a balance of aloe vera gel. In this mixture, the antioxidant and skin protective benefits of the aloe vera gel as a mixture substrate are enhanced by the presence of alpha-tocopherol such that the resulting mixture's beneficial effects are greater than those of either ingredient individually. Additional tocopherols may be utilized as additives for specific purposes targeting certain effects.

In a preferred aspect, the transdermal gel formulation may further comprise therapeutic doses of milk thistle extract and carnosine, forming a synergistic mixture with the aloe vera gel and vitamin E tocopherols and tocotrienols present.

In a preferred aspect, the transdermal gel formulation comprises a gel-based delivery mixture to improve the absorption and bioavailability of the homeopathic formulation. Specifically, a gel comprising aloe vera gel with the addition of hyaluronic acid in the form of a cross-linked sodium hyaluronate polymer is provided. The aloe vera gel provides a water-based substrate in which the sodium hyaluronate polymer is gelled, while providing skin health benefits to the area to which the gel is applied. The sodium hyaluronate forms a cross-linked polymer that acts as an ideal delivery mechanism for the homeopathic formulation, enhancing absorption across cell membranes through endocytosis to afford a level of bioavailability not possible in non-gelled formulations.

In a preferred aspect, the transdermal gel formulation comprises one or more synergistic penetration enhancers comprising natural phytochemicals. Specifically, in one aspect eucalyptol is provided as a penetration enhancer. In an aspect, eucalyptol is provided in the form of *eucalyptus* in an amount of about between 0.5% and 1.5% by weight of the transdermal gel formulation. In some aspects, more or less *eucalyptus* oil may be used, such as between 0.1% and 0.5% or between 1.5% and 2%; in other aspects between 0.1% and 3% by weight of *eucalyptus* oil is included in the transdermal gel formulation. In another preferred aspect, menthol is used as a natural penetration enhancer, such as by incorporation of about 3% by weight of peppermint oil in the transdermal gel formulation. In some aspects, between 2.5% and 3.5%, or between 2% and 4%, or between 1% and 4%, or less than 5%, by weight, of peppermint oil may be used in the transdermal gel formulation. Moreover, it has been found that the penetration enhancement effects of eucalyptol and menthol are synergistic, such that for any given amount of each the total penetration enhancement is greater than the sum of the penetration enhancements of each used individually. This synergy allows for different mixtures to achieve similar penetration enhancement effects. For example, if it is desired to reduce the odor of mint provided by peppermint oil, or to reduce the known cooling effect of peppermint oil, or to reduce any skin irritation resulting from the peppermint oil on sensitive skin, the combination of both peppermint oil (for menthol) and *eucalyptus* oil (for eucalyptol) allows for relatively more eucalyptol and less menthol to achieve the desired effects without losing the penetration enhancement effects of either phytochemical. The combination of eucalyptol and menthol may improve transdermal penetration of the phytochemicals in the transdermal gel formulation by a factor of 10 to 20 times.

It should be noted that each phytochemical exhibits strongly synergistic effects vis-à-vis the others in the transdermal gel formulation. For example, menthol not only is a potent penetration enhancer but also provides substantial antimicrobial support against viruses, bacteria, and fungi, and it is strongly anti-inflammatory. Thus, menthol is very well-suited for gel applications involving healing of skin, wounds, or other tissues via topical gel application. Furthermore, menthol exhibits analgesic properties and the transdermal gel formulation may be used topically to treat inflammatory pain caused by conditions such as arthritis, bursitis, tendonitis, muscle strains or sprains, backache, bone pain, bruising, and cramping.

Similarly, in addition to being a potent penetration enhancer that operates synergistically with menthol, eucalyptol has many medicinal uses. It relieves pain, suppresses coughs, and improves concentration and inner balance. Plants containing eucalyptol enhance meditation and concentration. Eucalyptol has potent antifungal effects and is used as an insecticide and insect repellent. Eucalyptol inhibits cytokine production in lymphocytes and monocytes, giving it an anti-inflammatory effect, and it reduces inflammation and pain when applied topically. It is able to kill in vitro leukemia cells of two cultured leukemia cell lines. Eucalyptol is effective for controlling asthma and reduces airway mucus hypersecretion by its anti-inflammatory cytokine inhibition, and it is an effective treatment for rhinosinusitis.

In a preferred aspect, CBD is included in the transdermal gel formulation for its strong medicinal effects that are complementary to, and in several ways synergistic with, the effects of the hormone supplement therapeutics (homeopathic somatropin and/or L-DOPA) and the eucalyptol and menthol. In particular, it is well-established that CBD soothes neuropathic and chronic pain and has anti-inflammatory, antioxidant, neuroprotectant, anxiolytic, antidepressant, analgesic, anti-tumor, and anti-psychotic properties. Moreover, delivery of CBD in a transdermal gel that has strong penetration enhancers and additional analgesic agents (e.g., menthol, eucalyptol, and salicin and other salicylic glycosides described below) results in greatly enhanced bioavailability and efficacy of the administered CBD. In a preferred aspect, about 1% by weight of CBD is added to the transdermal gel formulation. In other aspects, between 0.5% and 1.5%, or up to 3%, of CBD by weight may be added to the transdermal gel formulation.

In some aspects, 2,5-Dimethoxy-p-cymene is provided, typically as an extract of *Arnica montana*, to provide anti-fungal, antibacterial, and insecticidal properties useful in topical applications of the transdermal gel formulation. Furthermore, 2,5-Dimethoxy-p-cymene appears to act synergistically with conventional chemotherapy and radiotherapy, and suggests oncological benefits for the transdermal gel formulation.

In some aspects, extract of willow bark is included in the transdermal gel formulation to provide synergistic augmentation of the formulation's analgesic benefits. Specifically, an active ingredient of willow bark is salicin and other salicylic glycosides, which are closely related to salicylic acid (which is the well-known main ingredient of aspirin). Topical application of willow bark in an aspect of the invention provides excellent analgesic benefits both topically and systemically, without any involvement of the digestive system (where the side effects of aspirin can be significant). Since salicin and the other salicylic glycosides in willow bark are small molecules, they benefit from the synergistic penetration enhancement resulting from the use of eucalyptol and menthol for quicker skin penetration. Moreover, salicin and the other salicylic glycosides provide a synergistic analgesic effect with menthol, which has the effect dilating blood vessels in the area of gel application, thus increasing blood flow and the bioavailability od the salicylate glycosides to body tissues.

The skilled person will be aware of a range of possible modifications of the various aspects described above. Accordingly, the present invention is defined by the claims and their equivalents.

What is claimed is:

1. An aqueous gel consisting essentially of:

a. Human growth hormone or Insulin like growth factor 1;

b. Cinnamon extract;

c. Collagen peptides;

d. Elastin peptides;

e. Hyaluronic acid;

f. Aloe vera; and g. Sodium hyaluronate.

2. The aqueous gel of claim 1, wherein the collagen peptides consists essentially of peptides from a plurality of animal-based sources.

3. The aqueous gel of claim 2, wherein the animal-based sources are selected from the group consisting of chicken bone, bovine hide, and fish tissues.

4. The aqueous gel of claim 1, wherein the collagen peptides are present between 0.1 grams and 20 grams.

* * * * *